United States Patent
Wu et al.

(10) Patent No.: US 10,731,185 B2
(45) Date of Patent: Aug. 4, 2020

(54) GENETICALLY ENGINEERED MICROBES AND METHODS FOR PRODUCING CITRAMALATE

(71) Applicant: UNIVERSITY OF GEORGIA RESEARCH FOUNDATION, INC., Athens, GA (US)

(72) Inventors: Xianghao Wu, Daly City, CA (US); Mark Eiteman, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 16/086,883

(22) PCT Filed: Mar. 21, 2017

(86) PCT No.: PCT/US2017/023380
§ 371 (c)(1),
(2) Date: Sep. 20, 2018

(87) PCT Pub. No.: WO2017/165397
PCT Pub. Date: Sep. 28, 2017

(65) Prior Publication Data
US 2019/0093135 A1  Mar. 28, 2019

Related U.S. Application Data

(60) Provisional application No. 62/311,607, filed on Mar. 22, 2016.

(51) Int. Cl.
*C12P 7/46* (2006.01)
*C12N 9/10* (2006.01)
*C12N 15/70* (2006.01)

(52) U.S. Cl.
CPC ............ *C12P 7/46* (2013.01); *C12N 9/10* (2013.01); *C12N 9/1025* (2013.01); *C12N 9/1029* (2013.01); *C12N 15/70* (2013.01); *C12Y 203/01182* (2013.01); *C12Y 203/03001* (2013.01)

(58) Field of Classification Search
None
See application file for complete search history.

(56) References Cited

U.S. PATENT DOCUMENTS

| | | |
|---|---|---|
| 3,666,805 A | 5/1972 | Volker et al. |
| 7,947,483 B2 | 5/2011 | Burgard et al. |
| 8,933,179 B2 | 1/2015 | Johnson et al. |
| 9,080,188 B2 | 7/2015 | Picataggio et al. |
| 9,193,965 B2 | 11/2015 | Liao et al. |
| 9,260,709 B2 | 2/2016 | Achkar et al. |
| 2010/0209986 A1 | 8/2010 | Liao et al. |
| 2014/0245496 A1 | 8/2014 | Hansen et al. |
| 2015/0267231 A1 | 9/2015 | Haas et al. |

FOREIGN PATENT DOCUMENTS

| | | | |
|---|---|---|---|
| WO | WO 2011/087787 A1 | 7/2011 | |
| WO | WO 2012/107758 A1 | 8/2012 | |
| WO | WO 2012/135789 A2 | 10/2012 | |
| WO | WO 2015/022496 * | 2/2015 | ............... C12P 7/42 |
| WO | WO 2015/022496 A1 | 2/2015 | |
| WO | WO 2017/165397 A1 | 9/2017 | |

OTHER PUBLICATIONS

Abdel-Hamid et al., "Pyruvate oxidase contributes to the aerobic growth efficiency of *Escherichia coli*" Microbiology, Jun. 2001; 147(Pt 6):1483-98.

Akesson et al., "On-line detection of acetate formation in *Escherichia coli* cultures using dissolved oxygen responses to feed transients" Biotechnol Bioeng Sep. 5, 1999, 64(5):590-8.

Alper et al., "Tuning genetic control through promoter engineering" Proc Natl Acad Sci USA, Sep. 6, 2005; 102(36):12678-83. Epub Aug. 25, 2005.

Anfelt et al., "Genetic and nutrient modulation of acetyl-CoA levels in synechocystis for n-butanol production" Microb Cell Fact, Oct. 16, 2015; 14:167.

Arya et al., "Differential sensitivities of the growth of *Escherichia coli* to acrylate under aerobic and anaerobic conditions and its effect on product formation" Biotechnol Lett, Nov. 2013; 35(11):1839-1843. Epub Jul. 24, 2013.

Atsumi et al., "Directed evolution of Methanococcus jannaschii citramalate synthase for biosynthesis of 1-propanol and 1-butanol by *Escherichia coli*" Appl Environ Microbiol, 2008; 74(24):7802-8.

Ayoub and Abdullah, "Critical review on the current scenario and significance of crude glycerol resulting from biodiesel industry towards more sustainable renewable energy industry" Renew. Sustainable Energy Rev, 2012; 16(5):2671-86.

Baba et al., "Construction of *Escherichia coli* K-12 in-frame, single-gene knockout mutants: the Keio collection" Mol Syst Biol, 2006; 2:2006.0008. Epub Feb. 21, 2006.

(Continued)

*Primary Examiner* — Suzanne M Noakes
(74) *Attorney, Agent, or Firm* — Mueting, Raasch & Gebhardt, P.A.

(57) ABSTRACT

Provided herein is a genetically engineered microbe which accumulates citramalate. In one embodiment, the microbe includes an exogenous polynucleotide encoding a citramalate synthase which catalyzes the condensation of acetyl CoA and pyruvic acid. Optionally, the microbe also includes a second exogenous polynucleotide encoding a citrate synthase which catalyzes the condensation of acetyl CoA and oxaloacetate, and the citrate synthase activity in the microbe is reduced compared to a control microbe. In one embodiment, the citrate synthase includes at least one amino acid substitution in the acetyl-CoA binding pocket, the mobile loop, the NADH binding site, and the oxaloacetate binding site, or a combination thereof. Also provided herein are methods for using the genetically engineered microbe, including a method for producing citramalate. The method can further include isolating the citramalate.

20 Claims, 27 Drawing Sheets
Specification includes a Sequence Listing.

(56) References Cited

OTHER PUBLICATIONS

Bauer, Jr., "Methacrylic Acid and Derivatives" in *Ullmann's Encyclopedia of Industrial Chemistry*. Wiley-VCH: Weinheim. Oct. 15, 2011; Cover page, publisher's page.
Beatty et al., "Cyclic AMP receptor protein-dependent activation of the *Escherichia coli* acsP2 promoter by a synergistic class III mechanism" J Bacteriol, Sep. 2003; 185(17):5148-57.
Bechthold et al., "Succinic acid: A new platform chemical for biobased polymers from renewable resources" Chem Eng Technol, 2008 May; 31(5):647-54.
Behr et al., "Improved utilisation of renewable resources: new important derivatives of glycerol" Green Chem, 2008; 10:13-30.
Berman et al., "Phosphoenolpyruvate synthetase of *Escherichia coli*. Purification, some properties, and the role of divalent metal ions" J Biol Chem, Oct. 25, 1970; 245(20):5309-5318.
Bermejo et al., "Expression of Clostridium acetobutylicum ATCC 824 genes in *Escherichia coli* for acetone production and acetate detoxification" Appl Environ Microbiol, Mar. 1998; 64(3):1079-1085.
Bernofsky, "An improved cycling assay for nicotinamide adenine dinucleotide" Anal Biochem, Jun. 1973; 53(2):452-8.
Berovic et al., "Citric acid production" Biotechnol Annu Rev, 2007; 13:303-43.
Bhayana et al., "Amino Acid Sequence of *Escherichia coli* Citrate Synthase" Biochem, 1984; 23(13):2900-05.
Bikard et al., "Programmable repression and activation of bacterial gene expression using an engineered CRISPR-Cas system" Nucl Acids Res, Aug. 2013; 41(15):7429-37. Epub Jun. 12, 2013.
Bommareddy et al., "A de novo NADPH generation pathway for improving lysine production of Corynebacterium glutamicum by rational design of the coenzyme specificity of glyceraldehyde 3-phosphate dehydrogenase" Metab. Eng., Sep. 2014; 25:30-7. Epub Jun. 19, 2014.
Bournay et al., "New heterogeneous process for biodiesel production: a way to improve the quality and the value of the crude glycerin produced by biodiesel plants" Catal Today, Oct. 15, 2005; 106(1-4):190-2.
Bowie et al., "Deciphering the Message in Protein Sequences: Tolerance to Amino Acid Substitutions" *Science*, 1990; 247:1306-1310.
Bozell and Petersen, "Technology development for the production of biobased products from biorefinery carbohydrates—the U.S. Departments of Energy's "Top 10" revisited" Green Chem, 2010; 12(4):539-54.
Braman, *In Vitro Mutagenesis Protocols*, Third Edition. Humana Press: Totowa, NJ; 2010. Cover page, title page and table of contents.
Brown et al., "The enzymic interconversion of acetate and acetyl-coenzyme A in *Escherichia coli*" J Gen Microbiology, Oct. 1977; 102(2):327-36.
Buckel and Barker, "Two pathways of glutamate fermentation by anaerobic bacteria" J Bacteriol, Mar. 1974; 117(3):1248-60.
Bunch et al., "The *ldhA* gene encoding the fermentative lactate dehydrogenase of *Escherichia coli*" Microbiology, Jan. 1997; 143(Pt 1):187-95.
Carlsson et al., "Study of the sequential conversion of citric to itaconic to methylacrylic acid in near-critical and supercritical water" Ind Eng. Chem. Res., Aug. 1, 1994; 33(8):1989-96.
Causey et al., "Engineering Escherichia coli for efficient conversion of glucose to pyruvate" Proc Natl Acad Sci USA, Feb. 24, 2004; 101(8):2235-40.
Centeno-Leij a et al., "Improving poly-3-hydroxybutyrate production in *Escherichia coli* by combining the increase in the NADPH pool and acetyl-CoA availability" Antonie Van Leeuwenhoek, Apr. 2014; 105(4):687-96. Epub Feb. 6, 2014.
Chatzifragkou et al., "Production of 1,3-propanediol by Clostridium butyricum growing on biodiesel-derived crude glycerol through a non-sterilized fermentation process" Appl Microbiol Biotechnol, Jul. 2011; 91(1):101-12. Epub Apr. 12, 2011.

Chen et al., "Metabolic engineering of Klebsiella pneumoniae for the de novo production of 2-butanol as a potential biofuel" Bioresour Technol, Dec. 2015; 197:260-5. Epub Aug. 29, 2015.
Choi et al., "Metabolic engineering of Escherichia coli for the production of 1-propanol" Metabolic Engineering, 2012; 14:477-86.
Choi et al., "Improving polyketide and fatty acid synthesis by engineering of the yeast acetyl-CoA carboxylase" J Biotechnol, Oct. 10, 2014; 187:56-9. Epub Jul. 29, 2014.
Contiero et al., "Effects of mutations in acetate metabolism on high-cell-density growth of *Escherichia coli*" J Ind Microbiol Biotech, Jun. 2000; 24(6):421-30.
D'Alessio and Josse, "Glyceraldehyde phosphate dehydrogenase of Escherichia coli" J Biol Chem, Jul. 10, 1971; 246(19):4326-33.
Datsenko et al., "One-step inactivation of chromosomal genes in *Escherichia coli* K-12 using PCR products" Proc Natl Acad Sci USA, Jun. 6, 2000; 97(12):6640-5.
de Kok et al., "The pyruvate dehydrogenase multi-enzyme complex from Gram-negative bacteria" Biochim Biophys Acta, Jun. 29, 1998; 1385(2):353-66.
De Mey et al., "Minimizing acetate formation in *E. coli* fermentations" J Ind Microbiol Biotechnol, 2007 Nov; 34(11):689-700. Epub Aug. 1, 2007.
De Mey et al., "Promoter knock-in: a novel rational method for the fine tuning of genes" BMC Biotechnol, Mar. 24, 2010; 10:26.
Diaz-Ricci et al., "Effect of alteration of the acetic acid synthesis pathway on the fermentation pattern of *escherichia coli*" Biotechnol Bioeng, Dec. 20, 1991; 38(11)1318-24.
Dittrich et al., "Redistribution of metabolic fluxes in the central aerobic metabolic pathway of *E. coli* mutant strains with deletion of the ackA-pta and poxB pathways for the synthesis of isoamyl acetate" Biotechnol Prog, Mar. 2005; 21(2):627-31.
Dittrich et al., "Characterization of the acetate-producing pathways in *Escherichia coli*" Biotechnol Prog, Jul.-Aug. 2005; 21(4):1062-7.
Duckworth and Bell, "Large-scale production of citrate synthase from a cloned gene" Can J Biochem, Dec. 1982; 60(12):1143-7.
Duckworth et al., "Enzyme-substrate complexes of allosteric citrate synthase: Evidence for a novel intermediate in substrate binding" Biochim Biophys Acta, Dec. 2013; 1834(12):2546-53. Epub Aug. 14, 2013.
Duncombe and Frerman, "Molecular and catalytic properties of the acetoacetyl-Coenzyme A thiolase of *Escherichia coli*" Arch Biochem Biophys, Sep. 1976; 176(1):159-70.
Eikmanns et al., "Nucleotide sequence, expression and transcriptional analysis of the Corynebacterium glutamicum gltA gene encoding citrate synthase" Microbiology, Aug. 1994; 140(Pt 8):1817-28.
Eiteman and Chastain, "Optimization of the ion-exchange analysis of organic acids from fermentation" Anal Chim Acta, Feb. 10, 1997; 338(1-2):69-75.
Eiteman and Altman, "Overcoming acetate in *Escherichia coli* recombinant protein fermentations" Trends Biotechnol, Nov. 2006; 24(11):530-6. Epub Sep. 12, 2006.
Emmerling et al., "Metabolic flux responses to pyruvate kinase knockout in *Escherihcia coli*" J Bacteriol, Jan. 2002; 184(1):152-64.
Feng et al., "Characterization of the central metabolic pathways in Thermoanaerobacter sp. strain X514 via isotopomer-assisted metabolite analysis" Appl Environ Microbiol, Aug. 2009; 75(15):5001-8. Epub Jun. 12, 2009.
Feng et al., "Metabolic flux analysis of the mixotrophic metabolisms in the green sulfur bacterium Chlorobaculum tepidum" J Biol Chem, Dec. 10, 2010; 285(50):39544-50. Epub Oct. 11, 2010.
Fultz et al., "Salmonella typhimurium newD and *Escherichia coli* leuC genes code for a functional isopropylmalate isomerase in *Salmonella typhimurium-Escherichia coli* hybrids" J Bacteriol, Mar. 1979; 137(3):1253-62.
Fultz et al., "Wild-type isopropylmalate isomerase in Salmonella typhimurium is composed of two different subunits" J Bacteriol, Oct. 1981; 148(1):210-9.
Gao et al., "Simultaneous quantification of malonyl-CoA and several other short-chain acyl-CoAs in animal tissues by ion-pairing

(56) References Cited

OTHER PUBLICATIONS reversed-phase HPLC/MS" J Chromatogr B Analyt Technol Biomed Life Sci, Jun. 15, 2007; 853(1-2):303-13. Epub Mar. 31, 1981.
Gao et al., "Robust succinic acid production from crude glycerol using engineered Yarrowia lipolytica" Biotechnol Biofuels, Aug. 30, 2016; 9(1):179. eCollection 2016.
Gerhardt et al. (eds.) *Methods for General and Molecular Bacteriology*, American Society for Microbiology, 1994; Cover page, publisher's page, and chapters 13-14 and 16-18.
Goh et al., "Engineering of bacterial methyl ketone synthesis for biofuels" Appl Environ Microbiol, Jan. 2012; 78(1):70-80. Epub Oct. 28, 2011.
Hanai et al., "Engineered synthetic pathway for isopropanol production in *Escherichia coli*" Dec. 2007; 73(24):7814-18.
He et al., "Efficient conversion of itaconic acid to (S)-(+)-citramalic acid by Alcoligenes xylosoydans IL142" J Biosci Bioeng, 2000; 89(4):388-91.
He et al., "Enhanced expression of endoinulinase from Aspergillus niger by codon optimization in Pichia pastoris and its application in inulooligosaccharide production" J Ind Microbiol Biotechnol. Jan. 2014; 41(1):105-14. Epub Nov. 24, 2013.
Highbarger et al., "Mechanism of the reaction catalyzed by acetoacetate decarboxylase. Importance of lysine 116 in determining the pKa of the active-site lysine 115" Biochemistry, Jan. 9, 1996; 35(1):41-6.
Hiremath et al., "1,3-Propanediol production from crude glycerol from jatropha biodiesel process" N Biotechnol, Jan. 31, 2011; 28(1):19-23. Epub Jun. 25, 2010.
Hoefel, E. Wittman, L. Reinecke, D. Weuster-Botz. 2010. Reaction engineering studies for the production of 2-hydroxyisobutyric acid with recombinant Cupriavidus necator H16. Appl. Microbiol. Biotechnol. 88:477-484.
Hong et al., "Requirement of acetyl phosphate for the binding protein-dependent transport systems in *Escherichia coli*" PNAS USA, Mar. 1979; 76(3):1213-7.
Howell et al., "(R)-Citramalate synthase in methanogenic archaea" J Bacteriol, Jan. 1999; 181(1):331-3.
Hua et al., "Analysis of gene expression in *Escherichia coli* in response to changes of growth-limiting nutrient in chemostat cultures" Appl Environ Microbiol, Apr. 2004; 70(4):2354-66.
Iuchi et al., "arcA (dye), a global regulatory gene in *Escherichia coli* mediating repression of enzymes in aerobic pathways" Proc Natl Acad Sci USA, Mar. 1988; 85(6):1888-92.
Iuchi et al., "Purification and phosphorylation of the Arc regulatory components of *Escherichia coli*" J Bacteriol, Sep. 1992; 174(17):5617-23.
Jantama et al., "Eliminating side products and increasing succinate yields in engineered strains of *Escherichia coli* C" Biotechnol Bioengineering, Dec. 1, 2008; 101(5): 887-91.
Jensen et al., "Carbon and energy metabolism of atp mutants of *Escherichia coli*" J Bacteriol, Dec. 1992; 174(23):7635-41.
Kao et al., "A global regulatory role of gluconeogenic genes in *Escherichia coli* revealed by transcriptome network analysis" J Biol Chem, Oct. 28, 2005; 280(43):36079-87. Epub Aug. 31, 2005.
Koebmann et al., "The glycolytic flux in *Escherichia coli* is controlled by the demand for ATP" J Bacteriol, Jul. 2002; 184(14):3909-16.
Kornberg, "The role and maintenance of the tricarboxylic acid cycle in Escherichia coli" in *British Biochemistry Past and Present*. Goodwin (Ed.) Academic Press, London, England; 1970. Cover page, publisher's page, and pages 155-171. 21 pages.
Korz et al., "Simple fed-batch technique for high cell density cultivation of *Escherichia coli*" J Biotechnol, Feb. 21, 1995; 39(1):59-65.
Koser, "Correlation of citrate utilization by members of the colon-aerogenes group with other differential characteristics and with habitat" J Bacteriol, Jan. 1924; 9(1):59-77.
Lakshmi et al., "Selection for citrate synthase deficiency in icd mutants of *Escherichia coli*" J Bacteriol, Jul. 1976; 127(1):76-83.

Lee, et al., "Overproduction of acetate kinase activates the phosphate regulon in the absence of the phoR and phoM functions in *Escherichia coli*" J Bacteriol, May. 1990; 172(5):2245-9.
Lee et al., "Flux adaptations of citrate synthase-deficient *Escherichia coli*" Ann N Y Acad Sci, Nov. 30, 1994; 745:35-50.
Lee and Kim, "Systems strategies for developing industrial microbial strains" Nat Biotechnol, Oct. 2015; 33(10):1061-72.
Leonard et al., "Engineering central metabolic pathways for high-level flavonoid production in *Escherichia coli*" Appl Environ Microbiol, Jun. 2007; 73(12):3877-3886.
Leonard et al., "Combining metabolic and protein engineering of a terpenoid biosynthetic pathway for overproduction and selectivity control" Proc Natl Acad Sci USA, Aug. 3, 2010; 107(31):13654-9.
Li et al., "Effect of poxB gene knockout on metabolism in *Escherichia coli* based on growth characteristics and enzyme activities" World J Microbiol Biotchnol, Jan. 2007; 23(4):573-580.
Li et al., "Dual-phase fermentation enables Actinobacillus succinogenes 130ZT to be a potential role for high-level lactate production from the bioresource" Bioresour Technol, Oct. 2010; 101(19):7665-7667.
Liang et al., "Engineering biological systems with synthetic RNA molecules" Mol Cell, Sep. 16, 2011; 43(6):915-26.
Lichtenthaler et al., "Biosynthesis of isoprenoids in higher plant chloroplasts proceeds via a mevalonate-independent pathway" FEBS Lett, Jan. 6, 1997; 400(3):271-4.
Lin et al., "Genetic reconstruction of the aerobic central metabolism in *Escherichia coli* for the absolute aerobic production of succinate" Biotechnol Bioeng, Jan. 20, 2005; 89(2):148-56.
Lin et al., "Acetyl-CoA synthetase overexpression in *Escherichia coli* demonstrates more efficient acetate assimilation and lower acetate accumulation: a potential tool in metabolic engineering" Appl Microbiol Biotechnol, Aug. 2006; 71(6):870-4. Epub Feb. 22, 2006.
Lin et al., "Improving fatty acid availability for bio-hydrocarbon production in *Escherichia coli* by metabolic engineering" PLoS One, Oct. 17, 2013; 8(10):e78595.
Lutz and Bujard, "Independent and tight regulation of transcriptional units in Escherichia coli via the LacR/O, the TetR/O and AraC/I1-I2 regulatory elements" Nucleic Acids Res, Mar. 15, 1997; 25(6):1203-10.
Lv et al., "Dual regulation of cytoplasmic and mitochondrial acetyl-CoA utilization for improved isoprene production in Saccharomyces cerevisiae" Nat Commun, Sep. 21, 2016; 7:12851.
Ma and Hanna, "Biodiesel production: a review" Bioresource Technol, Oct. 1999; 70(1):1-15.
Machado et al., "A selection platform for carbon chain elongation using the CoA-dependent pathway to produce linear higher alcohols" Metab Eng, Sep. 14, 2012; 14(5):504-11. Epub Jul. 20, 2012.
Martinez et al., "Replacing *Escherichia coli* NAD-dependent glyceraldehyde 3-phosphate dehydrognease (GAPDH) with a NADP-dependent enzyme from Clostridium acetobutylicum facilitates NADPH-dependent pathways" Metab Eng, Nov. 2008; 10(6):352-9. Epub Sep. 23, 2008.
Matsuyama et al., "Nucleotide sequence of the phosphotransacetylase gene of *Escherichia coli* strain K12" Biochim Biophys Acta, Oct. 18, 1994; 1219(2):559-62.
Molina et al., "Molecular characterization of *Escherichia coli* malate synthase G. Differentiation with the malate synthase A isoenzyme" Eur J Biochem, Sep. 1, 1994; 224(2):541-8.
Nagai, "New developments in the production of methyl methacrylate" Appl Catal A:General, Nov. 30, 2001; 221(1-2):367-77.
Nakamura and Whited, "Metabolic engineering for the microbial production of 1,3-propanediol" Curr. Opin. Biotech, Oct. 2003; 14(5):454-9.
Nakamura et al., "Mutations of the Corynebacterium glutamicum NCgl1221 gene, encoding a mechanosensitive channel homolog, induce L-glutamic acid production" Appl. Environ. Microbiol, Jul. 2007; 73(14):4491-8. Epub May 18, 2007.
Nakano et al., "Influence of acetic acid on the growth of *Escherichia coli* K12 during high-cell-density cultivation in a dialysis reactor" Appl Microbiol Biotechnol, Nov. 1997; 48(5):597-601.

(56) References Cited

OTHER PUBLICATIONS

Neidhardt, *Escherichia coli* and Salmonella: Cellular and molecular biology ASM Press: Washington Dc; 1996. Cover page, title page and table of contents.
Ner et al., "Complete Sequence of the glt A Gene Encoding Citrate Synthase in *Escherichia coli*" Biochem, Nov. 8, 1983; 22(23):5543-49.
Nguyen et al., "Comparative Analysis of Folding and Substrate Binding Sites between Regulated Hexameric Type II Citrate Synthases and Unregulated Dimeric Type I Enzymes" Biochem, Oct. 13, 2001; 40(44):13177-87.
Nicolas et al., "Response of the central metabolism of *Escherichia coli* to modified expression of the gene encoding the glucose-6-phosphate dehydrogenase" FEBS Lett, Aug. 7, 2007; 581(20):3771-6. Epub Jul. 3, 2007.
Niersbach et al., "Cloning and nucleotide sequence of the Escherichia coli K-12 ppsA gene, encoding Pep synthase" Molec Gen Genet, Jan. 1992; 231(2):332-6.
Noda et al., "Alterations of cellular physiology in *Escherichia coli* in response to oxidative phosphorylation impaired by defective F1-ATPase" J Bacteriol, Oct. 2006; 188(19):6869-76.
Oh et al., "Efficient production of ethanol from crude glycerol by a Klebsiella pneumonia mutant strain" Bioresour Technol, Feb. 2011; 102(4):3918-22. Epub Dec. 5, 2010.
Ornston and Ornston, "Regulation of glyoxylate metabolism in *Escherichia coli* K-12" J Bacteriol, Jun. 1969; 98(3):1098-108.
Otte, "Enzyme engineering in the context of novel pathways and products" Curr Opin. Biotechnol, Dec. 2015; 35:16-22. Epub Jan. 10, 2015.
Parimi et al., "Eliminating acetate formation improves citramalate production by metabolically engineered *Escherichia coli*" Microb Cell Fact, Jun. 21, 2017; 16(1):114.
Park et al., "Synthesis of methyl ketones by metabolically engineered *Escherichia coli*" J Ind Microbiol Biotechnol, Nov. 2012; 39(11):1703-12. Epub Aug. 1, 2012.
Pereira et al., "Active site mutants of *Escherichia coli* citrate synthase" J. Biol. Chem., 1994; 269(1):412-417.
Phue et al., "Acetate accumulation through alternative metabolic pathways in ackA—pta—poxB—triple mutant in *E. coli* B (BL21)" Biotechnol Lett, Dec. 2010; 32(12):1897-903. Epub Aug. 12, 2010.
Porro et al., "Replacement of a metabolic pathway for large-scale production of lactic acid from engineered yeasts" Appl Environ Microbiol., Sep. 1999; 65(9):4211-5.
Przbylski et al., "Synthesis of the building block 2-hydroxyisobutyrate from fructose and butyrate by Cupriavidus necator H16" Appl Microbiol Biotechnol, Oct. 2013; 97(20):8875-85. Epub Aug. 15, 2013.
Qi et al., "Repurposing CRISPR as an RNA-guided platform for sequence-specific control of gene expression" Cell, Feb. 28, 2013; 152(5):1173-83.
Quail et al., "The pdhR-aceEF-lpd operon of *Escherichia coli* expresses the pyruvate dehydrogenase complex" Mol Microbiol, Apr. 1994; 12(1):95-104.
Quandt et al., "Fine-tuning citrate synthase flux potentiates and refines metabolic innovation in the Lenski evolution experiment" Elife, Oct. 14, 2015; 4:e09696.
Risso et al., "Elucidation of an alternate isoleucine biosynthesis pathway in Geobacter sulfurreducens" J Bacteriol, Apr. 2008; 190(7):2266-74. Epub Feb. 1, 2008.
Rohwerder and Mueller, "Biosynthesis of 2-hydroxyisobutyric acid (2-HIBA) from renewable carbon" Microbial Cell Fact, Feb. 25, 2010; 9:13.
Rose et al., "Enzymatic phosphorylation of acetate" J Biol Chem, Dec. 1954; 211(2):737-56.
Sabourin-Provost and Hallenbeck, "High yield conversion of a crude glycerol fraction from biodiesel production to hydrogen by photofermentation" Bioresource Technol, Jul. 2009; 100(14):3513-7. Epub Mar. 31, 2009.

Salis et al., "Automated design of synthetic ribosome binding sites to control protein expression" Nat Biotechnol, Oct. 2009; 27(10):946-50. Epub Oct. 4, 2009.
Salkind et al., "Acrylates and Methacrylates. Raw Materials, Intermediates, Plant Integration" Ind Eng Chem, Oct. 1, 1959; 51(10):1232-38.
Sambrook et al., *Molecular cloning: a laboratory manual, 2 $^{nd}$* ed. Cold Spring Harbor Laboratory Press: Cold Spring Harbor, New York; 1989. Cover page, title page, and table of contents. 32 pgs.
Sánchez et al., "Efficient succinic acid production from glucose through overexpression of pyruvate carboxylase in an *Escherichia coli* alcohol dehydrogenase and lactate dehydrogenase mutant" Biotechnol. Prog., Mar.-Apr. 2005; 21(2):358-65.
Sánchez et al., "Novel pathway engineering design of the anaerobic central metabolic pathway in *Escherichia coli* to increase succinate yield and productivity" Metab Eng May. 2005; 7(3):229-39.
Saxena et al., "Microbial production of 1,3-propanediol: recent developmns and emerging opportunities" Biotechnol Adv, Nov.-Dec. 2009; 27(6):895-913. Epub Aug. 4, 2009.
Schreiner et al., "E1 enzyme of the pyruvate dehydrogenase complex in Corynebacterium glutamicum: molecular analysis of the gene and phylogenetic aspects" J Bacteriol, Sep. 2005; 187(17):6005-18.
Semkiv et al., "Increased ethanol accumulation from glucose via reduction of ATP level in a recombinant strain of Saccharomyces cerevisiae overexpressing alkaline phosphatase" BMC Biotechnol, May 15, 2014; 14:42.
Singh et al., "Genes restoring redox balance in fermentation-deficient *E. coli* NZN111" Metabol Eng, Nov. 2009; 11(6):347-54. Epub Jul. 21, 2009.
Srere et al., "The citrate condensing enzyme of pigeon breast muscle and moth flight muscle" Acta Chem. Scand., 1963; 17:S129-S134.
Stokell et al., "Probing the Roles of Key Residues in the Unique Regulatory NADH Binding Site of Type II Citrate Synthase of *Escherichia coli*" J Biol Chem, Jun. 23, 2003; 278(37):35435-43.
Sukhija et al., "Developing an extended genomic engineering approach based on recombineering to knock-in heterologous genes to *Escherichia coli* genome" Mol Biotechnol, Jun. 2012; 51(2):109-18.
Tatusova et al, "BLAST 2 Sequences, a new tool for comparing protein and nucleotide sequences," FEMS Microbiol Lett, 1999; 174:247-50.
Todd et al., "The Ruegeria pomeroyi acuI gene has a role in DMSP catabolism and resembles yhdH of *E. coli* and other bacteria in conferring resistance to acrylate" PLoS One, 2012; 7(4):e35947. Epub Apr. 26, 2012.
Tomar et al., "The effect of acetate pathway mutations on the production of pyruvate in *Escherichia coli*" App Microbiol Biotechnol, Jul. 2003; 62(1):76-82. Epub Feb. 26, 2003.
Tomlinson et al., "The influence of zinc, copper, iron and manganese on production of citric acid by A. *niger*" J Bacteriol, 1950; 59:217-224.
Tsuruta et al., "High-level production of amorpha-1,4-diene, a precursor of the antimalarial agent artemisinin, in *Escherichia coli*" PLoS One, 2009; 4(2):e4489. Epub Feb. 16, 2009.
U.S. EPA., Nitrogen, Ammonia. Method 350.1 (Colorimetric).. in *Methods for Chemical Analysis of Water and Wastes*. EPA-600/4-79-020. Mar. 1983; U.S. E. P. A., Cincinnati, Ohio USA. Cover page, Abstract, Table of Contents, and pages 350-1.1 through 350-1.4.
Valgepea et al., "Systems biology approach reveals that overflow metabolism of acetate in *Escherichia coli* is triggered by carbon catabolite repression of acetyl-CoA synthetase" BMC Syst Biol, Dec. 1, 2010; 4:166.
Vemuri et al., "Effects of growth mode and pyruvate carboxylase on succinic acid production by metabolically engineered strains of *Escherichia coli*," Apr. 2002 Appl. Environ. Microbiol. 68:1715-27.
Vemuri et al., "Succinate production in dual-phase Escherichia coli fermentations depends on the time of transition from aerobic to anaerobic conditions," Jun. 2002 J. Ind. Microbiol. Biotechnol. 28:325-332.

(56) References Cited

OTHER PUBLICATIONS

Vemuri et al., "Overflow metabolism in *Escherichia coli* during steady-state growth: transcriptional regulation and effect of the redox ratio," May 2006, Appl. Environ. Microbiol. 72(5):3653-3661.
Vemuri et al., "Increased recombinant protein production in *Escherichia coli* strains with overexpressed water-forming NADH oxidase and a deleted ArcA regulatory protein" Biotechnol Bioeng, Jun. 20, 2006; 94(3):538-42.
Verlinden et al., "Bacterial synthesis of biodegradable polyhydroxyalkanoates" J Appl Microbiol, Jun. 2007; 102(6):1437-49.
Wanner and Wilmes-Riesenberg, "Involvement of phosphotransacetylase, acetate kinase, and acetyl phosphate synthesis in control of the phosphate regulon in *Escherichia coli*" J Bacteriol, Apr. 1992; 174(7):2124-30.
Weitzman, "Regulation of citrate synthase activity in *Escherichia coli*" Biochim Biophys Acta, Oct. 17, 1966; 128(1):213-5.
Weitzman and Danson, "Citrate synthase" Curr Top Cell Regul, 1976; 10:161-204.
Westfall et al., "Multiple pathways for isoleucine biosynthesis in the spirochete Leptospira" J Bacteriol, May 1983; 154(2):846-53.
Whited et al., "Technology Update: Development of a gas-phase bioprocess for isoprene-monomer production using metabolic pathway engineering" Ind Biotechnol, Jun. 23, 2010; 6(3):152-63.
Wiegand et al., "Crystal structure analysis and molecular model of a complex of citrate synthase with oxaloacetate and S-acetonyl-coenzyme A" J Mol Biol, Mar. 25, 1984; 174(1):205-19.
Wu et al., "Adaptation of *Escherichia coli* to elevated sodium concentrations increases cation tolerance and enables greater lactic acid formation" Appl Environ Microbiol, May 2014; 80(9):2880-8. Epub Feb. 28, 2014.
Wu et al., "Production of Citramalate by Metabolically Engineered *Escherichia coli*" Biotechnol Bioengineering, Sep. 2016; 113(12):2670-75.
Wu et al., "Production of Citramalic Acid Using Metabolically Engineered *Escherichia coli*" Poster, Society for Industrial Microbiology and Biotechnology Annual Meeting and Exhibition, New Orleans, LA, Jul. 2016, 1 page.
Wu et al., "Production of Citramalic Acid Using Metabolically Engineered *Escherichia coli*" Presentation at the Society for Industrial Microbiology and Biotechnology Annual Meeting and Exhibition, New Orleans, LA, Jul. 2016; 32 pages.
Wu et al., "Production of Citramalic Acid Using Metabolically Engineered *Escherichia coli*" Presentation at the Institute of Biological Engineering Annual Conference, Greenville, SC, Apr. 2016; 23 pages.
Xu et al., "Isoleucine biosynthesis in Leptospira interrogans serotype lai strain 56601 proceeds via a threonine-independent pathway" J Bacteriol, Aug. 2004; 186(16):5400-9.

Yang and Kessler, "Genetic analysis of the leucine region in *Escherichia coli* b/r: gene-enzyme assignments" J Bacteriol, Jan. 1974; 117(1):63-72.
Yang et al., "Enhanced 2,3-butanediol production from biodiesel-derived glycerol by engineering of cofactor regeneration and manipulating carbon flux in Bacillus amyloliquefaciens" Microb Cell Fact, Aug. 22, 2015; 14:122.
Ye and Yu, "Engineering microbes for isoprene production" Metab Eng, Nov. 2016; 38:125-38. Epub Jul. 14, 2016.
Yim et al., "Metabolic engineering of *Escherichia coli* for direct production of 1,4- butanediol" Nat Chem Biol, May 22, 2011; 7(7):445-52.
Yoon et al., "Enhanced lycopene production in *Escherichia coli* engineered to synthesize isopentenyl diphosphate and dimethylallyl diphosphate from mevalonate" Biotechnol Bioeng, Aug. 20, 2006; 94(6):1025-32.
Yoon et al., "Combinatorial expression of bacterial whole mevalonate pathway for the production of beta-carotene in *E. coli*" J Biotechnol, Mar. 25, 2009; 140(3-4):218-26. Epub Jan. 29, 2009.
Yoshikuni et al., "Redesigning enzymes based on adaptive evolution for optimal function in synthetic metabolic pathways" Chem Biol, Jun. 2008; 15(6):607-18.
Zhang et al., "Molecular basis of the inhibitor selectivity and insights into the feedback inhibition mechanism of citramalate synthase from Leptospira interrogans" Biochem J, Jun. 12, 2009; 421(1):133-43.
Zhang et al., "A synthetic metabolic pathway for production of the platform chemical isobutyric acid" ChemSusChem, Aug. 22, 2011; 4(8):1068-70. Epub Jul. 8, 2011.
Zhao et al., "Effect of zwf gene knockout on the metabolism of *Escherichia coli* grown on glucose or acetate" Metab Eng, Apr. 2004; 6(2):164-74.
Zhou et al., "Lycopene production in recombinant strains of *Escherichia coli* is improved by knockout of the central carbon metabolism gene coding for glucose-6 phosphate dehydrogenase" Biotechnol Lett, Dec. 2013; 35(12):2137-45. Epub Sep. 24, 2013.
Zhu et al., "Homolactate Fermentation by Metabolically Engineered *Escherichia coli* Strains" Appl Environ Microbiol, Jan. 2007; 73(2):456-64.
Zhu et al., "High glycolytic flux improves pyruvate production by a metabolically engineered *Escherichia coli* strain," Nov. 2008 Appl. Environ. Microbiol. 74:6649. Available online on Sep. 19, 2008.
Zhu et al., "Coproduction of acetaldehyde and hydrogen during glucose fermentation by Escherichia coli" Appl Environ Microbiol, Sep. 2011; 77(18):6441-50. Epub Jul. 29, 2011.
Zhu et al., "Activation of glyoxylate pathway without the activation of its related gene in succinate-producing engineered *Escherichia coli*" Metabolic Engineering, 2013; 20: 9-19.
Zhu et al., "Engineering of acetate recycling and citrate synthase to improve aerobic succinate production in Corynebacterium glutamicum" PLoS One, Apr. 8, 2013; 8(4):e60659. Print 2013.

* cited by examiner

Fig. 24

```
1    -MMVRIFDTTLRDGEQTPGVSLTPNDKLEIAKKLDELGVDVIEAGSAITSKGEREGIKLI
4    -MMVRIFDTTLRDGEQTPGVSLTPNDKLEIAKKLDELGVDVIEAGSAVTSKGEREGIKLI
2    MSLVKLYDTTLRDGTQAEDISFLVEDKIRIAHKLDEIGIHYIEGGWPGSNPKDVAFFKDI
3    MRNIRIYDTTLRDGVQGQGISFTVEDKLKIVKVLDEFGVAYIEAGNPGSNPKDIEFFERV
         :::*******  *   .:*:   :**:.*.: ***:*:   **.*    :.   :   ::  :

1    TKEGLN-AEICSFVRALPV--------DIDAALECDVDSVHLVVPTSPIHMKYKLRKTED
4    TKEGLN-AEICSFVRALPV--------DIDAALECDVDSVHLVVPTSPIHMKYKLRKTED
2    KKEKLSQAKIAAFGSTRRAKVTPDKDHNLKTLIQAEPDVCTIFGKTWDFHVHEALRISLE
3    KNIKLKNAKLIAFGSTRRANTTTEEDANVISLLNADTEVVTIFGKSWDFQVTEILKTTLE
        .:  *. *:: :*   :  .            :: : ::.: :    :.   :  :::     *: : :

1    EVLETALKAVEYAKEHGLIVELSAE---DATRSDVNFLIKLFNEGEKVGADRVCVCDTVG
4    EVLVTALKAVEYAKEQGLIVELSAE---DATRSDVNFLIKLFNEGEKVGADRVCVCDTVG
2    ENLELIFDSLEYLKANVPEVFYDAEHFFDGYKANPDYAIKTLKAAQDAKADCIVLCDTNG
3    ENLKMIYDTVKFFKDKGKSVIFDAEHFFDGYKQNPEYALKTLEVALEAGVDSVCLCDTKG
     * *       .:::: *  :      *   .**    *.  :  :  ::  :*   ::   .  .*  :  :*** *

1    VLTPQKSQELFKKITENVNLPVSVHCHNDFGMATANTCSAVLGGAVQCHVTVNGIGERAG
4    VLTPQKSQELFKKITENVNLPVSVHCHNDFGMATANACSAVLGGAVQCHVTVNGIGERAG
2    GTMPFELVEIIREVRKHITAPLGIHTHNDSECAVANSLHAVSEGIVQVQGTINGFGERCG
3    GAFPMEVYDITKTVVDKFNTEVGIHCHNDNGMAVADSIMAVQAGAIQLQGTINGYGERCG
         *  :    ::   : :  . ..:..  :..:*  ***    *.*:: **   *  :*  :  *:** ***.*

1    NASLEEVVAALKILYGYDTK--IKMEKLYEVSRIVSRLMKLPVPPNKAIVGDNAFAHEAG
4    NASLEEVVAASKILYGYDTK--IKMEKLYEVSRIVSRLMKLPVPPNKAIVGDNAFAHEAG
2    NANLCSIIPALKLKMKRECIGDDQLRKLRDLSRFVYELANLSPNKHQAYVGNSAFAHKGG
3    NANLCTLIPNLQLLMGYKCVPDENLKQLTHLARFVSEIANVTYDERAPYVGKNAFSHKAG
     **.*   ::      ::          .     :: .:*  .::*:* .:   ::        **..**:*:.*

1    IHVDGLIKNTETYEPIKPEMVGNRRRIILGKHSGRKALKYKLDLMGINVSD---EQLNKIY
4    IHVDGLIKNTETYEPIKPEMVGNRRRIILGKHSGRKALKYKLDLMGINVSD---EQLNKIY
2    VHVSAIQRHPETYEHLRPELVGNMTRVLVSDLSGRSNILAKAEEFNIKMDSKDPVTLEIL
3    MHADAVNKNTYSYELIDPSLVGNSRTFLISEVAGRGAVLNAINEIDPTITKDSPETKLIL
      :*...:  ::   :**  :  *.:***    .::..  :**    :   : :.  .:  .               *

1    ERVKEFGDLGKYISDAD---LLAIVREVTGKLVEEKIKLDELTVVSG---NKITPIASVKL
4    ERVKEFGDLGKYISDAD---LLAIVREVTGKLV---------------------------
2    ENIKEMENRGYQFEGAEASFELLMKRALGTHRK-FFSVIGFRVIDEKRHEDQKPLSEATI
3    DKLKEMEYLGYQYENAGGSLELLIRKVLGKYKP--AFNLKEFKVIVNEPSVNS-VNSSALI
     :.:**:        *      ..*     :  :::..  *..

1    HYKGEDITLIETAYGVGPVDAAINAVRKAIS-----GVADIKLVEYRVEAIGGG---TDALI
4    ------------------------------------------------------------
2    MVKVGGKIEHTAAEGNGPVNALDNALRKALEKFYPRLKEVKLLDYKVRVLPAGQGTASSI
3    KVEVDSIEEIAAAEGDGPVHALDNAVRRVLERFYPQIKEMRLTDYKVRVLDSNSATAAKV
```

Fig. 24 (Cont.)

```
1      EVVVKLRKGTEIVEVRKSDADIIRASVDAVMEGINMLLN-----------
4      --------------------------------------------------
2      RVLIESGDKESRWGTVGVSENIVDASYQALLDSVEYKLHKSEEIEGSKK
3      RVIIESTDGKDSWSTIGVSTDIIEASWRALVDSIEYKLNKES-------
```

Fig. 25

```
11    MIK-----------------NSQIPSEFYKKYNVKKGLRD---INGKGV---LAGLTNIS
8     MFERDIVATDNNKAVLHYP-GGEFEMDIIEASEGNNGVVLGKMLSETGLITFDPGYVSTG
7     ---------MADKKAQLVIEGAAPVELPILTGTVGPD-VIDVRGLGATGHFTFDPGFMATA
5     ---------ADTKAKLTLNGDTAVELDVLKGTLGQD-VIDIRTLGSKGVFTFDPGFTSTA
6     ---------MSDAKAKITLGGDTAIELDVLKGTLGQD-VIDIRSLGSKGVFTFDPGFTSTA
9     ------------------------------------------------MVHYGLKGIT
10    ------------------------------------------------MTVTRGLEGVV
                                                              *

11    AIHSFDKEGNQIPGILEYRAYNIKDIINDLRKENRFGFEEMTYLLLFGELPTANELQEFQ
8     STESKITYIDGDAGILRYRGYDIADLAEN------ATFNEVSYLLINGELPTPDELHKFN
7     SCESKITYIDGDKGILLHRGYPIEQLAEQ------SDYLETCYLLLNGELPNAEQKAQFV
5     SCESKITFIDGDEGILLHRGFPIDQLATD------SNYLEVCYILLNGEKPTQEQYDEFK
6     SCESKITFIDGDEGILLHRGFPIDQLATE------SNYLEVCYILLYGEKPTQAEYDEFK
9     CVETSISHIDGEKGRLIYRGHHAKDIALN------HSFEEAAYLILFGKLPSTEELQVFK
10    ATTSSISSII--DDTLTYVGYDIDDLAEN------ASFEEVVYLLWHRELPTKEQLEELK
        : .     . * : ..    ::   :        :* *::   :*.  :   :

11    NLLASRRTLPEFFIRETILTN-PSSDVMNSMSRCILALASYDEKVSDI-SIENVLEQSFG
8     DEIRHHTLLDEDFKSQFNVFP-RDAHPMATLASSVNILSTYYQDQLNPLDEAQLDKATVR
7     STVKNHTMVHEQLKSFFNGFR-RDAHPMAVMCGVVGALSAFYHDSLDINNPQHREISAVR
5     TTVTRHTMIHEQITRLFHAFR-RDSHPMAVMCGITGALAAFYHDSLDVNNPRHREIAAFR
6     TTVTRHTMIHEQITRLFHAFR-RDSHPMAVMCGITGALAAFYHDSLDVNNPRHREIAAYR
9     DKLAAERNLPEHIERLIQSLP-NNMDDMSVLRTVVSALGENT-------YTFHPKTEEAIR
10    KQLAENAEIPNEIIEHFKLYPIDKVHPMAALRTAVSLLGLYD-EEADVMTKEANYRKAIR
         :  .: ::       . . *  :    *.                      :

11    LIADFPLLAIYSYQSYVHYFKKESLYIHYPDPKMTTAENILRMLRPD-C---HYTEVEAK
8     LMAKVPMLAAYAHRA------RKGAPYMYPDNSLNARENFLRMMFGYPTEPYEIDPIMVK
7     LVAKMPTLAAMVYKY------SMGQPMMYPRNDLSYAENFLHMMFNTPCEIKPISPVLAK
5     LLSKMPTMAAMCYKY------SIGQPFVYPRNDLSYAGNFLNMMFSTPCEPYEVNPILER
6     LLSKMPTMAAMCYKY------SIGQPFVYPRNDLSYAGNFLRMMFATPCEEYEVNPVLER
9     LIAITPSIIAYRKRW------TRGEQAIAPSSQYGHVENYYYMLTGE------QPSEAKKK
10    LQAKIPTIVTAFARV------RKGLEPVAPRKDLSFAANFLYMLTGK------EPDDIATE
      * : * :      :       .   * .  *  *:                      .

#                                      #
11    VLDIALILHMEHGGGNNSTFTTHVVTSSGTDTYATIAAALSSLKGPKHGGANIKAAKMLE
8     ALDKLLILHADHE-QNCSTSTVRMIGSAQANMFVSIAGGINALSGPLHGGANQAVLEMLE
7     AMDRIFILHADHE-QNSTSTVRLAGSSGANPFACIAAGIAALWGPAHGGANEAVLTMLD
5     AMDRILILHADHE-QNASTSTVRTAGSSGANPFACIAAGIASLWGPAHGGANEAALKMLE
6     AMDRILILHADHE-QNASTSTVRTAGSSGANPFACIAAGIASLWGPAHGGANEAALKMLE
9     ALETYMILATEHG-MNASTFSARVTLSTESDLVSAVTAALGTMKGPLHGGAPSAVTKMLE
10    AFNKALVLHADHE-LNASTFTARVCVATLSDIYSGITAAIGALKGPLHGGANEAVMKMLT
       .::  ::: *  :*    * ** :.:   ::  ::    :: ..: :: ** ****    . **
```

Fig. 25 (Cont.)

```
                                               #                #
11      NIKENISNYEDDAEIEKYLHKILNKEVFDKQGLIYGIGHAIYSLSDPRFEVFKSYVETLV
8       DIKSNH-----GGDATEFMNKVKNKE---DGVRLMGFGHRVYKNYDPRAAIVKETAHEIL
7       EIGDVS-------NIDKFIAKAKDKN---DPFKLMGFGHRVYKNRDPRATVMKQTCDEVL
5       EISSVK-------HIPEFVRRAKDKN---DSFRLMGFGHRVYKNYDPRATVMRETCHEVL
6       EISSVE-------HIPEFVRRAKDKN---DSFRLMGFGHRVYKNYDPRATVMRETCHEVL
9       DIGEKE-------HAEAYLKEKL--E---KGERLMGFGHRVYKTKDPRAEALRQKAEEVA
10      EIGTVD-------NVEPYIRRKL--A---NKEKIMGFGHRVYRKGDPRAKHLKKMSEKLT
        :*              .   ::  .       :  *:**  :*     ***    .:.   . :

#                          #
11      KEKGLEEEFKLYEKVARLAPKVISENRKIYKTICPNVDFYSGFVYRILEIPQELFTPLFA
8       EHLGGD--DLL-DLAIKLEEIALADDYFISRKLYPNVDFYTGLIYRAMGFPTDFFTVLFA
7       RELGIKNDPQL-ELAMRLEEIALTDPYFIERSLYPNVDFYSGIILKAIGIPTSMFTVIFA
5       KELGTKDD-LL-EVAMELENIALNDPYFIEKKLYPNVDFYSGIILKAMGIPSSMFTVIFA
6       KELGTKDD-LL-QVAMELEHIALNDPYFIEKKLYPNVDFYSGIILKAMGIPSSMFTVIFA
9       GNDRDL---DL-ALHVEAEAIRLLEIYKPGRKLYTNVEFYAAAVMRAIDFDDELFTPTFS
10      KLVGE--------PHWYEMSTKIEEIVTSEKALPPNVDFYSASVYHCLGIDHDLFTPIFA
                  : :       : :       **:**:.  :   :   :    .:**    *:

#                           #
11      IARIVGWLAHRIEEL-INMNKIIRPAYESVL-ESKNYIKLGER-
8       IGRLPGWIAHYREQLGAAGNKINRPRQVYTGNESRKLVPREER-
7       LARTVGWISHWKEML-SSPYKIGRPRQLYTGEQKRDIVALKDRK
5       MARTVGWIAHWSEMH-SDGMKIARPRQLYTGYEKRDFKSDIKR-
6       MARTVGWIAHWNEMH-SDGMKIARPRQLYTGYAKRDFQSDIKR-
9       ASRMVGWCAHVLEQA--ENNMIFRPSAQYTGAIPEEVLS-----
10      VSRTSGWLAHILEQY--DNNRLIRPRAEYTGPGKRAYVPIDERG
         .*  **  :*    *           : **        .    .
```

GENETICALLY ENGINEERED MICROBES AND METHODS FOR PRODUCING CITRAMALATE

CROSS-REFERENCE TO RELATED APPLICATIONS

This application is the § 371 U.S. National Stage of International Application No. PCT/US17/23380, filed Mar. 21, 2017, which claims the benefit of U.S. Provisional Application Ser. No. 62/311,607, filed Mar. 22, 2016, the disclosures of which are incorporated by reference herein in their entireties.

SEQUENCE LISTING

This application contains a Sequence Listing electronically submitted via EFS-Web to the United States Patent and Trademark Office as an ASCII text file entitled "235-02640201_25.txt" having a size of 45 kilobytes and created on Mar. 21, 2017. The information contained in the Sequence Listing is incorporated by reference herein.

SUMMARY OF THE APPLICATION

Provided herein is a genetically engineered microbe which accumulates citramalate. In one embodiment, the microbe includes a first exogenous polynucleotide encoding a citramalate synthase which catalyzes the condensation of acetyl CoA and pyruvic acid. In one embodiment, the microbe also includes a second exogenous polynucleotide encoding a citrate synthase which catalyzes the condensation of acetyl CoA and oxaloacetate, and the citrate synthase activity in the microbe is reduced compared to a control microbe. In one embodiment, the citrate synthase catalyzes the condensation of acetyl CoA and oxaloacetate at a rate that is less than the rate of condensation by the wild type citrate synthase naturally present in the microbe. In one embodiment, the microbe expresses a reduced amount of a citrate synthase protein compared to the control cell. In one embodiment, the genetically engineered microbe is *E. coli*.

In one embodiment, the citrate synthase encoded by the second exogenous polynucleotide includes at least one amino acid substitution, and the amino acid substitution is associated with the reduced citrate synthase activity. In one embodiment, the second exogenous polynucleotide is present in the chromosome. In one embodiment, the at least one amino acid substitution is an amino acid associated with the acetyl-CoA binding pocket, the mobile loop, the NADH binding site, and the oxaloacetate binding site, or a combination thereof, of the citrate synthase. In one embodiment, the at least one amino acid substitution is at a position functionally equivalent to F383, D362, R407, H229, R314, R387, A123, A257, A258, A161, or a combination thereof, of an *E. coli* citrate synthase, such as SEQ ID NO:5. In one embodiment, the substitution of the amino acid at a position functionally equivalent to F383 is F383I, F383M, F383L, F383V, F383A, F383Y, or F383K. In one embodiment, the substitution of the amino acid at a position functionally equivalent to D362 is D362V, D362I, or D362E. In one embodiment, the substitution of the amino acid at a position functionally equivalent to A123 is A123T. In one embodiment, the substitution of the amino acid at a position functionally equivalent to A257 is A257T. In one embodiment, the substitution of the amino acid at a position functionally equivalent to A258 is A258T. In one embodiment, the substitution of the amino acid at a position functionally equivalent to A161 is A161V.

In one embodiment, the genetically engineered microbe produces least 2.5 g/L citramalate in 30 hours based on batch culture conditions, and in one embodiment, the carbon source is glucose and the citramalate yield is at least 0.14 g/g. In one embodiment, the genetically engineered microbe produces least 35 g/L in 132 hours based on fed-batch culture conditions, and in one embodiment, the carbon source is glucose and the citramalate yield is at least 0.4 g/g.

In one embodiment, the genetically engineered microbe further includes reduced expression of a coding region encoding a protein that converts pyruvate to acetate, such as a pyruvate oxidase. In one embodiment, the genetically engineered microbe further includes reduced expression of a coding region encoding a protein that converts acetyl CoA to acetate-phosphate, such as a phosphotransacetylase. In one embodiment, the genetically engineered microbe further includes reduced expression of a coding region encoding a protein that converts acetate-phosphate to acetate, such as an acetate kinase. In one embodiment, the genetically engineered microbe further includes reduced expression of a coding region encoding a protein that converts citramalate to citraconate, such as a 3-isopropylmalate dehydratase. In one embodiment, the genetically engineered microbe further includes reduced expression of a coding region encoding a protein that converts acetyl CoA to malate, such as a malate synthase. In one embodiment, the genetically engineered microbe further includes reduced expression of a coding region encoding a protein that converts pyruvate to lactate, such as a lactate dehydrogenase A. The reduced expression can be due to, for instance, deletion of the coding region or inactivation of the coding region.

Also provided herein is a genetically engineered microbe which includes an exogenous polynucleotide encoding a citramalate synthase which catalyzes the condensation of acetyl CoA and pyruvic acid and accumulates citramalate. The microbe produces at least 20 grams citramalate per liter (g/L), at least 30 g/L, or at least 40 g/L. In one embodiment, the conditions for producing at least 20 grams citramalate per liter (g/L), at least 30 g/L, or at least 40 g/L comprise a fed-batch process. In one embodiment, the microbe further includes reduced expression of a coding region encoding a protein that converts acetyl CoA to citrate. An example of a protein that converts acetyl CoA to citrate is a citrate synthase, such as one encoded by gltA. In one embodiment, the microbe further includes reduced expression of a coding region encoding a protein that converts acetyl CoA to malate, such as one encoded by glcB or aceB. In one embodiment, the microbe further includes reduced expression of a coding region encoding a protein that converts acetate-phosphate to acetate such as one encoded by ackA. In one embodiment, the microbe further includes reduced expression of a coding region encoding a protein that converts pyruvate to lactate, such as one encoded by ldhA.

Also provided are methods. In one embodiment, a method is for producing citramalate. The method includes culturing a microbe described herein under suitable conditions result in the production of citramalate, wherein citramalate is accumulated, typically in the culture medium. In one embodiment, the suitable conditions include use of glucose, glycerol, or a combination thereof, as a carbon source. In one embodiment, the method further includes isolating the citramalate from the microbe or the culture medium, or the combination thereof. In one embodiment, the method further includes chemically synthesizing methacrylic acid from the citramalate.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, tetramers). Thus, the terms peptide, oligopeptide, and polypeptide are all included within the definition of protein and these terms are used interchangeably.

As used herein, "heterologous amino acid sequence" refers to amino acid sequences that are not normally present as part of a protein present in a wild-type cell. For instance, "heterologous amino acid sequence" includes extra amino acids at the amino terminal end or carboxy terminal of a protein that are not normally part of a protein.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. In one embodiment, a polynucleotide is isolated. A polynucleotide can be linear or circular in topology. A polynucleotide can be, for example, a portion of a vector, such as an expression or cloning vector, or a fragment.

As used herein, the term "enriched," means that the amount of a substance relative to the amount of one or more contaminants has been increased at least 2 fold, at least 5 fold, at least 10 fold, or at least 15 fold. Enrichment does not imply that all contaminants have been removed.

As used herein, an "isolated" substance is one that has been removed from a cell and many of the proteins, nucleic acids, and other cellular material of its natural environment are no longer present. A substance may be purified, i.e., at least 60% free, at least 75% free, or at least 90% free from other components with which they are naturally associated. Proteins and polynucleotides that are produced by recombinant, enzymatic, or chemical techniques are considered to be isolated and purified by definition, since they were never present in a cell. For instance, a protein, a polynucleotide, or citramalate can be enriched, isolated, or purified.

As used herein, the terms "coding region," "coding sequence," and "open reading frame" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end.

A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, the term "exogenous protein" and "exogenous polynucleotide" refer to a protein or polynucleotide, respectively, which is not normally or naturally found in a microbe. Since an exogenous protein may include, in some embodiments, a polynucleotide that is normally present in a microbe but is operably linked to a regulatory region to which it is not normally operably linked, in some embodiments an exogenous polynucleotide may encode an endogenous protein. As used herein, the terms "endogenous protein" and "endogenous polynucleotide" refer to a protein or polynucleotide that is normally or naturally found in a cell microbe. An "endogenous polynucleotide" is also referred to as a "native polynucleotide."

As used herein, "control" cell refers to a cell that is the same species as an engineered microbe, but does not include the same modification as the engineered microbe.

Conditions that "allow" an event to occur or conditions that are "suitable" for an event to occur, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 24 is a multiple sequence alignment of citramalate synthase proteins based on the Clustal Omega algorithm. 1, Accession number AAB99402 from *Methanococcus jannaschii* (SEQ ID NO:1); 2, Accession number Q74C76 from *Geobacter sulfurreducens* (SEQ ID NO:2); 3, Accession number WP 009052930 from *Thermoanaerobacter* sp. strain X514 (SEQ ID NO:3); 4, citramalate synthase enzyme CimA3.7 described Atsumi and Liao (2008, Appl. Environmental Microbiol., 74(24):7802-7808) (SEQ ID NO:4).

FIG. 25 is a multiple sequence alignment of citrate synthase proteins based on the Clustal Omega algorithm. 5, *Escherichia coli* (SEQ ID NO:5); 6, *Klebsiella pneumoniae* (SEQ ID NO:6); 7, *Pseudomonas putida* (SEQ ID NO:7); 8, *Corynebacterium glutamicum* (SEQ ID NO:8); 9, *Bacillus subtilis* (SEQ ID NO:9); 10, *Geobacillus stearothermophilus* (SEQ ID NO:10); and 11, *Lactococcus lactis* (SEQ ID NO:11). Asterisk (*) indicates positions which have a single, fully conserved residue; colon (:) indicates conservation between groups of strongly similar properties, roughly equivalent to scoring >0.5 in the Gonnet PAM 250 matrix; period (.) indicates conservation between groups of weakly similar properties, roughly equivalent to scoring=<0.5 and >0 in the Gonnet PAM 250 matrix; number sign (#) indicates the active site residues.

DETAILED DESCRIPTION OF ILLUSTRATIVE EMBODIMENTS

Figure 1:
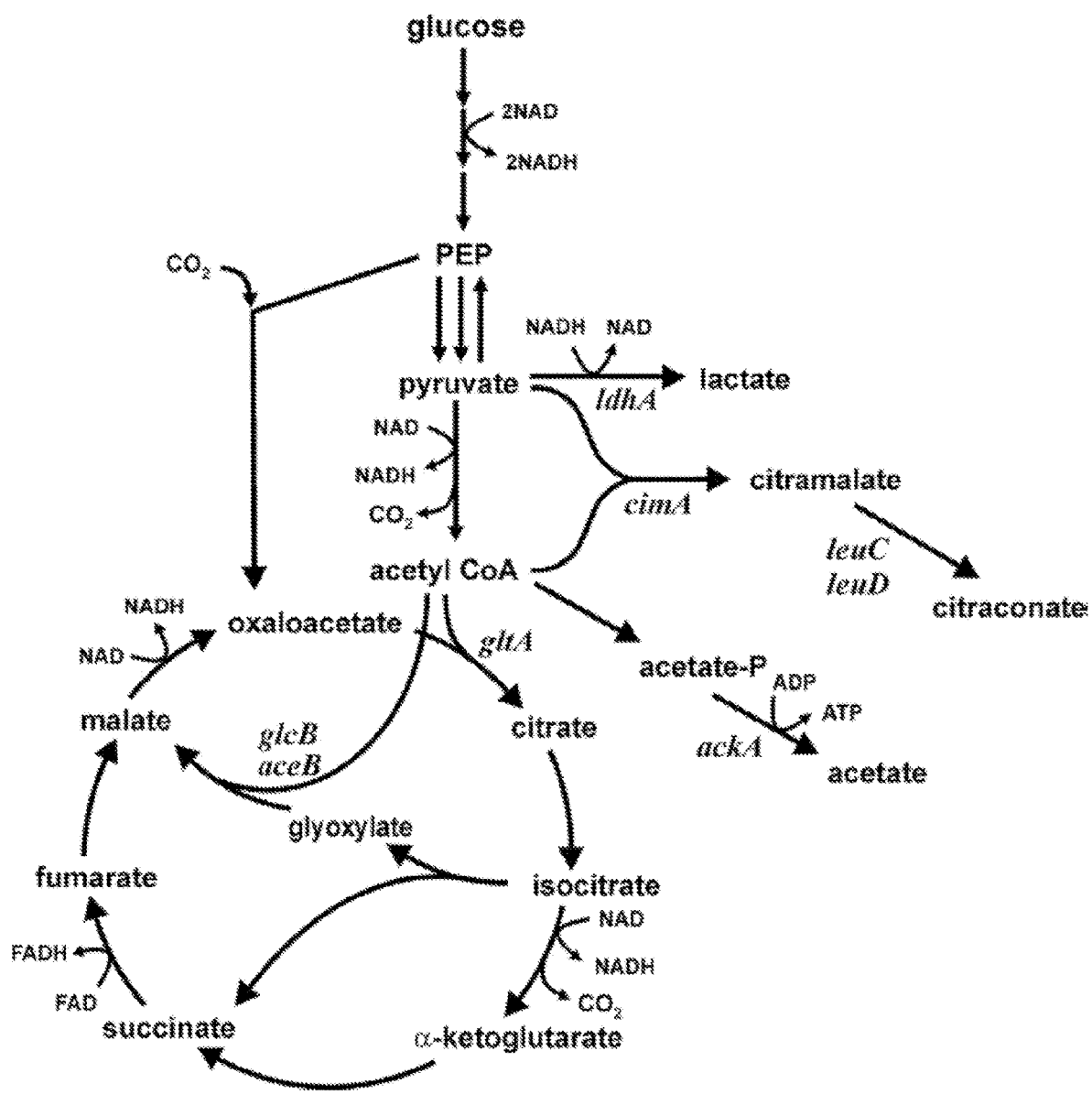
FIG. 1 shows biosynthesis of citramalate in *Escherichia coli* expressing the cimA gene coding citramalate synthase. Key genes and the corresponding enzymes are: ldhA (lactate dehydrogenase), leuC and leuD (3-isopropylmalate dehydratase), gltA (citrate synthase), glcB, and aceB (malate synthase), ackA (acetate kinase).

Described herein is a method for the microbial biosynthesis of citramalate (also referred to herein as citramalic acid, (R)-2-methylmalic acid, and (2R)-2-hydroxy-2-methylbutanedioate), and genetically engineered microbes for producing citramalate. The pathway scheme is shown in FIG. 1 of Example 1. Pyruvate and acetyl CoA can be used as substrates to produce citramalate. The genetically engineered microbe can include other alterations that increase the amount of the pyruvate and acetyl CoA substrates.

The microbial pathway described herein for the production of citramalate from pyruvate and acetyl CoA includes an exogenous enzyme having citramalate synthase activity. As used herein, "citramalate synthase" refers to a protein that, regardless of its common name or native function, catalyses the condensation of pyruvate and acetyl CoA to form citramalate (see FIG. 1 of Example 1), and a protein catalysing such a conversion has citramalate synthase activity. Methods for determining whether a protein has citramalate synthase activity are described in Example 4. Briefly, cell-free extracts can be prepared and citramalate synthase activity measured by the generation of free CoA and its reaction product with 5,5'-dithiobis(2-nitrobenzoic acid) by detection at a wavelength of 412 nm (Srere et al., 1963, Acta Chem. Scand., 17, S129-S134; Howell et al., 1999, J. Bacteriol. 181:331-333). One Unit of activity is the amount of enzyme that generates one µmole of CoA in one minute at 37° C.

Figure 7:
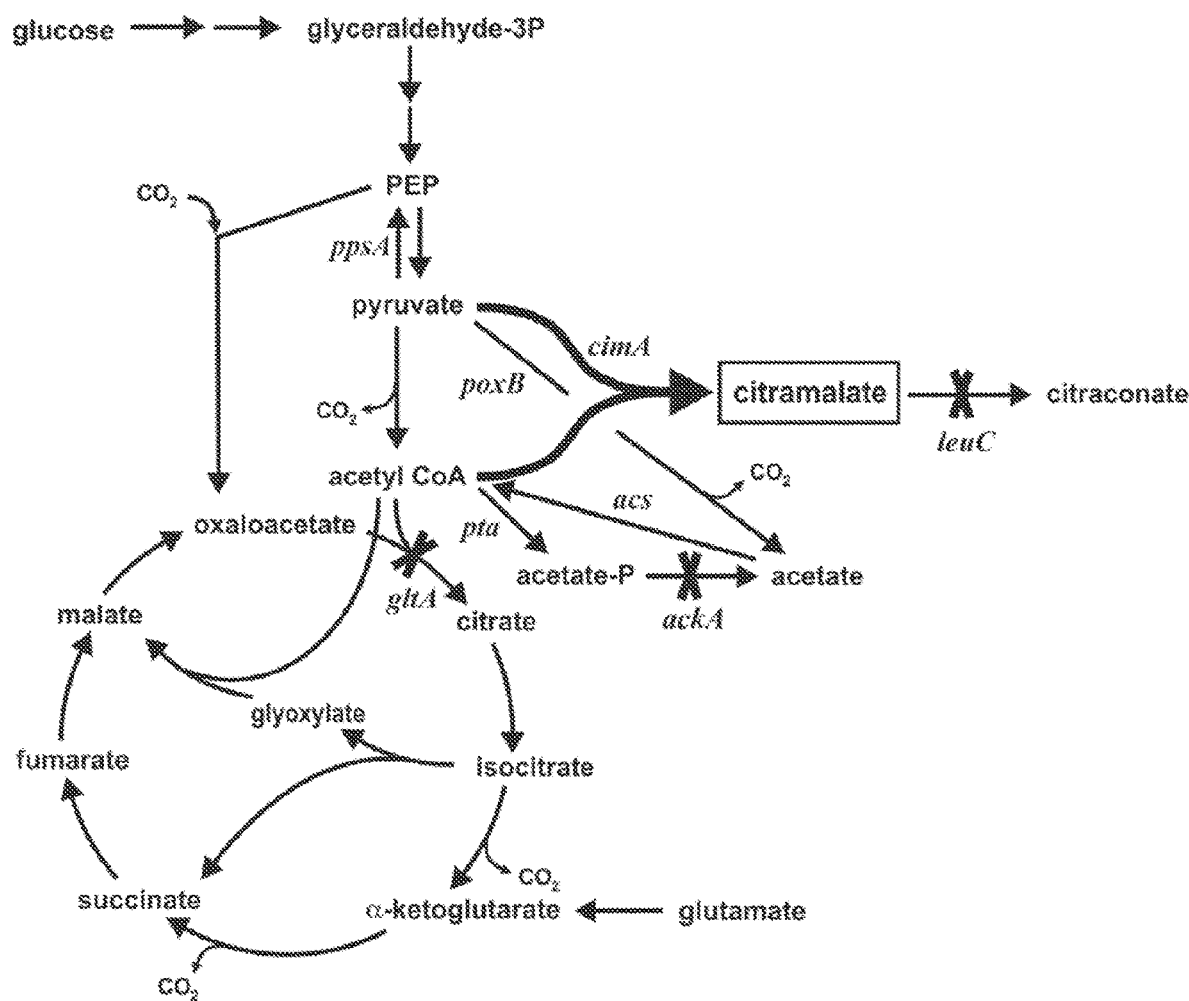
FIG. 7 shows metabolic pathways for citramalate synthesis in *Escherichia coli* expressing cimA coding citramalate synthase. Key enzymes (and corresponding genes) are: citrate synthase (OA), 3-isopropylmalate dehydratase (leuC), acetate kinase (ackA), phosphotransacetylase (pta), acetyl-CoA synthetase (acs), pyruvate oxidase (poxB), phosphoenolpyruvate synthase (ppsA). All strains examined in this study had deletions in the gltA, leuC and ackA genes as indicated.

Enzymes having citramalate synthase activity are known to the skilled worker and are easily obtained. A coding region encoding a protein having citramalate synthase activity can be obtained from a suitable biological source, such as a microbial cell, using standard molecular cloning techniques. Examples of coding regions include, but are not limited to, those that encode CimA (from *Methanococcus jannaschii*: Howell et al., 1999, *J. Bacteriol.* 181:331-333, Accession number AAB99402; and from *Leptospira interrogans*: Westfall et al., 1983, *J. Bacteriol.*, 154:846-853 and Xu et al., 2004, *J. Bacteriol.*, 186:5400-5409, Accession number KWV22152). Other examples of citramalate synthases include Accession number Q74C76 from *Geobacter sulfurreducens* (SEQ ID NO:2), Accession number WP 009052930 from *Thermoanaerobacter* sp. strain X514 (SEQ ID NO:3), Accession number PRK09389 from *Lunatimonas lonarensis*, Accession number PRK12344 from *Marinithermus hydrothermalis*, and the citramalate synthases described by Liao et al. (U.S. Pat. No. 9,193,965, see paragraph spanning column 26 and 27). In one preferred example, a citramalate synthase is described in FIG. 7 of Atsumi and Liao (2008, *Appl. Environ. Microbiol.*, 74(24):7802-7808) (SEQ ID NO:4). Other examples include proteins described as being 2-isopropylmalate synthases (such as Accession number AAB90286 from *Archaeoglobus fulgidus*; Accession number AAM30367 from *Methanosarcina mazei*; Accession number AAC06637, from *Aquifex aeolicus*; Accession number BAA18363 from *Synechocystis* sp.; Accession number CAA19977 from *Streptomyces coelicolor*; and Accession number AAD35637 from *Thermotoga maritima*). Suitable microbes that may harbor coding regions encoding enzymes having citramalate synthase activity include, but are not limited to, those listed above. Coding regions may be isolated using polymerase chain reaction (PCR) with primers designed by standard primer design software which is commonly used in the art. Suitable coding sequences are easily ligated into any standard expression vector by the skilled person. In one embodiment, such an enzyme is a member of the group having E.C. number 2.3.1.182.

In one embodiment, a protein having citramalate synthase activity is, or is structurally similar to, a reference protein. Examples of reference proteins having citramalate synthase activity include those disclosed herein, including SEQ ID NO:1 (Accession number AAB99402), SEQ ID NO:2 (Accession number Q74C76), SEQ ID NO:3 (Accession number WP 009052930), or SEQ ID NO:4. A citramalate synthase that is structurally similar to a reference protein, such as SEQ ID NO:1, SEQ ID NO:2, SEQ ID NO:3, or SEQ ID NO:4 has citramalate synthase activity.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe, or can be produced using recombinant techniques, or chemically or enzymatically synthesized.

Unless modified as otherwise described herein, a pairwise comparison analysis of amino acid sequences can be carried out using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on. Alternatively, proteins may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a protein sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Guidance on how to modify the amino acid sequences of proteins disclosed herein is also provided at Figure A. This figure shows the amino acid sequences of proteins disclosed herein (SEQ ID NOs:1, 2, and 3) in a multiple protein alignment. Identical amino acids are marked with an asterisk ("*"), strongly conserved amino acids are marked with a colon (":"), and weakly conserved amino acids are marked with a period ("."). By reference to this figure, the skilled person can predict which alterations to an amino acid sequence are likely to modify enzymatic activity, as well as which alterations are unlikely to modify enzymatic activity. The crystal structure of at least one citramalate synthase is known (Zhang et al., 2009, Biochem. J., 421:133-143). The skilled person will also recognize that the structure of a CimA can be used to help predict which amino acids may be substituted, and which sorts of substitutions (e.g., conservative or non-conservative) can be made to a citramalate synthase without altering the activity of the protein.

Thus, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence. Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Optionally, the microbe can be further genetically engineered to increase the amount of pyruvate and/or acetyl CoA available as substrate for a citramalate synthase compared to a control cell. Increased citramalate accumulation was expected by reducing the amount of lactate dehydrogenase A by mutation of ldhA (and increase the amount of pyruvate); however there was no observed increase in citramalate accumulation. Mutations of coding regions known to the skilled person increased the amount of pyruvate and/or acetyl CoA available as substrate for a citramalate synthase compared to a control cell. Mutation of glcB and aceB, encoding malate synthase G and malate synthase A, respectively, increased acetyl CoA levels resulted in significant increases of citramalate accumulation. Mutation of a citrate synthase encoded by gltA in *E. coli* to result in no expression of citrate synthase and increased acetyl CoA levels resulted in significant increases of citramalate accumulation. The pta, ackA, and poxB coding regions, which code respectively for phosphotransacetylase, acetate kinase and pyruvate oxidase, respectively, mediate the conversion of acetyl CoA or pyruvate to acetate, and their deletion reduces the formation of this by-product without preventing growth. For example, knocking out ackA and pta resulted in a 4% reduction in acetate accumulation, poxB resulted in a 10% reduction in acetate, while the triple knockout combination of ackA, pta, and poxB reduced acetate formation by 93% (Dittrich et al., 2005, Biotechnol. Prog., 21:627-631). This substantial reduction in acetate formation in the triple knockout does not necessarily translate into more product formation: the triple knockout ackA-pta poxB accumulated the same yield of isoamyl acetate (derived from acetyl CoA) as the ackA-pta double knockout even though the latter generated over ten times as much acetate (Dittrich et al., 2005, Biotechnol. Prog., 21:627-631). However, mutations of pta, ackA, and poxB coding regions resulted in increased amounts of citramalate.

An engineered microbe described herein may optionally include reduced or undetectable expression of a coding region encoding a protein that converts acetyl CoA to malate, such as a malate synthase. Examples of malate synthase proteins include malate synthase G and malate synthase A. A coding region in a microbe encoding a malate synthase can be identified using routine methods. Examples of coding regions encoding a malate synthase include, but are not limited to, a glcB coding region and an aceB coding region.

An engineered microbe described herein may optionally include reduced or undetectable expression of a coding region encoding a protein that converts acetyl CoA to acetate-phosphate, such as a phosphotransacetylase. A coding region in a microbe encoding a phosphotransacetylase can be identified using routine methods. Examples of coding regions encoding a phosphotransacetylase include, but are not limited to, a pta coding region.

An engineered microbe described herein may optionally include reduced or undetectable expression of a coding region encoding a protein that converts acetate-phosphate to acetate, such as an acetate kinase. A coding region in a microbe encoding an acetate kinase can be identified using routine methods. Examples of coding regions encoding a acetate kinase include, but are not limited to, an ackA coding region.

An engineered microbe described herein may optionally include reduced or undetectable expression of a coding region encoding a protein that converts pyruvate to acetate, such as a pyruvate oxidase. A coding region in a microbe encoding a pyruvate oxidase can be identified using routine methods. Examples of coding regions encoding a pyruvate oxidase include, but are not limited to, a poxB coding region.

An engineered microbe described herein may optionally include reduced or undetectable expression of a coding region encoding a protein that converts citramalate to citraconate, such as a 3-isopropylmalate dehydratase. A coding region in a microbe encoding a 3-isopropylmalate dehydratase can be identified using routine methods. Examples of coding regions encoding a 3-isopropylmalate dehydratase include, but are not limited to, leuC and leuD.

An engineered microbe described herein may optionally include reduced or undetectable expression of a coding region encoding a protein that converts pyruvate to lactate, such as a lactate dehydrogenase A. A coding region in a microbe encoding a lactate dehydrogenase A can be identified using routine methods. Examples of coding regions encoding a lactate dehydrogenase A include, but are not limited to, a ldhA coding region.

Thus, an engineered microbe described herein can include reduced or undetectable expression of one or more of the coding regions described herein, in any combination. Reduced expression can be obtained by routine methods including modification of a promoter operably linked to the coding region. Undetectable expression can be obtained using routine methods including, but not limited to, deletion of all or part of the coding region, or inactivation of the coding region. Methods of detecting the expression of each of these coding regions, and detecting the activity of each of the enzymes encoded by each coding region, is known to the skilled person and routine. While the glcB, aceB, gltA, pta, ackA, poxB and gltA coding regions are the names of these coding regions in E. coli, the homologous coding regions in other microbes are known and can be readily identified by the skilled person.

In one embodiment, the microbial pathway described herein for the production of citramalate from pyruvate and acetyl CoA does not include citrate synthase, the gene product of the gltA coding region. For instance, a microbe having the microbial pathway for the production of citramalate from pyruvate and acetyl CoA can include a mutation in a OA coding region that reduces citrate synthase activity to an undetectable level. Typically a microbe having a mutation resulting in no detectable citrate synthase requires a second carbon source as a supplement for growth, such as glutamate or another TCA cycle intermediate.

In another embodiment, the microbial pathway described herein for the production of citramalate from pyruvate and acetyl CoA includes citrate synthase produced at a level that reduces, but does not eliminate, the activity of citrate synthase in a cell. Without intending to be limited to theory, it is believed that reduced activity of citrate synthase results in less carbon flux into the TCA cycle via acetyl CoA, and an increased acetyl CoA pool. Thus, such a cell has a metabolic flux of carbon into the TCA cycle that is reduced, but is not eliminated. Advantageously, because the activity of citrate synthase is reduced but not eliminated, a TCA cycle intermediate such as glutamate is not a required component of the medium. In one embodiment, a regulatory sequence operably linked to a gltA coding region is modified to reduce expression of gltA, and thereby decrease the amount of citrate synthase in the cell. In another embodiment, the nucleotide sequence of a gltA coding region is altered to introduce one or more amino acid substitutions into the citrate synthase encoded by the gltA. In another embodiment, a chromosomal copy of a gltA coding region can be disrupted so that the citrate synthase expressed by the coding region is reduced to an undetectable level, and a separate gltA coding region, modified as described herein to reduce activity, is introduced into the cell.

Citrate synthase (E.C. 2.3.3.1 (previously 4.1.3.7)) is an enzyme active in nearly all cells, where it is typically responsible for catalyzing the first reaction of the citric acid cycle: the condensation of acetyl-CoA and oxaloacetate to form citrate. Accordingly, as used herein, "citrate synthase" refers to a protein that, regardless of its common name or native function, catalyses the condensation of acetyl-CoA and oxaloacetate to form citrate (see FIG. 1 of Example 1), and a protein catalysing such a conversion has citrate synthase activity.

Coding regions encoding a citrate synthase are known to the skilled worker and are easily identified. An example of an E. coli gltA coding region is the complement of nucleotides 753,185 to 754,468 (the 5' end of the coding region begins at nucleotide 754,468 and the coding region ends at nucleotide 753,185) at Genbank accession number NC_000913.3, and the citrate synthase encoded by the coding region is available at Genbank accession number P0ABH7. The N-terminal methionine of the E. coli citrate synthase is cleaved by methionine aminopeptidase during maturation (Ner et al., 1983, Biochemistry. 22(23):5243-5249); however, it is not known if citrate synthase proteins of other microbes are processed to remove the N-terminal methionine. Accordingly, each of the citrate synthase proteins shown in FIG. 25 includes an N-terminal methionine except the E. coli citrate synthase. Amino acid substitutions can be introduced into a citrate synthase to reduce, but not eliminate, the activity of the enzyme. Specific examples of mutations include, but are not limited to, amino acids associated with the acetyl-CoA binding pocket, the mobile loop, the NADH binding site, the oxaloacetate binding site, and a combination thereof. Other examples of mutations include, but are not limited to, conservative substitutions of conserved residues.

While the specific residues of a citrate synthase identified herein are based on the numbering of the E. coli enzyme depicted at SEQ ID NO:5, other citrate synthase proteins can have the same substitution at a functionally equivalent residue. As used herein, "functionally equivalent" and "functional equivalent" refers to an amino acid position in a citrate synthase that occurs at a position having the same functional role as that amino acid position in the E. coli enzyme depicted at SEQ ID NO:5.

Functionally equivalent substitution mutations in different citrate synthase proteins occur at homologous amino acid positions in the amino acid sequences of the enzymes. Functionally equivalent amino acid residues in the amino acid sequences of two or more different citrate synthases can be easily identified by the skilled person on the basis of sequence alignment. An example of sequence alignment to identify functionally equivalent residues is set forth in FIG. 25. The corresponding residues in the citrate synthase enzymes from Klebsiella pneumoniae, Pseudomonas putida, Corynebacterium glutamicum, Bacillus subtilis, Geobacillus stearothermophilus, and Lactococcus lactis are identified in the Figure as vertically aligned and are considered positionally equivalent as well as functionally equivalent to the corresponding residue in the E. coli citrate synthase amino acid sequence. Thus, for instance, as shown in FIG. 25, the phenylalanine at position 383 in the E. coli enzyme depicted at SEQ ID NO:5 is functionally equivalent to the phenylalanine at position 380 of a citrate synthase from Klebsiella pneumoniae (SEQ ID NO:6), functionally equivalent to the phenylalanine at position 385 of a citrate synthase from Pseudomonas putida (SEQ ID NO:7), and so on for the other citrate synthase proteins presented in FIG. 25.

Examples of residues that are part of the acetyl-CoA binding pocket include F383 and D362 of an E. coli protein, such as the one described at SEQ ID NO:5, or a functionally equivalent position in another citrate synthase. In one embodiment, a substitution at F383 or D362 can be any amino acid. In one embodiment, a substitution at F383 or D362 can be a conservative amino acid. In one embodiment, a substitution of the phenylalanine at position 383 can be a smaller hydrophobic residue (F383I, F383M, F383L, F383V, F383A) or another residue (e.g., F383Y, F383K). In one embodiment, a substitution of the aspartate at position 362 is D362V, D362I, or D362E.

Examples of residues that are part of the oxaloacetate binding pocket include R407, H229, H305, R314, and R387 of an E. coli protein, such as the one described at SEQ ID NO:5, or a functionally equivalent position in another citrate synthase. In one embodiment, a substitution at R407, H229, R314, or R387 can be any amino acid. In one embodiment, a substitution at R407, H229, R314, or R387 is a conservative substitution.

Examples of residues that are part of the NADH binding site include R109, H110, T111, Y145, R163, K167, Q182, N189, and T204 of an E. coli protein, such as the one described at SEQ ID NO:5, or a functionally equivalent position in another citrate synthase. In one embodiment, a substitution at R109, H110, T111, Y145, R163, K167, Q182, N189, or T204 can be any amino acid. In one embodiment, a substitution at R109, H110, T111, Y145, R163, K167, Q182, N189, or T204 is a conservative substitution.

In one embodiment, one residue that is part of the acetyl-CoA binding pocket, H264 of an E. coli protein, such as the one described at SEQ ID NO:5, or a functionally equivalent position in another citrate synthase, is not modified because an H264A substitution eliminated citrate synthase activity. In another embodiment, one residue that is part of the oxaloacetate binding pocket, H305 of an E. coli protein, such as the one described at SEQ ID NO:5, or a functionally equivalent position in another citrate synthase, is not modified because an H305A substitution eliminated citrate synthase activity.

Other possible mutations include, but are not limited to, A123, A257, A258, and A161 of an E. coli protein, such as the one described at SEQ ID NO:5, or a functionally equivalent position in another citrate synthase. In one embodiment, a substitution at A123, A257, A258, or A161 can be any amino acid. In one embodiment, a substitution at A123, A257, A258, or A161 can be a conservative amino acid. In one embodiment, A123 is substituted with a threonine (A123T). In one embodiment, A257 is substituted with a threonine (A257T). In one embodiment, A258 is substituted with a threonine (A258T). In one embodiment, A161 is substituted with a valine (A161V).

In one embodiment, a citrate synthase can include more than one mutation. In one embodiment, a combination of mutations can include two or more mutations at residues that are part of the acetyl-CoA binding pocket, two or more mutations at residues that are part of the oxaloacetate binding pocket, or two or more mutations at residues that are part of the NADH binding site. In one embodiment, a citrate synthase includes a mutation at F383 and D362, such as, but not limited to, F383M and D362E. In one embodiment, a combination of mutations can include two or more mutations at residues that are present in different domains of the protein, for instance, one residue present in the acetyl-CoA binding pocket and another residue present in the oxaloacetate binding pocket. In one embodiment, mutations at residues A123, A257, A258, and A161 can be in combination with any other mutation described herein.

The crystal structure of E. coli citrate synthase is known (Nguyen et al., 2001, Biochemistry, 40(44):13177-87). Nguyen et al. also includes an alignment with several other citrate synthases (see Table 2 of Nguyen et al.), showing specific residues associated with acetyl CoA and oxaloacetate binding, and residues that are conserved in allosteric citrate synthases (i.e., those which are inhibited by NADH). Guidance on how to modify the amino acid sequences of a citrate synthase to reduce but not eliminate activity is also provided at FIG. 25. This figure shows the amino acid sequences of an E. coli citrate synthase in a multiple protein alignment with other citrate synthases. By reference to this figure, the crystal structure citrate synthase, and other information provided herein and readily available, the skilled person can predict which alterations to an amino acid sequence are likely to modify enzymatic activity, as well as which alterations are unlikely to modify enzymatic activity. For instance, the skilled person would expect that conservative mutations of residues conserved in citrate synthase proteins are likely to reduce activity, and not eliminate it. The activity of mutated citrate synthases can be easily evaluated as described herein, and those with reduced activity introduced into a suitable microbe containing a metabolic pathway for the production of citramalate from acetyl CoA and pyruvic acid intermediates, e.g., containing a citramalate synthase protein, to determine if they are useful for producing citramalate.

A citrate synthase having reduced activity means the activity is reduced compared to the wild type protein. In one embodiment, the Km for acetyl-CoA is increased. An increase in Km for acetyl-CoA can be by a factor of at least 2, at least 3, at least 4, at least 5, at least 6, at least 7, at least 8, at least 9, or at least 10 compared to the wild type protein. In one embodiment, the Km for acetyl-CoA is increased by no greater than a factor of 20 compared to the wild type protein. In one embodiment, the kcat is decreased. A decrease in kcat can be by a factor of at least 2, at least 3, at least 4, at least 5, at least 6, at least 7, at least 8, at least 9, or at least 10 compared to the wild type protein. In one embodiment, the kcat CoA is decreased by no greater than a factor of 20 compared to the wild type protein. Methods for determining whether a protein has citrate synthase activity are described in Example 4. Briefly, cell-free extracts can be prepared and citrate synthase activity measured by the generation of free CoA and its reaction product with 5,5'-dithiobis(2-nitrobenzoic acid) by detection at a wavelength of 412 nm (Srere et al., 1963, Acta Chem. Scand., 17, S129-S134; Howell et al., 1999, J. Bacteriol. 181:331-333). One Unit of activity is the amount of enzyme that generates one µmole of CoA in one minute at 37° C. Methods for determining the Km and kcat of a citrate synthase are known to the skilled person and routine.

A protein having citrate synthase activity with reduced activity is structurally similar to a reference protein. Examples of reference proteins having citrate synthase activity include those disclosed herein, including SEQ ID NOs:5, 6, 7, 8, 9, 10, and 11. A citrate synthase that is structurally similar to a reference protein, such as SEQ ID NOs:5, 6, 7, 8, 9, 10, and 11, has citrate synthase activity.

Thus, as used herein, a citrate synthase protein having reduced activity and useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a a citrate synthase protein having reduced activity and useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Also provided are polynucleotides encoding a citramalate synthase protein, and a citrate synthase protein having reduced activity. Given the amino acid sequence of a citramalate synthase protein or a citrate synthase protein having reduced activity described herein, a person of ordinary skill in the art can determine the full scope of polynucleotides that encode that amino acid sequence using conventional, routine methods. The class of nucleotide sequences encoding a selected protein sequence is large but finite, and the nucleotide sequence of each member of the class may be readily determined by one skilled in the art by reference to the standard genetic code, wherein different nucleotide triplets (codons) are known to encode the same amino acid.

A citramalate synthase polynucleotide and a polynucleotide encoding a citrate synthase protein having reduced activity described herein may include heterologous nucleotides flanking the coding region encoding the protein. The boundaries of a coding region are generally determined by a translation start codon at its 5' end and a translation stop codon at its 3' end.

As used herein, "heterologous nucleotides" refers to a nucleotide sequence that is not normally or naturally found flanking an open reading frame in a cell encoding a wild type citramalate synthase protein or a citrate synthase protein. Examples of heterologous nucleotides include, but are not limited to, a regulatory sequence. The number of heterologous nucleotides may be, for instance, at least 10, at least 100, or at least 1000.

A polynucleotide described herein, such as a citramalate synthase protein or a citrate synthase protein described herein, can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and transposon vectors. A vector may be replication-proficient or replication-deficient. A vector may result in integration into a cell's genomic DNA. Typically, a vector is capable of replication in a host cell, such as *E. coli.*

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as yeast cells, murine cells, and human cells. Suitable prokaryotic cells include eubacteria, such as gram-negative organisms, for example, *E. coli.*

An expression vector optionally includes regulatory sequences operably linked to a polynucleotide encoding a protein, such as a citramalate synthase protein or a citrate synthase protein having reduced activity. An example of a regulatory sequence is a promoter. A promoter may be functional in a host cell used, for instance, in the construction and/or characterization of a polynucleotide encoding a protein described herein, and/or may be functional in the ultimate recipient of the vector. A promoter may be inducible, repressible, or constitutive, and examples of each type are known in the art. In one embodiment, a coding region encoding a citramalate synthase protein is operably linked to an inducible promoter. Inducible promoters are routinely used and are known in the art. An example of an inducible promoter is the lac operon coupled with induction by IPTG. A polynucleotide encoding a protein described herein may also include a transcription terminator. Suitable transcription terminators are known in the art.

A vector introduced into a host cell optionally includes one or more marker sequences, which typically encode a molecule that inactivates or otherwise detects or is detected by a compound in the growth medium. Certain selectable markers may be used to confirm that the vector is present within the target cell. Other selectable markers may be used to further confirm that the vector and/or transgene has integrated into the host cell chromosomal DNA. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, and neomycin.

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are known. Methods for in vitro synthesis also include, for instance, in vitro transcription using a circular or linear expression vector in a cell free system. Expression vectors can also be used to produce a polynucleotide in a cell, and the polynucleotide may then be isolated from the cell.

In one embodiment, a coding region encoding a citramalate synthase for production of citramalate may be introduced into a microbial cell using genetic engineering techniques. In one embodiment, a coding region encoding a citrate synthase present in a cell can be altered to include one or more mutations described herein to reduce the activity of the citrate synthase. In one embodiment, a chromosomal coding region encoding a citrate synthase present in a cell can be knocked out using genetic engineering techniques, and a coding region encoding a citrate synthase, altered as described herein, may be introduced into the microbial cell using genetic engineering techniques. The term "microbe" is used interchangeably with the term "microorganism" and means any microscopic organism existing as a single cell, cell clusters, or multicellular relatively complex organisms. While certain embodiments are described using *E. coli*, the microbes and methods of use are not limited to *E. coli* and there are a number of other options for microbes suitable for engineering to synthesize citramalate in the methods described herein. The suitable microbial hosts for the synthesis of citramalate as described herein include, but are not limited to, a wide variety of bacteria, archaea, and yeast. Suitable microbial hosts include the ability to grow at lower pH values, such as less than pH 6, less than pH 5, or less than pH 4. Other characteristics of a suitable microbial host include, but are not limited to, ability to grow quickly on a medium with minimal components, ability to grow at a higher temperature (e.g., greater than 37° C., greater than 40° C., greater than 50° C., greater than 60° C., or greater than 70° C.), and the ability to resist bacteriophage. Examples of suitable microbes include, but are not limited to, members of the genera *Escherichia* (such as *E. coli*), *Bacillus* (such as *B. subtilis*), *Acinetobacter* (such as *A. baylyi*), *Pseudomonas* (such as *P. putida*), *Saccharomyces* (such as *S. cerevisiae*), and *Lactococcus* (such as *L. lactis*). If necessary, a coding region encoding an enzyme described herein can be modified using routine methods to reflect the codon usage bias of a microbial host cell to optimize expression of a protein. In one embodiment, an enzyme having citramalate synthase activity is selected based on the microbe into which it is introduced. In embodiments where a citrate synthase having reduced activity is introduced into a cell, the enzyme having citrate synthase activity is selected based on the microbe into which it is introduced.

The coding region encoding a citramalate synthase for production of citramalate that is introduced into a microbial cell can be selected by evaluating one or more factors and the microbial cell. Likewise, the coding region encoding a citrate synthase for production of reduced amounts of citrate from acetyl CoA and oxaloacetate that is introduced into a microbial cell can also be selected by evaluating one or more factors and the microbial cell. Factors include the optimal temperature of the enzyme, optimal pH of the enzyme, or a combination thereof. In the case of citramalate synthase, an additional factor is whether the enzyme is inhibited by citramalate. In one embodiment, the microbial cell can be used as guidance in selecting the coding region. For instance, if the microbial cell is one that grows at higher temperatures (e.g., it is a thermophile) and/or low pH (e.g., it is an acidophile), then the coding region can encode a citramalate synthase that has an optimal temperature and/or optimal pH at or near the temperature and pH to which the microbial cell will be exposed. Because citrate synthase is typically present in all cells, the wild type gltA coding region encoding citrate synthase can be knocked out and a copy of the wild type gltA coding region, modified as described herein to reduce activity, can be used.

A cell that has been genetically engineered to produce citramalate may be referred to as a "host" cell, a "recombinant" cell, a "metabolically engineered" cell, a "genetically engineered" cell or simply an "engineered" cell. These and similar terms are used interchangeably. A genetically engineered cell refers to a microbe that has been altered by human intervention, such as by the introduction of at least one exogenous polynucleotide, the decreased expression of an endogenous polynucleotide, or the decreased expression of an endogenous polynucleotide that has been mutated to encode a protein having activity reduced compared to the wild type. Thus, in one embodiment, a genetically engineered cell contains one or more exogenous polynucleotides which have been created through standard molecular cloning techniques to bring together genetic material that is not natively found together. For example, a microbe is a genetically engineered microbe by virtue of introduction of an exogenous polynucleotide. "Engineered" also includes a microbe that has been genetically manipulated such that one or more endogenous nucleotides have been altered. For example, a microbe is an engineered microbe by virtue of introduction of an alteration of endogenous nucleotides into a suitable microbe. For instance, an endogenous coding region can be deleted or mutagenized, or a regulatory region, such as a promoter, can be altered to result in increased or decreased expression of an operably linked endogenous coding region. In another embodiment, an endogenous polynucleotide can be modified to encode a protein having altered activity. The altered activity can be an increase or a decrease of enzymatic activity. In one exemplary embodiment, a gltA coding region is modified to encode a citrate synthase protein with reduced activity DNA sequences used in the construction of recombinant DNA molecules can originate from any species. For example, bacterial DNA may be joined with fungal DNA. Alternatively, DNA sequences that do not occur anywhere in nature may be created by the chemical synthesis of DNA, and incorporated into recombinant molecules. Proteins that result from the expression of recombinant DNA are often termed recombinant proteins. Examples of recombination may include inserting foreign polynucleotides into a cell, inserting synthetic polynucleotides into a cell, or relocating or rearranging polynucleotides within a cell. Any form of recombination may be considered to be genetic engineering and therefore any recombinant cell may also be considered to be a genetically engineered cell.

Genetically engineered cells are also referred to as "metabolically engineered" cells when the genetic engineering modifies or alters one or more particular metabolic pathways so as to cause a change in metabolism. The goal of metabolic engineering is to improve the rate and conversion of a substrate into a desired product. General laboratory methods for introducing and expressing or overexpressing native and nonnative proteins such as enzymes in many different cell types (including bacteria, archaea, and yeasts,) are routine and known in the art; see, e.g., Sambrook et al, *Molecular Cloning: A Laboratory Manual*, Cold Spring Harbor Laboratory Press (1989), and *Methods for General and Molecu-* lar Bacteriology, (eds. Gerhardt et al.) American Society for Microbiology, chapters 13-14 and 16-18 (1994).

The introduction into a cell of a coding region encoding an enzyme for the production of citramalate involves expression or overexpression of an enzyme. An enzyme is "overexpressed" in a recombinant cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present disclosure.

Also provided herein are methods for producing citramalate using the engineered cells described herein. Briefly, and as described and illustrated in more detail elsewhere herein, the host cell is engineered to contain a biosynthetic pathway that converts pyruvate and acetyl CoA to citramalate. Specifically, the host cell is engineered to overexpress an enzyme having citramalate synthase activity. Optionally, the host cell is also engineered to increase the amount of acetyl CoA, pyruvate, or a combination thereof, available for conversion to citramalate.

In one embodiment, the method includes culturing the engineered microbe under conditions suitable for the production of citramalate. An engineered cell described herein can accumulate surprisingly high levels of citramalate. In one embodiment, an engineered cell described herein produces at least 20 gram/liter (g/L), at least 30 g/L, at least 40 g/L, or at least 45 g/L. In one embodiment, an engineered cell described herein produces no greater than 150 g/L, no greater than 125 g/L, no greater than 100 g/L, no greater than 80 g/L, no greater than 70 g/L, or no greater than 60 g/L. In one embodiment, these levels are reached after 132 hours. Conditions for growing cells that accumulate citramalate include a batch and a fed-batch process in a bioreactor supplemented and using the conditions described in Example 4.

In one embodiment, when batch conditions are used an engineered cell described herein produces in 30 hours at least 2.5 g/L, at least 5 g/L, or at least 10 g/L of citramalate, and no greater than 15 g/L or no greater than 20 g/L of citramalate. The citramalate yield on glucose can be at least 0.14 g/g, at least 0.2 g/g, at least 0.3 g/g, or at least 0.35 g/g, and no greater than 0.4 g/g, no greater than 0.45 g/g, or no greater than 0.5 g/g.

In one embodiment, when fed-batch conditions are used with for additions of glucose an engineered cell described herein produces in 132 hours at least 35 g/L, at least 45 g/L, or at least 55 g/L of citramalate, and no greater than 65 g/L, no greater than 70 g/L, or no greater than 75 g/L of citramalate. The citramalate yield on glucose can be at least 0.4 g/g or at least 0.5 g/g, and no greater than 0.6 g/g or no greater than 0.7 g/g.

The citramalate produced via the biosynthetic pathway can be isolated and optionally purified from a genetically engineered cell described herein. It can be isolated directly from the cells, or from the culture medium, for example, during an aerobic or anaerobic fermentation process. In one embodiment, the citramalate is isolated from the culture medium. Isolation and/or purification can be accomplished using known and routine methods. The citramalate may be used in any application, including as the starting point for the synthesis of other compounds, such as the chemical synthesis of methacrylic acid. Methods for using citramalate to produce methacrylic acid (Johnson et al, U.S. Pat. No. 8,933,179) are routine and known in the art.

The genetically engineered cells described herein can be cultured aerobically or anaerobically, or in a multiple phase fermentation that makes use of periods of anaerobic and aerobic fermentation. The decision on whether to use anaerobic and aerobic fermentation depends on variables familiar to the skilled person. Fed-batch fermentation, batch fermentation, continuous fermentation, or any other fermentation method may be used.

In various embodiments different supplements may be included in the medium in which the engineered cells are grown. For instance, when a citrate synthase such as gltA is mutated the medium can be supplemented with glutamate or some other compound "below" citrate in metabolism. Likewise, when an acetate kinase such as ackA is mutated the medium can be supplemented with acetate. The method may also include supplying at least one carbon source such as glucose, xylose, sucrose, arabinose, glycerol, and/or galactose.

In the description particular embodiments may be described in isolation for clarity. Unless otherwise expressly specified that the features of a particular embodiment are incompatible with the features of another embodiment, certain embodiments can include a combination of compatible features described herein in connection with one or more embodiments.

The present invention is illustrated by the following examples. It is to be understood that the particular examples, materials, amounts, and procedures are to be interpreted broadly in accordance with the scope and spirit of the invention as set forth herein.

EXAMPLES

Example 1

Production of Citramalate by Metabolically Engineered *Escherichia coli*

Abstract

Citramalic acid (citramalate) is a five carbon hydroxy-dicarboxylic acid and potential precursor for the production of methacrylic acid from renewable resources. We examined citramalate production in *Escherichia coli* expressing the citramalate synthase gene cimA. Although knockouts in ldhA coding lactate dehydrogenase and glcB/aceB coding malate synthase did not benefit citramalate accumulation, knockouts in gltA coding citrate synthase and ackA coding acetate kinase significantly increased citramalate accumulation compared to the control strain. A fed-batch process in a controlled fermenter using a glucose feed resulted in 46.5 g/L citramalate in 132 h with a yield of 0.63 g/g, over 75% of the theoretical maximum yield from glucose of 0.82 g/g.

Introduction

With growing concern about fossil-energy depletion and sustainability, innovation for "green" processes using renewable resources to produce biochemicals becomes an attractive approach for the chemical industry. Metabolic engineering and synthetic biology approaches have enabled strain modification and bioprocess optimization to generate numerous commodity chemicals such as succinate (Vemuri et al., 2002; Sanchez et al., 2005), 1,3-propanediol (Nakamura and Whited, 2003), 1,4-butanediol (Yim et al., 2011), lactic acid (Porro et al., 1999), isoprene (Lichtenthaler et al., 1997), and glutamate (Nakamura et al., 2007).

Methacrylic acid (MAA) is a commodity chemical used to form an ester polymer, polymethyl methacrylate, widely used as a transparent thermoplastic in construction, furniture, lighting, and medical technologies. The annual global market has been estimated at about 2.2 million tons (Zhang et al., 2011). The most common approach for MAA synthesis currently involves the hydrolysis of methacrylamine sulfate obtained from acetone cyanohydrin (Salkind et al., 1959; Bauer, 2000; Nagai, 2001). Sulfuric acid regeneration and hazards associated with handling and transporting volatile cyanides are major concerns for industrial MAA production. Many companies have investigated the manufacture of MAA from isobutene, isobutyric acid, and ethylene (Bauer, 2000; Nagai, 2001), though none appear to be economically superior to the acetone cyanohydrin route. Interest also exists for the microbial production of MAA and acrylate from renewable resources, which would presumably involve more renewable process and less hazards. However, acrylates are extremely toxic to microorganisms such as *Escherichia coli* (Todd et al., 2012; Arya et al., 2013), and therefore an alternative "hybrid" approach might be pursued. For example, the biochemical-chemical production of MAA could involve the microbial production of an MAA precursor, which is subsequently converted to MAA by a purely chemical transformation. For example, both citric acid and itaconic acid, products of fungal fermentations, can be thermally decarboxylated to methacrylic acid (Carlsson et al., 1994).

Recently, citramalic acid ((R)-2-methylmalic acid, (2R)-2-hydroxy-2-methylbutanedioate, or citramalate) has been shown to be converted directly to MAA by base-catalyzed decarboxylation and dehydration (Johnson et al., 2015). Citramalate is found in bacterial metabolism, for example, anaerobic metabolism of glutamate via the methylaspartate pathway in *Clostridium tetanomorphum* (Buckel and Barker, 1974) and the isoleucine biosynthesis pathway in *Geobacter sulfurreducens* and *Chlorobaculum tepidum* (Risso et al., 2008; Feng et al., 2010). Citramalate synthase (EC 2.3.1.182) has been purified and characterized from *Methanococcus jannaschii* (Howell, 1999). This enzyme coded by the cimA gene catalyzes the specific condensation of pyruvate and acetyl-CoA with the formation of D-(−)-citramalate (R-citramalate). Using screening and directed evolution, a citramalate synthase mutant designated CimA3.7 was found to have improved activity and lack feedback inhibition by L-isoleucine (Atsumi and Liao, 2008). The particular enantiomer (i.e., R-citramalate, S-citramalate or meso-citramalate) does not affect the chemical conversion to MAA (Johnson et al., 2015).

In this study, we demonstrate significant citramalate accumulation by *E. coli* overexpressing citramalate synthase. Because citramalate synthase requires the availability of both pyruvate and acetyl-CoA (FIG. 1), the focus is on metabolic engineering strategies to block the metabolism of these two citramalate precursors.

Materials and Methods
Strain Construction

Strains and plasmids used in this study are shown in Table 1. Gene mutations were transduced into *E. coli* MG1655 from their respective strains in the KEIO collection (Baba et al., 2006) by the P1 phage method. The knockout additional genes in a strain, the Kan antibiotic marker was removed using pCP20 (Datsenko and Wanner, 2000). In knockout strains, forward primers external to the target gene and reverse primers within the kanamycin resistance cassette were used to check for proper chromosomal integration. In cured strains, the removal of the markers was verified by PCR.

TABLE 1

Strains used in this study.

| Strain | Genotype | Notes |
|---|---|---|
| MG1655 | *E. coli* F- λ- ilvG rfb-50 rph-1 | Wild type |
| MEC387 | MG1655 ΔldhA744::(FRT) | This study |
| MEC476 | MG1655 ΔleuC778::(FRT) | This study |
| MEC477 | MG1655 ΔleuD778::(FRT) | This study |
| MEC480 | MG1655 ΔgltA770::Kan | This study |
| MEC481 | MG1655 ΔaceB781::Kan | This study |
| MEC482 | MG1655 ΔglcB749::Kan | This study |
| MEC485 | MG1655 ΔaceB781::(FRT) ΔglcB749::Kan | This study |
| MEC490 | MG1655 ΔgltA770::(FRT) ΔleuC778::Kan | This study |
| MEC491 | MG1655 ΔgltA770::(FRT) ΔleuD778::Kan | This study |
| MEC499 | MG1655 ΔgltA770::(FRT) ΔleuC778::(FRT) ΔackA778::Kan | This study |

The citramalate synthase enzyme CimA3.7 (Atsumi and Liao, 2008) was codon optimized for expression in *E. coli* (GenScript, Piscataway, N.J., USA). The gene was PCR amplified with primers 5'-GGGAAAGGTACCATGATGGTGCGTATCTTTGACACGAC-3' (forward) (SEQ ID NO:12) and 5'-GGGAAACTCAGATCACACCAGTTTGCCCGTCAC-3' (reverse) (SEQ ID NO:13). To construct the plasmid pZE12-cimA, the 1065 bp PCR product was purified and restricted with KpnI and XbaI, and then ligated into the regulable expression vector pZE12-luc (Lutz and Bujard, 1997) which had also been restricted with KpnI and XbaI.

Growth Medium

Defined XC medium contained (per L): 5.00 g glucose, 13.30 g $KH_2PO_4$, 4.00 g $(NH_4)_2HPO_4$, 8.40 mg $Na_2(EDTA).2H_2O$, 1.20 g $MgSO_4.7H_2O$, 4.5 mg thiamine.HCl, 13 mg $Zn(CH_3COO)_2.2H_2O$, 1.5 mg $CuCl_2.2H_2O$, 15 mg $MnCl_2.4H_2O$, 2.5 mg $CoCl_2.6H_2O$, 3.0 mg $H_3BO_3$, 2.5 mg $Na_2MoO_4.2H_2O$, 100 mg Fe(III) citrate, and 100 mg citric acid. Unless otherwise specified, this medium was supplemented with 0.2 g/L L-leucine for the growth of all ΔleuC or ΔleuD strains, and with 2.0 g/L L-glutamate for ΔgltA strains because *E. coli* is unable to utilize citrate under aerobic conditions (Koser, 1924). Additionally, 50 mg/L ampicillin and/or 100 mg/L kanamycin were added for plasmid-containing strains or strains having antibiotic resistance.

Shake Flask, Batch, Fed-Batch and Chemostat Process

To compare various strains for citramalate production in shake flasks, cells were first grown in 3 mL Lysogeny Broth (LB) at 37° C. and 250 rpm (19 mm pitch). After 10-14 h, 0.5 mL was used to inoculate 50 mL of XC medium containing 0.2 mM IPTG in 500 mL baffled shake flasks (in triplicate). After growth at 37° C. and 250 rpm (19 mm pitch) for 24 h, the cultures were analyzed for citramalate synthase activity, citramalate and intracellular acetyl-CoA concentration.

To examine citramalate production under controlled conditions, cells were first grown as described above in 3 mL LB and then 50 mL XC medium. After 18 h the shake flask contents were used to inoculate the 2.5 L bioreactor (Bioflo 2000, New Brunswick Scientific Co., New Brunswick, N.J., USA) containing 1.0 L XC medium with either 20 g/L glucose (batch) or initially 25 g/L glucose and 15 g/L peptone (fed-batch). For batch and fed-batch processes, the agitation was 400 rpm and air was sparged at 1.0 L/min, which maintained the dissolved oxygen above 40% of saturation. The pH was controlled at 7.0 using 30% (w/v)

NaOH, and the temperature at 30° C. Fermentations were run in duplicate. In batch processes 0.2 mM of IPTG was added initially, while in fed-batch processes 0.2 mM of IPTG was added at 9 h. For the fed-batch process, an additional 30 g glucose was added twice when the glucose decreased below 5 g/L.

A continuous fermentation of 600 mL volume was operated as glutamate-limited chemostat and initiated in batch mode in a 1.0 L bioreactor (Bioflo 310, New Brunswick Scientific Co., New Brunswick, N.J., USA). The influent medium contained XC medium but with 20 g/L glucose and 0.5 g/L L-glutamate. A steady-state condition was assumed after five residence times at which time the oxygen and $CO_2$ concentrations in the effluent gas remained unchanged. For dry cell weight (DCW) measurement, three 50.0 mL samples were centrifuged (3300×g, 10 min), the pellets washed by vortex mixing with 10 mL DI water and then centrifuged again. After washing three times, the cell pellets were dried at 60° C. for 24 h and weighed. The pH was controlled at 7.0 using 30% (w/v) NaOH, the temperature at 30° C., an air flow rate of 0.5 L/min, and an agitation of 400 rpm to maintain the DO above 40% saturation.

Analytical Methods

The optical density at 600 nm (OD) (UV-650 spectrophotometer, Beckman Instruments, San Jose, Calif., USA) was used to monitor cell growth. Extracellular organic acids were analyzed by HPLC using a Refractive Index detector as previously described (Eiteman and Chastain, 1997). Glutamate concentration was measured using a glutamate assay kit (Sigma-Aldrich Co., St. Louis, Mo., USA). Acetyl-CoA was analyzed by the previous method (Gao et al., 2007). Briefly, when a culture reached an OD of 1, 15 mL was centrifuged (3300×g, 10 min, 4° C.), the pellet washed with 3 mL Tris-HCl (pH 7.5), and centrifuged again. After washing three times, cell-free extracts were prepared with a French® pressure cell (Thermospectronic, Rochester, N.Y., USA) at a pressure of 14,000 psi. Cell debris was removed by centrifugation (20,000×g, 15 min, 4° C.), and the extract used for acetyl-CoA quantification by HPLC using a Dionex Ultimate 3000 (Thermo Scientific, Bannockburn, Ill., USA) with a reverse-phase 50×4.6 mm C-18 column (Dionex Acclaim PolarAdvantage II, Thermo Scientific, Bannockburn, Ill., USA). Samples were eluted at a flow rate of 600 µL/min using a gradient of 25 mM ammonium acetate (mobile phase A) and 25 mM ammonium acetate in 90% acetonitrile (mobile phase B). Solution B was delivered from 0% to 80% over 5 min at a flow rate of 0.6 mL/min. Acetyl-CoA was detected and quantified by monitoring absorbance at 254 nm.

Cell-free extracts were also used to measure citramalate synthase activity by the generation of free CoA and its reaction product with 5,5'-Dithiobis(2-nitrobenzoic acid) detected at a wavelength of 412 nm (Howell et al., 1999). One Unit of activity is the amount of enzyme which generates one µmole of CoA in one minute at 37° C.

Results

Comparison of Citramalate Formation in Various Strains

Figure 2:
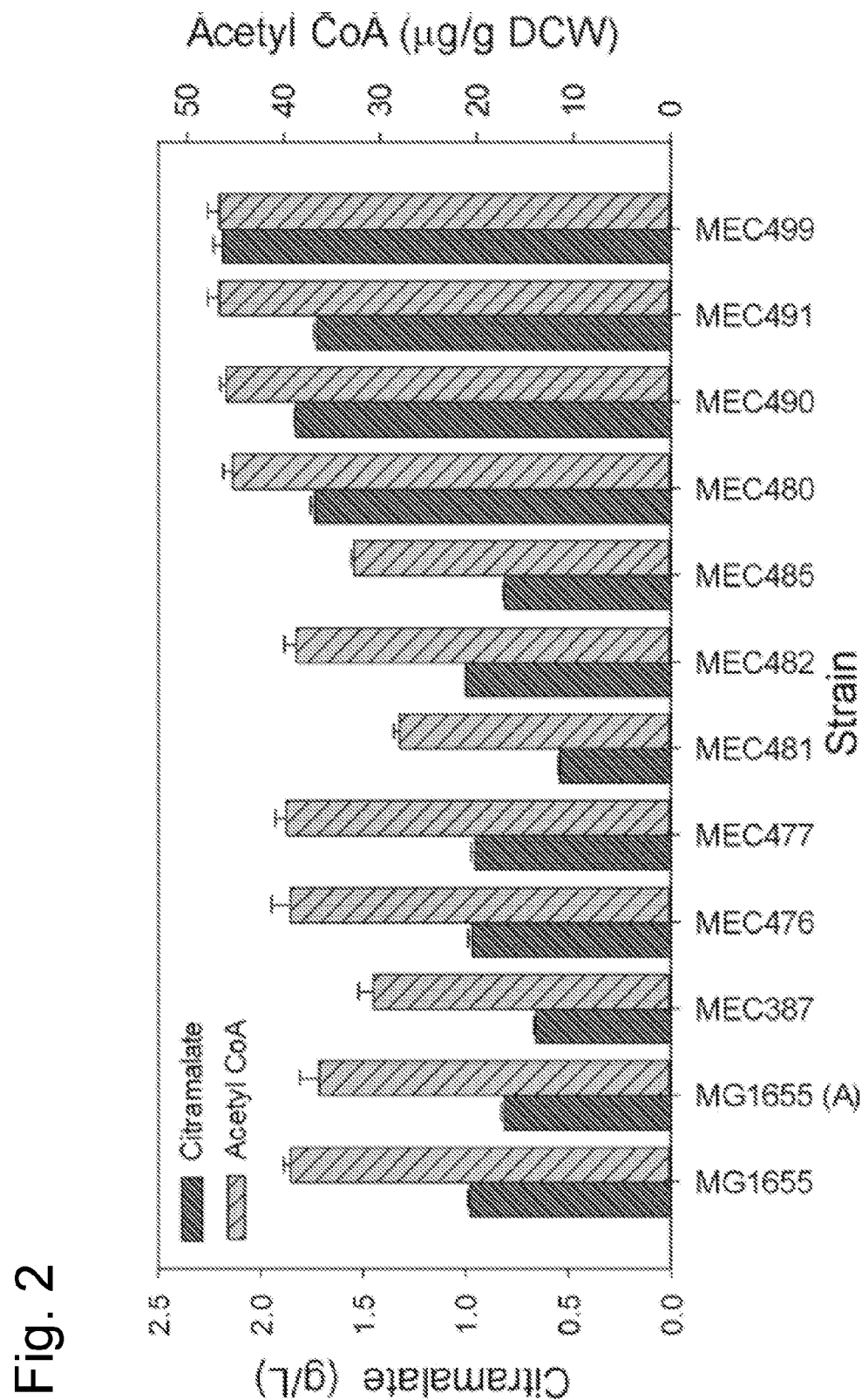
FIG. 2 shows comparison of citramalate production and intracellular acetyl-CoA concentration in shake flasks using various knockout strains of *E. coli* expressing the cimA gene. The defined medium contained 5 g/L glucose, and in triplicate experiments measurements were made at 24 h. The (A) indicates the addition of 1 g/L acetate. The leuC or leuD strains additionally contained 0.2 g/L L-leucine, while gltA strains contained 1 g/L L-glutamate.

Citramalate is generated from the condensation of pyruvate and acetyl-CoA mediated by the enzyme citramalate synthase coded by the cimA gene (FIG. 1). We first examined citramalate formation after 24 h in wild-type E. coli expressing cimA (MG1655/pZE12-cimA) using 5 g/L glucose as sole carbon source (FIG. 2). Because acetyl-CoA is a precursor to citramalate, we also examined its accumulation using a medium containing 5 g/L glucose and 1 g/L acetate. About 1 g/L citramalate accumulated when glucose was the sole carbon source, and 0.81 g/L accumulated in the presence additionally of acetate (FIG. 2). Interestingly, the intracellular acetyl-CoA concentration was also slightly lower in the acetate-containing medium (38.7 µg/g versus 36.3 µg/g).

Because citramalate synthase requires pyruvate as a substrate, we next examined the effect of a knockout in the ldhA gene coding lactate dehydrogenase. Although lactate does not normally accumulate during aerobic growth of E. coli, this gene is transcribed during aerobic growth, especially at low pH (Bunch et al., 1997). Surprisingly, MEC387/pZE12-cimA accumulated only 0.66 g/L citramalate, 34% less than observed in MG1655/pZE12-cimA. Similarly, MEC387/pZE12-cimA resulted in an intracellular acetyl-CoA concentration of 30.7 µg/g, about 20% less than MG1655 expressing citramalate synthase (FIG. 2).

Citramalate could potentially be metabolized in E. coli by 3-isopropylmalate dehydratase coded by the leuC (large subunit) and leuD (small subunit) genes (Fultz et al., 1979; Fultz and Kemper, 1981). Those two subunits are both required for the activity of isopropylmalate isomerase, which catalyzes the second step in leucine biosynthesis in E. coli (Yang and Kessler, 1974). With the deletion of either leuC or leuD, E. coli did not grow in XC medium containing glucose as the sole carbon source. Growth was restored by the addition of L-leucine into the medium (data not shown), and therefore 0.2 g/L L-leucine was used for studies involving strains with either of these gene knockouts. Both MEC476/pZE12-cimA and MEC477/pZE12-cimA accumulated citramalate to about 1.0 g/L, unchanged from the citramalate concentration generated by MG1655/pZE12-cimA (FIG. 2). We also observed no difference in intracellular acetyl-CoA concentration, suggesting that citramalate degradation by 3-isopropylmalate dehydratase is not significant in shake flask cultures. Of course, this potential degradation pathway might become relevant with additional knockouts or under extended fermentation conditions.

We next studied knockouts in enzymes which are involved in the metabolism of acetyl-CoA. Acetyl-CoA enters the glyoxylate shunt via malate synthase coded by the glcB and aceB genes (Ornston and Ornston, 1969; Molina et al., 1994) and the tricarboxylic acid cycle via citrate synthase coded by the OA gene (Eikmanns et al., 1994). We therefore constructed MEC480 (MG1655 gltA), MEC481 (MG1655 aceB), MEC482 (MG1655 glcB) and MEC485 (MG1655 aceB glcB). Compared to MG1655/pZE12-cimA, MEC481/pZE12-cimA showed about 50% lower citramalate accumulation, while MEC482/pZE12-cimA resulted in a statistically identical citramalate concentration. The strain having knockouts in both malate synthase genes, MEC485/pZE12-cimA, resulted in an intermediate concentration of citramalate. Not surprisingly, MEC480 was unable to grow on XC medium with glucose as sole carbon source, though growth was restored when the medium additionally contained 1 g/L L-glutamate. This gltA strain accumulated 1.74 g/L citramalate, and also 13% greater intracellular acetyl-CoA (45.3 µg/g) than MG1655/pZE12-cimA. Since MG1655/pZE12-cimA grown in XC medium supplemented with 1 g/L L-glutamate also yielded about 1 g/L citramalate (data not shown), we attribute the 74% increase in citramalate formation in MEC480/pZE12-cimA to the gltA knockout, and not to the presence of glutamate.

The effects of leuC and leuD gene knockouts on citramalate production in the gltA strain were also investigated. The final citramalate attained by MEC490 (MG1655 gltA leuC) expressing citramalate synthase was 1.83 g/L while 1.73 g/L was obtained by MEC491/pZE12-cimA. Acetyl- CoA levels were similar in MEC490/pZE12-cimA and MEC491/pZE12-cimA, just slightly higher than MEC480/pZE12-cimA (FIG. 2).

Knocking out gltA grown in the presence of 1 g/L L-glutamate, resulted in a significant increase in acetate production compared to the other strains, and similar to previous results which also reported an increase in pyruvate accumulation (Lee et al., 1994). In this study, MEC490/pZE12-cimA generated 0.26 g/L acetate in 24 h, while MG1655/pZE12-cimA and other strains accumulated negligible acetate (0.03 g/L). To reduce acetate formation in the gltA knockout and potentially further increase acetyl CoA availability and citramalate yield, we constructed MEC499 (MG1655 gltA leuC ackA) having additionally a knockout in the ackA gene encoding acetate kinase (Lee et al., 1990; Matsuyama et al., 1994). A deletion of the ackA gene reduces acetate formation and correspondingly increases acetyl-CoA accumulation (Diaz-Ricci et al., 1991). Compared to MEC490/pZE12-cimA, MEC499/pZE12-cimA generated only 0.06 g/L acetate in 24 h. Moreover, MEC499/pZE12-cimA achieved the highest citramalate concentration of 2.19 g/L, over twice the final concentration as MG1655/pZE12-cimA. The intracellular acetyl-CoA concentration of 47.0 µg/g was about 20% higher than observed in MG1655/pZE12-cimA.

Steady-State Fermentation

Since MEC499/pZE12-cimA showed greatest citramalate and intracellular acetyl-CoA concentrations, we selected this strain for a chemostat experiment using glutamate-limited conditions. We reasoned that a glutamate-limited process would allow the highest yield of citramalate from (excess) glucose. Using a dilution rate of about 0.06 $h^{-1}$, the yield of citramalate on glucose was 0.77 g/g compared to a maximum theoretical yield of 0.82 g/g, and acetate was not detected in the effluent.

Citramalate Production in Controlled Fermenters

Figure 3:
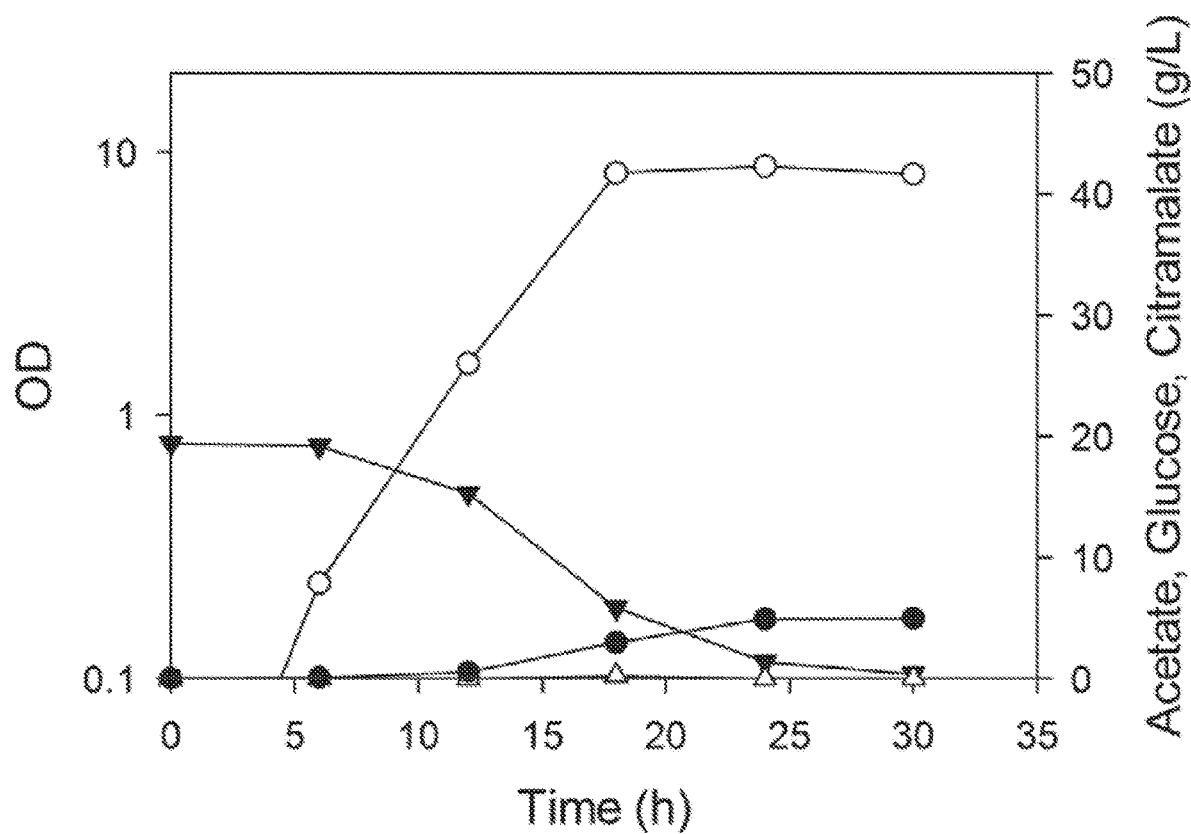
FIG. 3 shows citramalate production in a batch fermentation using MG1655/pZE12-cimA: OD (O), citramalate (•), glucose (▼), and acetate (Δ).
Figure 4:
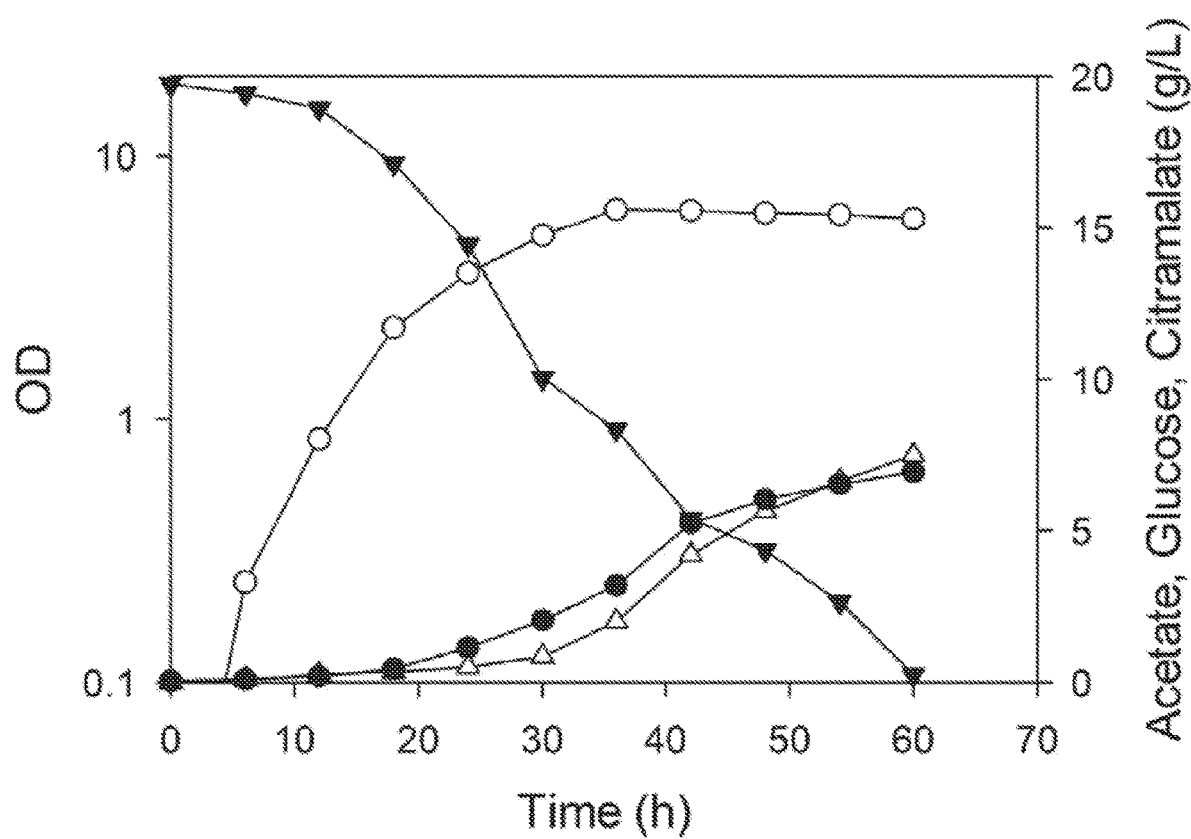
FIG. 4 shows citramalate production in a batch fermentation using MEC490/pZE12-cimA: OD (○), citramalate (●), glucose (Y), and acetate (Δ).
Figure 5:
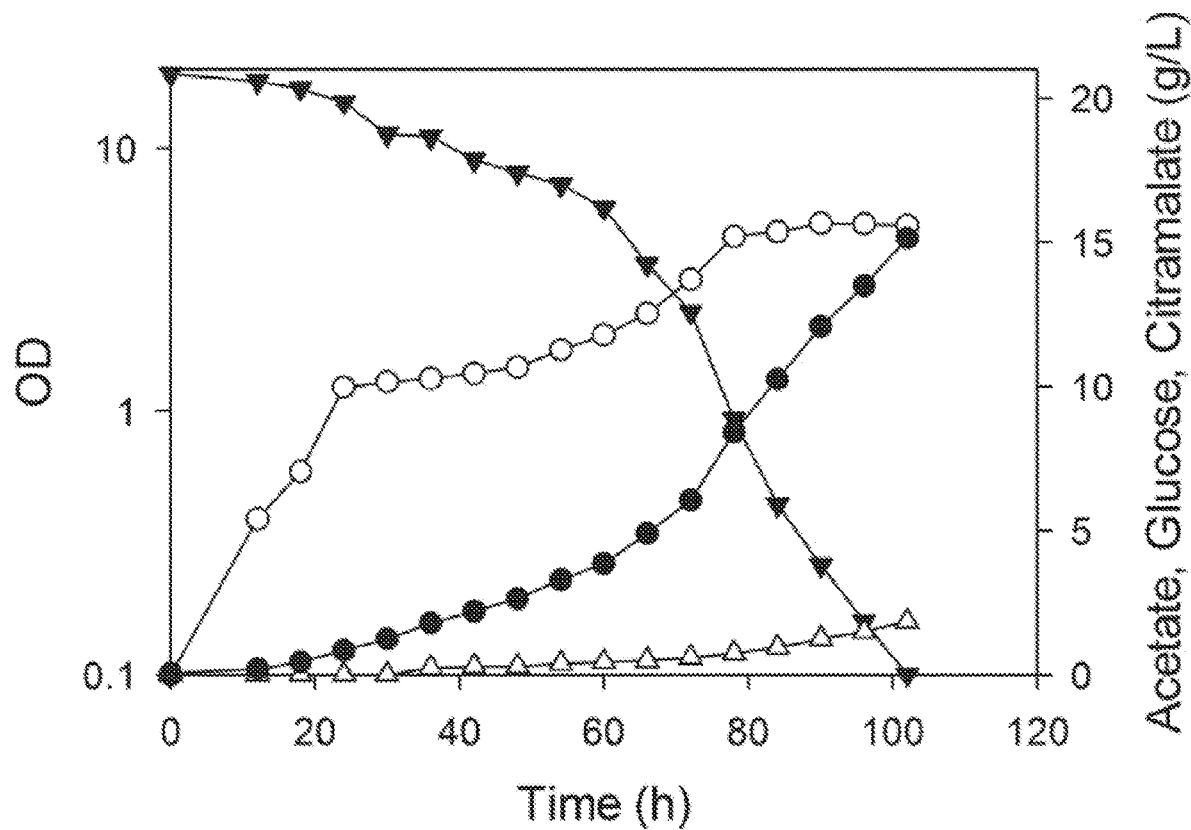
FIG. 5 shows citramalate production in a batch fermentation using MEC499/pZE12-cimA: OD (○), citramalate (●), glucose (▼), and acetate (Δ).

We next compared citramalate production by MG1655, MEC490, or MEC499 expressing citramalate synthase in duplicate under controlled batch conditions using a defined medium composed of 20 g/L glucose. The media additionally contained 2 g/L L-glutamate (for the gltA knockout) and 1 g/L L-leucine (leuC/leuD). MG1655/pZE12-cimA reached an OD of 8.3 in only 18 h, and in 30 h accumulated 4.9 g/L citramalate with no detectable acetate (FIG. 3). During exponential growth, the citramalate synthase activity was 21 IU/g DCW, and the intracellular acetyl-CoA concentration was 39 µg/g DCW. MEC490/pZE12-cimA reached an OD of 6.3 in 36 h, and accumulated 6.9 g/L citramalate and 7.5 g/L acetate in 60 h (FIG. 4). During exponential growth, the citramalate synthase activity was 20 IU/g, and the intracellular acetyl-CoA concentration was 46 µg/g. MEC499/pZE12-cimA reached an OD of 5.1 in 84 h and accumulated 14.8 g/L citramalate and 1.9 g/L acetate in 100 h (FIG. 5). During exponential growth, the citramalate synthase activity was 19 IU/g, and the intracellular acetyl-CoA concentration was 46 µg/g. During the growth of these strains, the potential byproducts of succinate, lactate, ethanol and pyruvate were not detected. Also, the results show that citramalate synthase expression was fortunately not affected by the E. coli strain genotype. The gltA ackA knockouts were critical to attaining a high concentration of citramalate, resulting in an increase citramalate yield on glucose threefold from 0.25 g/g (MG1655/pZE12-cimA) to 0.75 g/g (MEC499/pZE12-cimA).

Figure 6:
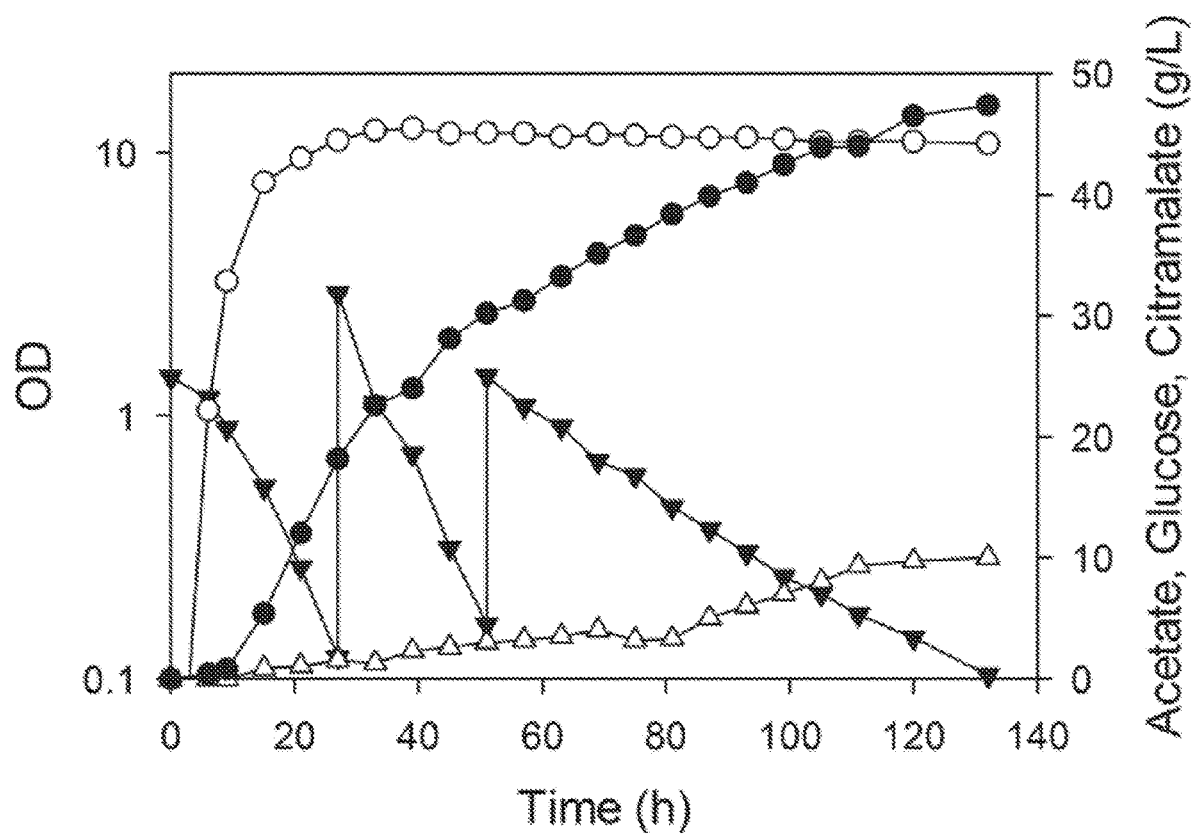
FIG. 6 shows citramalate production in a fed-batch fermentation using MEC499/pZE12-cimA: OD (○), citramalate (●), glucose (▼), and acetate (Δ). Approximately 30 g of glucose was added at 27 and 51 h.

Although the gltA and ackA gene deletions in MEC499 expressing citramalate synthase significantly increased citramalate yield, the ackA knockout also reduced growth rate by over 50% in the defined medium. A high level of intracellular acetyl-CoA might lead to the accumulation of NADH, which would affect glucose uptake by inhibiting the glyceraldehyde phosphate dehydrogenase (D'Alessio and Josse, 1971) and consequently decrease the rate of PEP synthesis. To overcome these potential growth deficiencies, we completed additional duplicate experiments in the fed-batch mode using a medium containing 15 g/L peptone as a complete source of amino acids (replacing L-leucine and L-glutamate addition). Additionally, approximately 30 g glucose was twice added to the fermenter when the glucose concentration decreased below 5 g/L. For these fed-batch processes the OD reached 9.0 within 21 h at which time the citramalate concentration was 12 g/L (FIG. 6). After 132 h, the final citramalate concentration reached an average of 46.5 g/L with a yield of 0.63 g/g glucose. Surprisingly, despite the ackA knockout, 10 g/L acetate was formed as byproduct.

Discussion

This study demonstrates that citramalate, a chemical precursor to the commodity chemical MAA, will accumulate by E. coli expressing citramalate synthase, an enzyme which forms the 5-carbon dicarboxylic acid directly from pyruvate and acetyl CoA as co-substrates. The key knockout necessary to facilitate acetyl CoA accumulation and hence optimal citramalate formation is the gltA gene coding citrate synthase. Since a gltA deletion prevents growth by the elimination of entry into the TCA cycle, necessary for generating precursors for biosynthesis (Neidhardt and Curtiss, 1996), glutamate was supplemented into the medium as a precursor of α-ketoglutarate. With this medium supplement cell growth was partially recovered in the gltA mutant.

Acetate was observed in several processes, particularly in the higher density cultures in the controlled bioreactor. The ackA deletion significantly reduced but not eliminate acetate production. Generally, acetyl CoA synthetase (coded by acs) is considered to be an acetate assimilation pathway (Lin et al., 2006), and is not initially suspected in the reverse formation of acetate from acetyl CoA. Phosphotransacetylase (or phosphate acetyltransferase) coded by pta converts acetyl CoA to acetyl-phosphate. Acetyl-phosphate can itself be used as a phosphate donor in the process of gene regulation and protein-dependent transportation systems (Hong et al., 1979; Wanner and Wilmes-Riesenberg, 1992). Since acetyl-phosphate can therefore result in acetic acid formation even in the absence of acetate kinase (ackA), an additional knockout target for improved citramalate formation and reduced acetate formation would be the pta gene.

Pyruvate oxidase (poxB) also might play a significant role in the aerobic growth of E. coli and in acetate formation (Abdel-Hamid et al., 2001). Typically, the Pta-AckA pathway operates during the growth phase, while the PoxB pathway functions during stationary phase (Dittrich et al., 2005). Moreover, PoxB would bypass acetyl CoA formation altogether. The prospect for PoxB involvement is supported by observations during the fed-batch process, over 80% of the acetate was formed after 30 h when cell growth had ceased, while pyruvate did not accumulate.

Acetate might also result from alternative anabolic pathways or from central carbon metabolism. Several metabolic reactions including acetylornithine deacetylase (ArgE), acetoacetyl-CoA transferases (AtoA and AtoD), cysteine synthases (CysM and CysK), UDP-3-O-acyl-Nacetylglucosamine deacetylase (LpxC), and N-acetylglucosamine-6-phosphate deacetylase (NagA) also generate acetate and could be more significant in a triple knockout strain. An interesting result is that the shake flask studies with MEC499 (MG1655 gltA leuC ackA) showed insignificant acetate formation, whereas the controlled, prolonged fed-batch process resulted in about 10 g/L acetate. Clearly, results in shake flasks are weak predictors of results in controlled processes.

In the fed-batch process, *E. coli* MEC499/pZE12-cimA produced nearly 50 g/L at a yield reaching over 75% of the theoretical maximum. This result suggests a hybrid biochemical-chemical route could provide a cost-effective approach to producing MAA using renewable resources. Further studies are underway to increase the performance of citramalate production by reducing acetate accumulation further and increasing the specific citramalate productivity under aerobic conditions.

REFERENCES

Abdel-Hamid, A. M., M. M. Attwood, and J. R. Guest. 2001. Pyruvate oxidase contributes to the aerobic growth efficiency of *Escherichia coli*. *Microbiology*. 147:1483-1498.

Atsumi, S., and J. C. Liao. 2008. Directed evolution of thermophilic citramalate synthase for 1-propanol and 1-butanol biosynthesis from *Escherichia coli*. *Appl. Environ. Microbiol* 74:7802-7808.

Arya, A. S., S. A. Lee, and M. A. Eiteman. 2013. Differential sensitivities of the growth of *Escherichia coli* to acrylate under aerobic and anaerobic conditions and its effect on product formation. *Biotechnol. Lett.* 35(11): 1839-1843.

Baba, T., T. Ara, M. Hasegawa, Y. Takai, Y. Okumura, M. Baba, K. A Datsenko, M. Tomita, B. L. Wanner, and H. Mori. 2006. Construction of *Escherichia coli* K-12 in-frame, single-gene knockout mutants: the Keio collection. *Mol. Syst. Biol.* 2:2006.0008.

Bauer, W. Jr. 2000. Methacrylic acid and derivatives. *Ullmann's Encyclopedia of Industrial Chemistry*. Wiley-VCH, Weinheim.

Buckel, W., and H. A. Barker. 1974. Two pathways of glutamate fermentation by anaerobic bacteria. *J. Bacteriol.* 117:1248-1260.

Bunch, P. K., F. Mat-Jan, N. Lee, and D. P. Clark. 1997. The ldhA gene encoding the fermentative lactate dehydrogenase of *Escherichia coli*. *Microbiol.* 143:187-195.

Carlsson, M., C. Habenicht, L. C. Kam, M. J. Antal Jr., N. Lian, R. J. Cunningham, M. Jones, Jr. 1994. Study of the sequential conversion of citric to itaconic to methylacrylic acid in near-critical and supercritical water. *Ind Eng. Chem. Res.* 33:1989-1996.

D'Alessio, G. and J. Josse. 1971. Glyceraldehyde phosphate dehydrogenase of *Escherichia coli*. *J. Biol. Chem.* 246: 4326-4333.

Datsenko, K. A. and B. L. Wanner. 2000. One-step inactivation of chromosomal genes in *Escherichia coli* K-12 using PCR products. *Proc. Natl. Acad. Sci. U.S.A* 97:6640-6645.

Diaz-Ricci, J. C., L. Regan, J. E. Bailey. 1991. Effect of alteration of the acetic acid synthesis pathway on the fermentation pattern of *Escherichia coli*. *Biotechnol. Bioeng.* 38:1318-1324.

Dittrich, C. R., G. N. Bennett, and K. Y. San. Characterization of the acetate-producing pathways in *Escherichia coli*. 2005. Biotechnol. Prog. 21:1062-1067.

Eikmanns, B., N. Thum-Schmitz, L. Eggeling, K. Liidtke, and H. Sahm. 1994. Nucleotide sequence, expression and transcriptional analysis of the *Corynebacterium glutamicum* gltA gene encoding citrate synthase. Microbiology. 140:1817-1828.

Eiteman, M. A. and M. J. Chastain. 1997. Optimization of the ion-exchange analysis of organic acids from fermentation. *Anal. Chim. Acta.* 338:69-75.

Feng, X., K. H. Tang, R. E. Blankenship, and Y. J. Tang. 2010. Metabolic flux analysis of the mixotrophic metabolisms in the green sulfur bacterium *Chlorobaculum tepidum*. *J. Biol. Chem.* 285:39544-39550.

Fultz, P. N. and J. Kemper. 1981. Wild-type isopropylmalate isomerase in *Salmonella typhimurium* is composed of two different subunits. *J. Bacteriol.* 148:210-219.

Fultz, P. N., D. Y. Kwoh, and J. Kemper. 1979. *Salmonella typhimurium* newD and *Escherichia coli* leuC genes code for a functional isopropylmalate isomerase in *Salmonella typhimurium-Escherichia coli* hybrids. *J. Bacteriol.* 137: 1253-1262.

Gao, L., W. Chiou, H. Tang, X. Cheng, H. S. Camp, and D. J. Burns. 2007. Simultaneous quantification of malonyl-CoA and several other short-chain acyl-CoAs in animal tissues by ion-pairing reversed-phase HPLC/MS. *J. Chromatogr. B.* 853:303-313.

Hong, J. S., A. G. Hunt, P. S. Masters, and M. A. Lieberman. 1979. Requirement of Acetyl Phosphate for the Binding Protein-Dependent Transport Systems in *Escherichia coli*. *Proc. Natl. Acad. Sci. U.S.A.* 76:1213-1217.

Howell, D. M., H. Xu, and R. H. White. 1999. (R)-Citramalate synthase in *Methanogenic archaea*. *J. Bacteriol.* 181:331-333.

Johnson, D. W., G. R. Eastham, M. Poliakoff, and T. A. Huddle. 2015. Method of producing acrylic and methacrylic acid. U.S. Pat. No. 8,933,179 B2.

Koser, S. A. 1924. Correlation of citrate utilization by members of the colon-aerogenes group with other differential characteristics and with habitat. *J. Bacteriol.* 9:59-77.

Lee, J., A. Goel, M. M. Ataai, and M. M. Domach. 1994. Flux adaptations of citrate synthase-deficient *Escherichia coli*. *Ann. N. Y. Acad. Sci.* 745:35-50.

Lee, T.-Y., K. Makino, H. Shinagawa, and A. Nakata. 1990. Overproduction of acetate kinase activates the phosphate regulon in the absence of the phoR and phoM functions in *Escherichia coli*. *J. Bacteriol.* 172:2245-2249.

Lichtenthaler, H. K., J. Schwender, A. Disch, and M. Rohmer. 1997. Biosynthesis of isoprenoids in higher plant chloroplasts proceeds via a mevalonate-independent pathway. *FEBS Lett.* 400:271-274.

Lin, H., N. M. Castro, G. N. Bennett, and K. Y. San. 2006. Acetyl-CoA synthetase overexpression in *Escherichia coli* demonstrates more efficient acetate assimilation and lower acetate accumulation: a potential tool in metabolic engineering. *Appl. Microbiol. Biotechnol.* 71:870-874.

Lutz, R. and H. Bujard. 1997. Independent and tight regulation of transcriptional units in *Escherichia coli* via the LacR/O, the TetR/O and AraC/I1-I2 regulatory elements. *Nucleic. Acids. Res.* 25:1203-1210.

Matsuyama, A., H. Yamamoto-Otake, J. Hewitt, R. T. A. MacGillivray, and E. Nakano. 1994. Nucleotide sequence of the phosphotransacetylase gene of *Escherichia coli* strain K12. *Biochim. Biophys. Acta.* 1219:559-562.

Molina, I., M. T. Pellicer, J. Badia, J. Aguilar, and L. Baldoma. 1994. Molecular characterization of *Escherichia coli* malate synthase G. Differentiation with the malate synthase A isoenzyme. *Eur. J. Biochem.* 224:541-8.

Nagai, K. 2001. New developments in the production of methyl methacrylate. *Appl. Catal. A-Gen.* 221:367-377.

Nakamura, J., S. Hirano, H. Ito, and M. Wachi. 2007. Mutations of the *Corynebacterium glutamicum*

NCgl1221 gene, encoding a mechanosensitive channel homolog, induce L-glutamic acid production. *Appl. Environ. Microbiol.* 73:4491-4498.

Nakamura, C. E. and G. M. Whited. 2003. Metabolic engineering for the microbial production of 1,3-propanediol. *Curr. Opin. Biotech.* 14:454-459.

Neidhardt F C, Curtiss R. 1996. *Escherichia coli* and *Salmonella*: Cellular and molecular biology. ASM Press. Washington, D.C.

Neidhardt, F. C. and R. Curtiss. 1996. *Escherichia coli* and *Salmonella*: Cellular and molecular biology. ASM Press. Washington, D.C.

Ornston L. N. and M. K. Ornston. 1969. Regulation of glyoxylate metabolism in *Escherichia coli* K-12. *J. Bacteriol.* 98:1098-108.

Porro D., M. M. Bianchi, L. Brambilla, R. Menghini, D. Bolzani, V. Carrera, J. Lievense, C. L. Liu, B. M. Ranzi, L. Frontali, and L. Alberghina. 1999. Replacement of a metabolic pathway for large-scale production of lactic acid from engineered yeasts. *Appl. Environ. Microbiol.* 65:4211-4215.

Risso C., S. J. Van Dien, A. Orloff, D. R. Lovley, and M. V. Coppi. 2008. Elucidation of an alternate isoleucine biosynthesis pathway in *Geobacter sulfurreducens*. *J. Bacteriol.* 190:2266-2274.

Salkind, M., E. H. Riddle, and R. W. Keefer. 1959. Acrylates and methacrylates—raw materials, intermediates, and plant integration. *Ind. Eng. Chem.* 51:1232-1238.

Sanchez, A. M., G. N. Bennett, and K. Y. San. 2005. Novel pathway engineering design of the anaerobic central metabolic pathway in *Escherichia coli* to increase succinate yield and productivity. *Metab. Eng.* 7:229-239.

Todd, J. D., A. R. J. Curson, M. J. Sullivan, M. Kirkwood, A. W. B. Johnston. 2012. The *Ruegeria pomeroyi* acuI gene has a role in DMSP catabolism and resembles yhdH of *E. coli* and other bacteria in conferring resistance to acrylate. *PLoS. ONE.* 7:e35947.

Vemuri, G. N., M. A. Eiteman, and E. Altman. 2001. Succinate production in dual-phase *Escherichia coli* fermentations depends on the time of transition from aerobic to anaerobic conditions. *J. Ind. Microbiol. Biotechnol.* 28:325-332.

Wanner, B. L. and M. R. Wilmes-Riesenberg. 1992. Involvement of phosphotransacetylase, acetate kinase, and acetyl phosphate synthesis in control of the phosphate regulon in *Escherichia coli*. *J. Bacteriol.* 174:2124-2130.

Yang, H. L. and D. P. Kessler. 1974. Genetic analysis of the leucine region in *Escherichia coli* b/r: gene-enzyme assignments. *J. Bacteriol.* 117:63-72.

Yim, H., R. Haselbeck, W. Niu, C. Pujol-Baxley, A. Burgard, J. Boldt, J. Khandurina, J. D. Trawick, R. E. Osterhout, R. Stephen, J. Estadilla, S. Teisan, H. B. Schreyer, S. Andrae, T. H. Yang, S. Y. Lee, M. J. Burk, and S. V. Dien. 2011. Metabolic engineering of *Escherichia coli* for direct production of 1,4-butanediol. *Nat. Chem. Biol.* 7:445-452.

Zhang, K., A. P. Woodruff, M. Xiong, J. Zhou, Y. K. Dhande. 2011. A synthetic metabolic pathway for production of the platform chemical isobutyric acid. *ChemSusChem*, 4(8): 1068-1070.

Example 2

Eliminating Acetate Formation Improves Citramalate Production by Metabolically Engineered *Escherichia coli*

Abstract

Background: Citramalate, a chemical precursor to the industrially important methacrylic acid (MAA), can be synthesized using *Escherichia coli* overexpressing citramalate synthase (cimA gene). Deletion of gltA encoding citrate synthase and leuC encoding 3-isopropylmalate dehydratase were helpful in achieving high citramalate yields. Acetate is an undesirable by-product potentially formed from pyruvate and acetyl-CoA, the precursors of citramalate during aerobic growth of *E. coli*. This study investigated strategies to minimize acetate and maximize citramalate production in *Escherichia coli* mutants expressing the cimA gene.

Results: Key knockouts that minimized acetate formation included acetate kinase (ackA), phosphotransacetylase (pta), and in particular pyruvate oxidase (poxB). Deletion of glucose 6-phosphate dehydrogenase (zwf) and ATP synthase (atpFH) aimed at improving glycolytic flux negatively impacted cell growth and citramalate accumulation in shake flasks. In a repetitive fed-batch process, *E. coli* gltA leuC ackA-pta poxB overexpressing cimA generated 54.1 g/L citramalate with a yield of 0.64 g/g glucose (78% of theoretical maximum yield), and only 1.4 g/L acetate in 87 h.

Conclusions: This study identified gene deletions helpful in reducing acetate accumulation during aerobic growth and citramalate production in metabolically engineered *E. coli* strains. The citramalate yield and final titer relative to acetate at the end of the fed-batch process are the highest reported to date.

Background

Synthetic biology and metabolic engineering have enabled sustainable and eco-friendly manufacturing of commercially important food products, pharmaceuticals, commodity chemicals, and other high value products using microorganisms. Some chemicals which cannot be synthesized exclusively by a biosynthetic route might be generated using hybrid approaches involving both biological and chemical synthesis. For example, methacrylic acid (MAA), a commodity chemical with an estimated annual global market of 2.2 million tons (Zhang et al., 2011) is a monomer of poly(methyl methacrylate) or PMMA, which is used in automobile, construction, medical device, lighting and the home appliance industries. Acrylates in general are very toxic (Arya et al., 2013), and their direct microbial synthesis at relevant concentrations seems unlikely. MAA can fortunately be synthesized via a hybrid route: biochemical production of citramalate from glucose (Example 1), and subsequently transforming this compound chemically using base-catalyzed decarboxylation and dehydration (Johnson et al., 2012). Citramalate (or citramalic acid) is naturally found in the metabolic pathways of some anaerobic bacteria (Buckel and Barker, 1974; Risso et al., 2008; Feng et al., 2009).

*Escherichia coli* is a well-established microbial cell factory for the biotechnology industry. Citramalate production in metabolically engineered *E. coli* expressing citramalate synthase coding the cimA gene (FIG. 7) has previously been demonstrated (Atsumi et al., 2008; Example 1). In a recent study, *E. coli* MG1655 gltA leuC ackA/pZE12-cimA containing three key knockouts (citrate synthase, 3-isopropylmalate dehydratase and acetate kinase) accumulated 46 g/L citramalate from glucose at a yield of 0.63 g/g (75% of the theoretical maximum). However, 10 g/L acetate also accumulated despite the deletion of acetate kinase. Acetate is a typical "overflow" metabolite when wild-type *E. coli* cells are grown at a high growth rate, and the carbon flux into central metabolic pathways exceeds the cells' biosynthetic demands and the capacity for energy generation (Akesson et al., 1999; Eiteman and Altman, 2006). Acetate formation is undesirable because this acid: (i) negatively impacts cell growth even at concentrations as low as 0.5 g/L (Nakano et al., 1997); (ii) is a sink which diverts carbon that could otherwise be used to synthesize the desired product (Eiteman and Altman, 2006); (iii) necessitates additional downstream separation step(s) that add to process costs. Acetate is generated by two pathways in *E. coli*: from acetyl-CoA via acetate kinase and phosphotransacetylase (ackA and pta genes), and from pyruvate via pyruvate oxidase (poxB). While the ackA-pta pathway is typically the route during exponential growth, pyruvate oxidase becomes active during late exponential and early stationary phases (Dittrich et al., 2005). Deletion of ackA and/or pta genes has previously resulted in lower growth rates and lower but still significant acetate accumulation in several *E. coli* mutants (Diaz-Ricchi et al., 1991; Contiero et al., 2000; Causey et al., 2003; Dittrich et al., 2005). Strains with poxB deleted but not the ackA-pta pathway accumulated either similar or slightly lower acetate compared to wild type strains (Dittrich et al., 2005; Li et al., 2007). Growth of strains in which both acetate producing pathways were deleted showed very low acetate accumulation and growth rates similar to wild type strains (Causey et al., 2003; Dittrich et al., 2005).

The two precursors for citramalate, pyruvate and acetyl-CoA, are generated through the glycolytic pathway, and increasing the flux through glycolysis might improve citramalate productivity and yield. Since the ATP/ADP ratio controls glycolysis (Koebmann et al., 2002), previous research has shown that decreasing ATP generation increased the rate of glycolysis (Noda et al., 2006), and product formation (Zhu et al., 2008; Semkiv et al., 2014). Glycolytic flux may also be improved by preventing flux through the pentose phosphate pathway (PP pathway), for example, by a deletion in glucose 6-phosphate dehydrogenase (zwf) (Zhao et al., 2004).

The goal of this study was to improve the formation of citramalate in *E. coli* expressing citramalate synthase by blocking acetate formation. We also investigated whether strategies to increase glycolytic flux would increase citramalate yield and productivity.

Results

Citramalate and Acetate Formation in Shake Flasks

Figure 8:
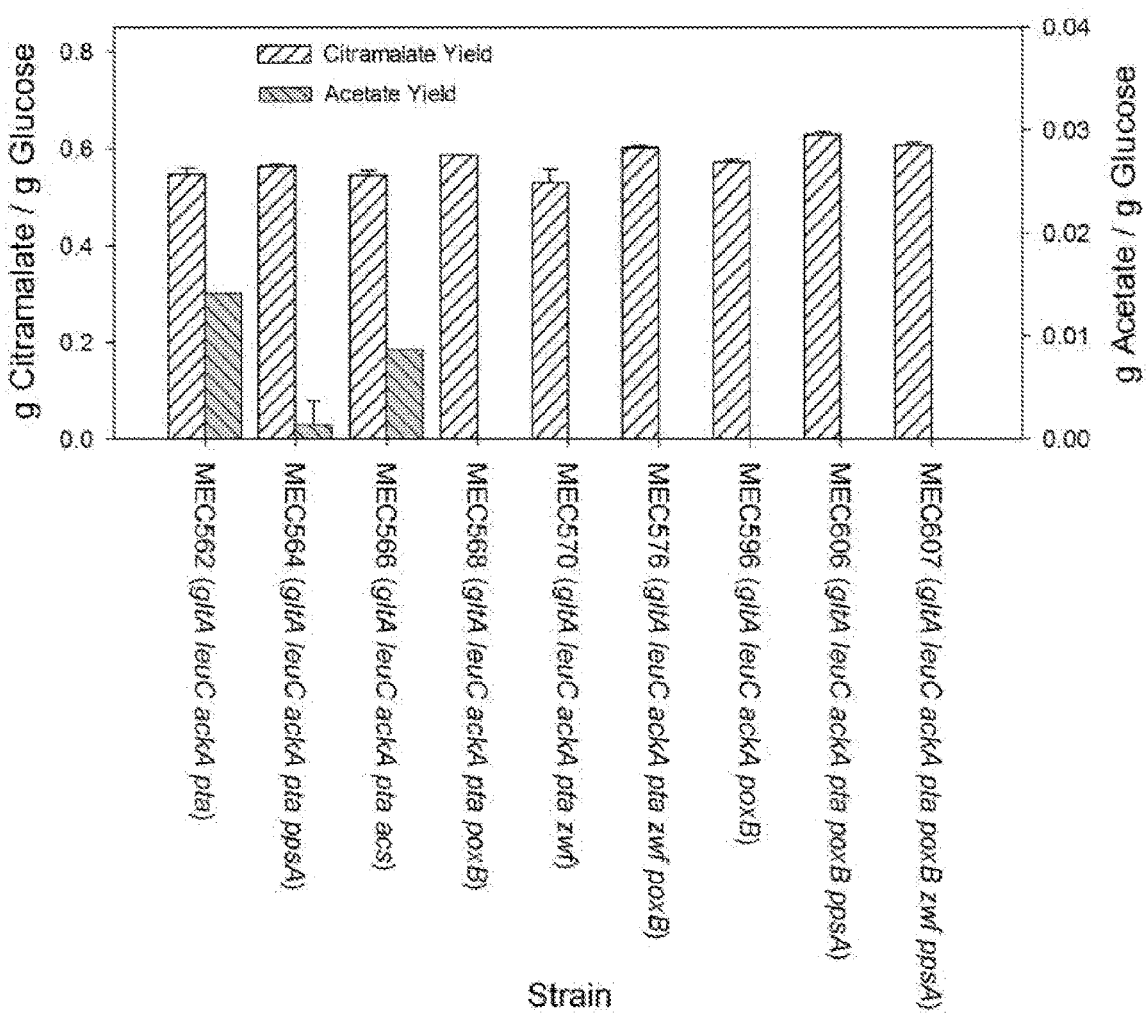
FIG. 8 shows comparison of citramalate and acetate yields at 24 h in shake flasks using various *E. coli* strains expressing cimA gene. The defined medium contained 5 g/L glucose, 1 g/L L-glutamate and 0.2 g/L L-leucine. All studies were carried out in triplicate.

Citramalate synthase (coded by the cimA gene) mediates the conversion of pyruvate and acetyl-CoA to citramalate. Knockouts in the gltA, leuC and ackA genes coding for citrate synthase, 3-isopropylmalate dehydratase, and acetate kinase, respectively, were helpful in achieving high citramalate yield (Example 1). Despite the deletion of acetate kinase, over 10 g/L acetate accumulated in a repetitive fed-batch process (Example 1). We therefore compared citramalate formation after 24 h in shake flasks by several *E. coli* strains having additional gene knockouts and expressing the pZE12-cimA plasmid (FIG. 8). Specifically, we examined the enzymes involved in acetate formation from acetyl-CoA and pyruvate, the precursors of citramalate.

In *E. coli* phosphotransacetylase (pta gene) and acetate kinase (ackA) normally produce acetate during the exponential growth phase through the high energy acetyl phosphate (acetyl-P) intermediate (Rose et al, 1954). Previous research demonstrated that acetyl-P can form acetate even in the absence of ackA (Wanner and Wilmes-Reisenberg, 1992). Since a ackA deletion alone was previously insufficient to prevent acetate formation (Example 1), we suspected acetyl-P generated via phosphotransacetylase might be responsible for acetate formation. From 5.0 g/L glucose, MEC562/pZE12-cimA (gltA leuC ackA-pta) attained an OD of 2.70 and accumulated 2.72 g/L citramalate and 0.07 g/L acetate, similar to the amount of these products observed previously in shake flasks using MG1655 gltA leuC ackA (Example 1). The combination of pta and ackA also did not eliminate acetate formation.

Phosphoenolpyruvate synthase (ppsA) catalyzes the ATP-dependent conversion of pyruvate to phosphoenolpyruvate (Berman and Cohn, 1970). A loss of pyruvate through this enzyme could affect citramalate accumulation. However, MEC564/pZE12-cimA (gltA leuC ackA-pta ppsA) generated 2.76 g/L citramalate and 0.01 g/L acetate, demonstrating that phosphoenolpyruvate synthase does not impact citramalate formation, and surprisingly its absence may reduce acetate formation.

Acetyl-CoA synthetase (acs) is described as an acetate scavenging enzyme that typically converts acetate to acetyl-CoA (Brown et al, 1977). To rule out possible reverse formation of acetate via this enzyme, we constructed MEC566/pZE12-cimA (gltA leuC ackA-pta acs) containing the additional knockout in acs gene. MEC566/pZE12-cimA generated 1.9 g/L citramalate and 0.03 g/L acetate. Because the three knockouts ackA-pta acs do not eliminate acetate formation, acetate is likely derived from another metabolite and not acetyl CoA. Moreover, the OD at 24 h was 30% lower for MEC566/pZE12-cimA compared to MEC562/pZE12-cimA.

Membrane-bound pyruvate oxidase (poxB) is coupled to the respiratory chain, and oxidizes pyruvate directly to acetate, by-passing acetyl-CoA formation. MEC568/pZE12-cimA (gltA leuC ackA-pta poxB) generated 2.9 g/L citramalate, and no acetate was detected. To address whether pyruvate oxidase or phosphotransacetylase was the more important route to acetate formation, we also examined the performance of the strain retaining the native phosphotransacetylase activity. MEC596/pZE12-cimA (gltA leuC ackA poxB) generated 2.41 g/L citramalate, and no acetate was detected. These results suggest that pyruvate oxidase plays the more important role in acetate formation. MEC596/pZE12-cimA also had 20% lower 24 h OD compared to MEC568/pZE12-cimA. MEC606/pZE12-cimA (gltA leuC ackA-pta poxB ppsA) accumulated only 2.14 g/L citramalate but no acetate, and grew to an OD of 1.92, nearly 30% lower than MEC562/pZE12-cimA. In summary, the combination of pta and poxB knockouts appears to be most effective in providing high citramalate yield and preventing acetate formation.

Several other strains were examined which were anticipated to benefit citramalate formation, though not affect acetate generation directly. Glucose-6P dehydrogenase (zwf) diverts metabolic flux at glucose-6P from glycolysis into the pentose phosphate pathway, which not only reduces glycolytic flux, but also lowers the yield of pyruvate and acetyl-CoA (Zhao et al., 2004). To examine the impact of this pathway on citramalate formation, three strains containing the zwf gene deletion were constructed. Each of these strains having the additional zwf deletion showed slightly lower citramalate yields. However, because they consistently grew much slower than the corresponding strain containing the zwf gene, the final citramalate concentrations were much lower (1.31-1.74 g/L).

Previous results have demonstrated that lowering the cellular ATP level increases glycolytic flux (Koebmann et al., 2002; Noda et al., 2006), increases ethanol yield in yeast (Semkiv et al., 2014), and increases pyruvate yield in recombinant *E. coli* (Zhu et al., 2008). However, MEC638/pZE12-cimA (gltA leuC ackA-pta poxB atpFH) were unable to grow in the glucose/glutamate/leucine defined medium.

Citramalate and Acetate Formation in Bioreactors

Results from screening strains in shake flasks do not necessarily transfer to a bioreactor which operates under different environmental conditions (mixing, oxygenation, pH control, etc.). We therefore selected a few strains based on encouraging shake flask results for studies at the larger scale. The poxB knockout appeared important for the elimination of acetate, while several other single or combinations of gene deletions severely reduced growth. To confirm the importance of poxB and more carefully observe differences in growth rate and productivity, we selected MEC562/pZE12-cimA (gltA leuC ackA-pta), MEC568/pZE12-cimA (gltA leuC ackA-pta poxB) and MEC606/pZE12-cimA (gltA leuC ackA-pta poxB ppsA) for controlled batch studies.

Figure 9:
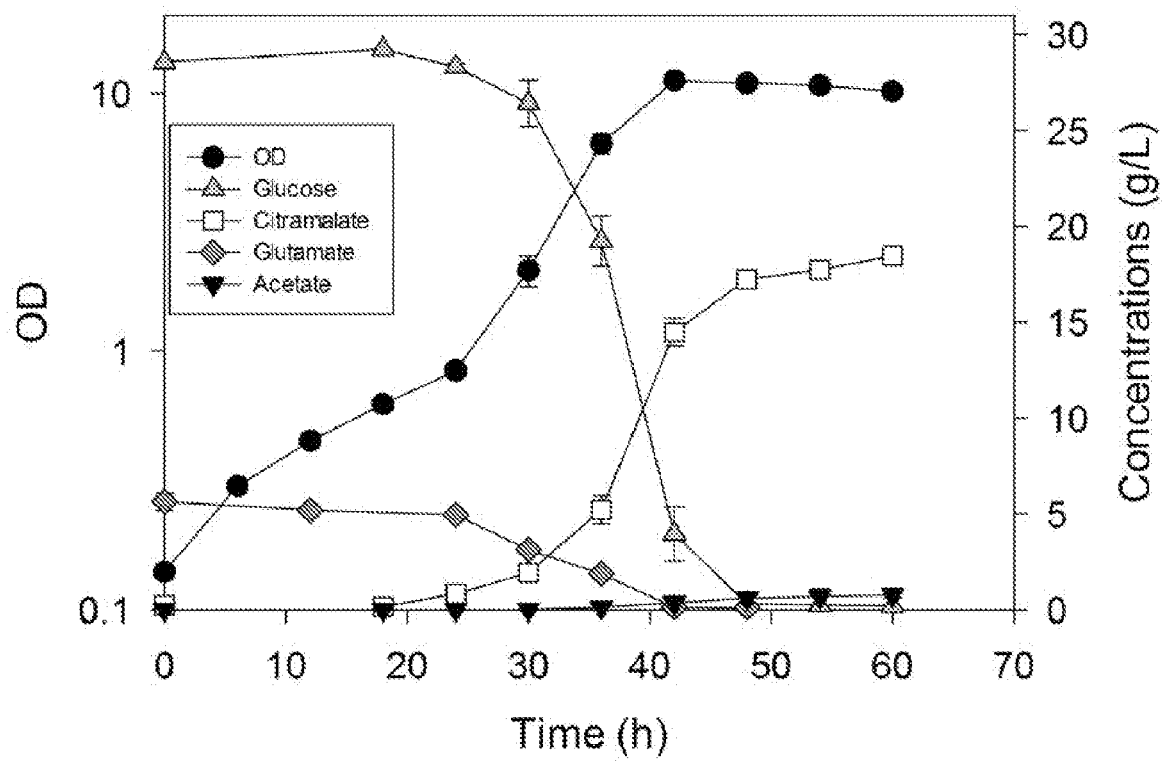
FIG. 9 shows time course of citramalate production by *E. coli* MEC562/pZE12-cimA (gltA leuC ackA-pta) in duplicate batch culture. The defined medium contained 30 g/L glucose, 5 g/L L-glutamate and 1.0 g/L L-leucine.
Figure 10:
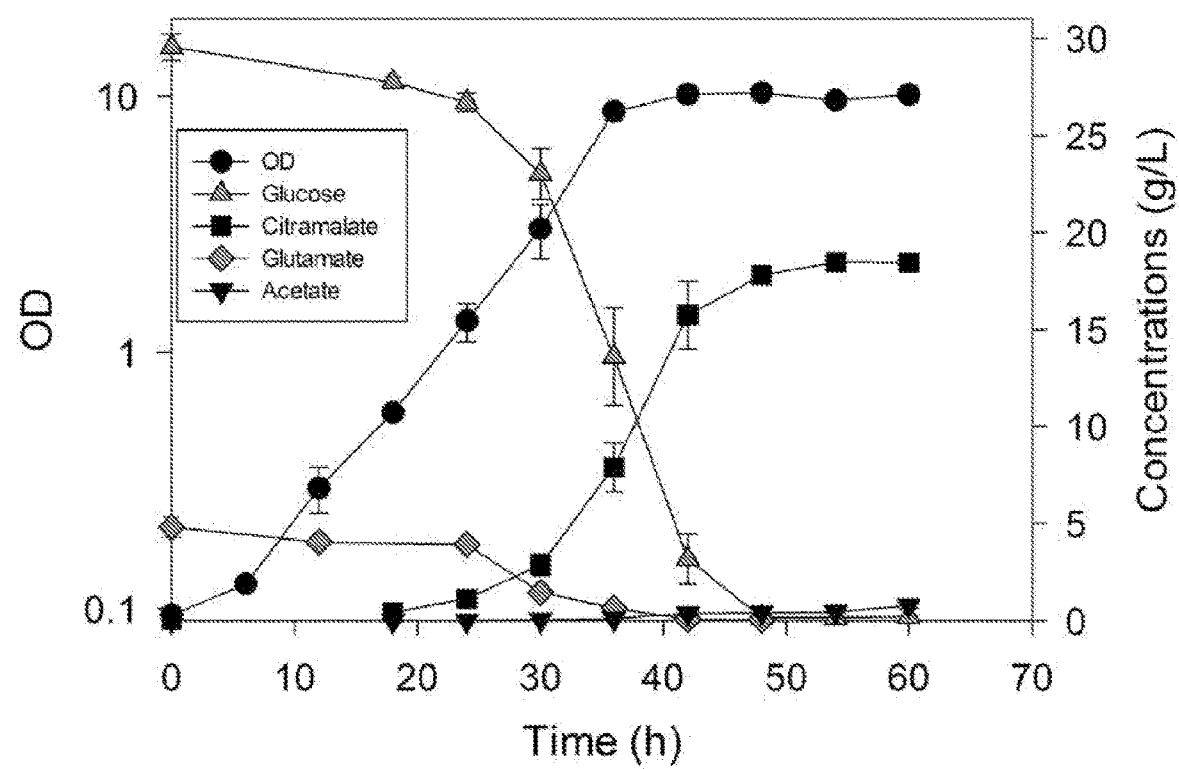
FIG. 10 shows time course of citramalate production by *E. coli* MEC568/pZE12-cimA (gltA leuC ackA-pta poxB) in duplicate batch culture. The defined medium contained 30 g/L glucose, 5 g/L L-glutamate and 1.0 g/L L-leucine.
Figure 11:
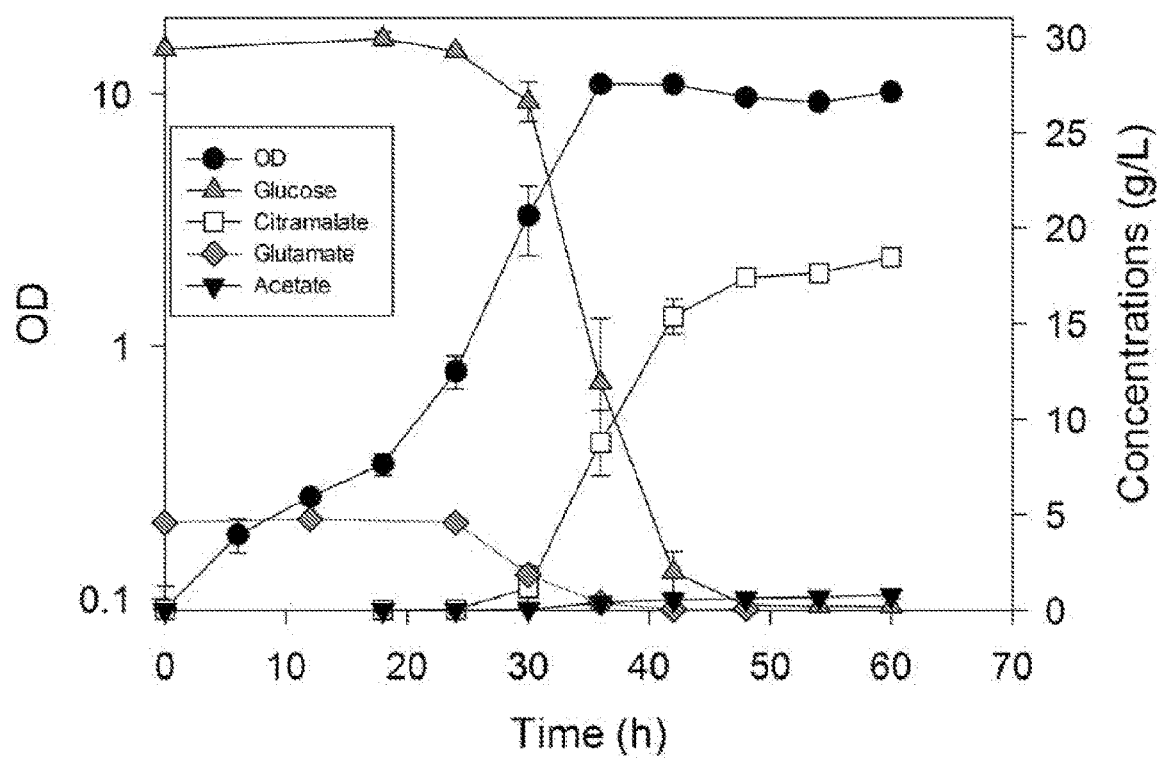
FIG. 11 shows time course of citramalate production by *E. coli* MEC606/pZE12-cimA (gltA leuC ackA-pta poxB ppsA) in duplicate batch culture. The defined medium contained 30 g/L glucose, 5 g/L L-glutamate and 1.0 g/L L-leucine.

In duplicate experiments using nominally 30 g/L glucose, MEC562/pZE12-cimA reached an OD of 11.2 in 42 h, and accumulated 18.5 g/L (±0.2) citramalate and 0.78 g/L (±0.11) acetate in 60 h (FIG. 9). During the exponential phase, the citramalate synthase enzyme activity was 36.6 IU/g DCW. MEC568/pZE12-cimA reached an OD of 10.3 in 48 h, and accumulated 18.5 g/L (±0.3) citramalate and 0.45 g/L (±0.07) acetate in 54 h (FIG. 10). The citramalate synthase activity was 31.6 IU/g DCW during the exponential phase. MEC606/pZE12-cimA reached an OD of 10.9 in 42 h, and accumulated 17.6 g/L (±0.2) citramalate and 0.68 g/L (±0.04) acetate in 54 h (FIG. 11). The citramalate synthase activity during the exponential phase was 40.2 IU/g DCW. The citramalate yield from glucose for each of these three strains was 0.60-0.65 g/g, and did not statistically differ. Other potential by-products including succinate, lactate, ethanol, and pyruvate were not detected (<0.02 g/L).

MEC568/pZE12-cimA having knockouts in pta, ackA and poxB genes generated the least acetate in batch experiments. We therefore chose this strain for a repetitive fed-batch process. Specifically, the process commenced as a batch process, and the glucose concentration was monitored. When the glucose concentration decreased to below 5 g/L, an additional 20 g glucose, 5 g L-glutamate and 1 g L-leucine were added. This batch-wise nutrient feed was accomplished 4 times during the course of the study, and the OD achieved by the cells after 87 h was 20.5. At this time the citramalate concentration was 54.1 g/L, and the yield on glucose was 0.64 g/g, while the acetate concentration was only 1.4 g/L. Citramalate synthase activity decreased from 35 IU/g DCW at 39 h to 12 IU/g DCW at 87 h.

Discussion

In this study, citramalate at a high final concentration (54.1 g/L) and yield (0.64 g/g) was formed in an *E. coli* cell factory overexpressing citramalate synthase (cimA) gene. We observed over 85% less acetate and a greater citramalate yield compared to a recent study (Example 1). This reduction in acetate accumulation was accomplished by knocking out the ackA-pta and poxB genes, coding for the two major acetate production pathways in *E. coli*. Some acetate (less than 2 g/L) was still observed during batch and fed-batch fermentation processes in the strains containing ackA-pta and poxB gene deletions (MEC568/pZE12-cimA and MEC606/pZE12-cimA). In a previous study, 1.7 g/L acetate was also reported in an ackA-pta and poxB triple mutant *E. coli* strain (Phue et al., 2010). In all cases, most acetate accumulation in these triple knockouts occurred in the late exponential and stationary phases. This observation suggests that acetate formation is activated in ackA-pta poxB strains only when cells are under stress during late exponential and stationary phases, perhaps when a portion of the cellular components are being degraded. Many catabolic reactions generate acetate, and some anabolic pathways including N-acetylglucosamine-6-phosphate deacetylase (nagA gene), UDP-3-O-acyl-N-acetylglucosamine deacetylase (lpxC), acetylornithine deacetylase (argE), cysteine synthases (cysM and cysK), and acetoacetyl-CoA transferases (atoA and atoD) pathways might also contribute to acetate accumulation (Phue et al., 2010).

One strategy proposed to reduce acetate accumulation is the overexpression of the acetate scavenging acetyl-CoA synthetase (acs) (Lin et al., 2006). This pathway helps accumulate acetyl-CoA and hence could benefit citramalate production. Since the saturation of respiratory capacity and resultant increase in the NADH/NAD+ ratio are also known to drive metabolism towards acetate generation (Vemuri et al., 2006a; De Mey et al., 2007), efforts to decrease NADH generation may prove useful. For example, expression of NADH oxidase in an *E. coli* arcA mutant eliminated acetate formation at high growth rates (Vemuri et al., 2006a,b). Nevertheless, the complete elimination of acetate while achieving high yield for another product is a challenging problem because it requires a multigene approach and detailed attention to futile pathways, anaplerotic pathways, precursor levels, coenzyme levels, and redox ratios (De Mey et al., 2007). A comprehensive understanding of the impact of genetic interventions on the metabolic flux distribution through modeling and flux analysis might help fine tune these efforts.

Knocking out ackA-pta poxB might result in a greater intracellular accumulation of pyruvate and acetyl-CoA, the precursors of citramalate and hence improve the yield of this biochemical from glucose, though the yield was indistinguishable from the yield previously reported for MG1655 gltA leuC ackA expressing citramalate synthase (Example 1). Glycolysis and the PP pathway are the two major glucose catabolic pathways in *E. coli*, and NADH accumulation during glycolysis induces acetate formation via pyruvate oxidase (Vemuri et al., 2006a). Previously, poxB mutants have been observed to increase carbon flux through PP pathway by upregulating glucose 6-phosphate dehydrogenase (Li et al., 2007). In this study, our effort to decrease acetate formation by a knockout in the poxB gene may have led to the partial redirection of glucose into the PP pathway instead of glycolysis. If such a redirection occurred, any potential improvement in citramalate yield through increased availability of acetyl CoA might be compensated by the loss in yield resulting from the elevated PP pathway flux.

The PP pathway protects cells against oxidative stress by generating reducing equivalents as NADPH (Hua et al., 2003). *E. coli* strains blocked in the PP pathway, for example, by deleting the zwf gene, compensate for the loss in NADPH formation by increasing glucose uptake rate, increasing the activity of isocitrate dehydrogenase and increasing the TCA cycle flux (Zhao et al., 2004; Nicolas et al., 2007). Thus a zwf knockout may improve yields of products whose biosynthetic pathways involve glycolysis or TCA cycle metabolites. For instance, zwf gene deletion enhanced lycopene production by over 130% in recombinant *E. coli* strains, owing to an improved Emden-Meyerhof-Parnas (EMP) pathway flux and increased pyruvate (Zhou et al., 2013). In our shake flask studies, strains with zwf deletions resulted in lower growth and citramalate accumulation. Unlike previous studies of zwf strains, these strains also contained a gltA knockout that prevented carbon flow from acetyl CoA into the TCA cycle, and glutamate was supplied as a secondary carbon source. Thus, the cells were unable to respond to a block in the PP pathway by generating NADPH in the TCA cycle (i.e., isocitrate dehydrogenase), resulting in significantly reduced glucose uptake and growth rate. Growth and citramalate production in a zwf knockout might be improved by engineering another strategy to generate NADPH (Martinez et al., 2008).

We speculated that any intracellular pyruvate accumulation in the gltA strain might result in loss of carbon through PEP synthase, and preventing this loss by knocking out the ppsA gene could result in pyruvate accumulation. However, no significant benefit of a ppsA knockout on citramalate production was observed in the shake flask or batch reactor studies. Gluconeogenic genes are activated in *E. coli* during the metabolic switch from glucose to acetate consumption (Kao et al., 2005). Since the strains examined in this study exhausted glucose only at the end of the process and generated low concentrations of acetate, such a switch may not have been a factor, making ppsA irrelevant.

ATPase plays a major role in metabolic control, and mutations in ATP synthase increase glycolytic flux (Koebmann et al., 2002). Increased glycolytic flux normally leads to increased acetate excretion through acetate kinase as a means to replenish ATP through substrate level phosphorylation (Noda et al., 2006). Growth rate and growth yield are related to the rate of ATP synthesis and the amount of ATP synthesized per unit of substrate consumed (Jensen and Michelsen, 1992). In this study, the strain with the atpFH knockouts (MEC638) was unable to generate acetate as a consequence of the ackA-pta poxB knockouts, and with little metabolic flexibility, failed to grow in the glucose/glutamate/leucine medium.

Figure 12:
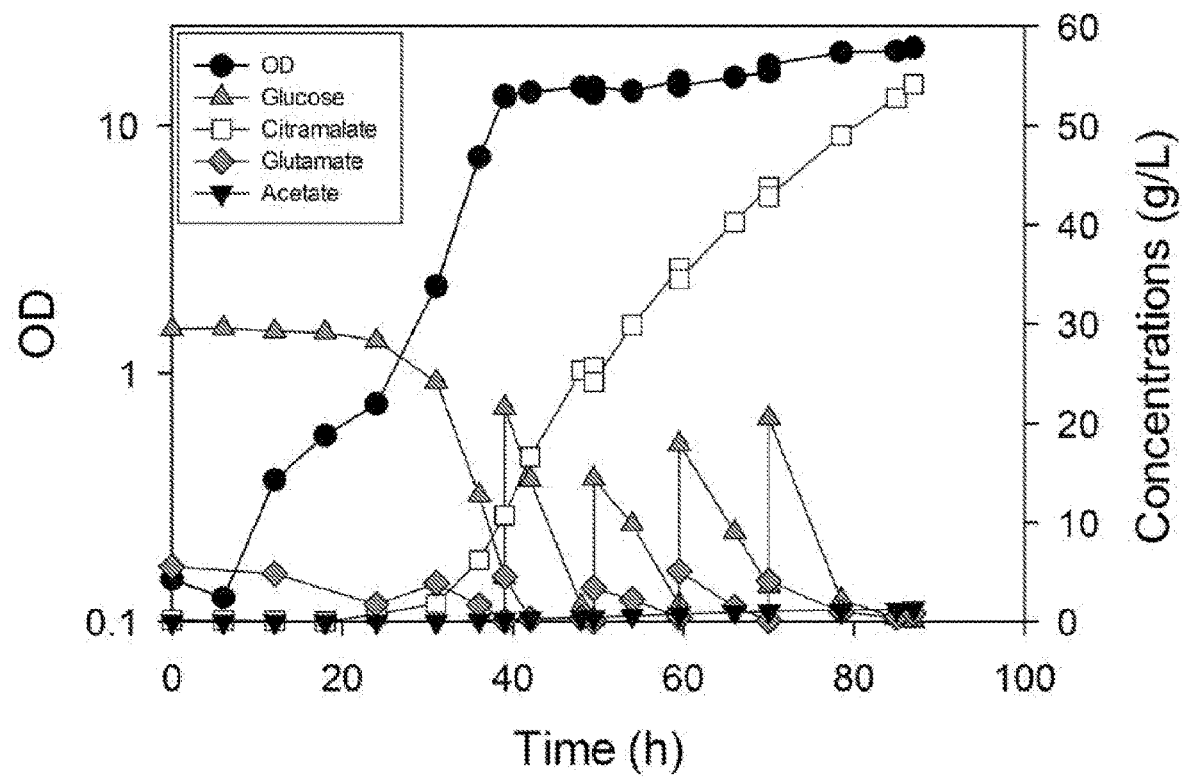
FIG. 12 shows time course of citramalate production by *E. coli* MEC568/pZE12-cimA (gltA leuC ackA-pta poxB) in fed-batch culture. The defined medium initially contained 30 g/L glucose, 5 g/L L-glutamate and 1.0 g/L L-leucine. When the glucose concentration decreased below 5 g/L, 20.0 g glucose, 5.0 g L-glutamate and 1.0 g L-leucine dissolved together in 35 mL DI water were added four times.

Potassium hydroxide (KOH) was used for pH control in the fermentation processes. At the end of the fed-batch process (FIG. 12), the concentration of $K^+$ ions estimated from the volume of base added to control the pH was 1.1 mol/L, while the $NH_4^+$ concentration was measured to be 188 mg/L. Previous research has demonstrated that the *E. coli* growth ceases at a $K^+$ concentration of 1.1 mol/L (Wu et al., 2014), so the current process may become limited in citramalate formation as a result of the counter-ion needed for pH control.

Conclusion

This study reports citramalate production at high yield with low acetate accumulation in metabolically engineered *E. coli* overexpressing citramalate synthase by a codon-optimized cimA gene. The key knockouts critical to minimizing acetate formation were identified as pta, ackA and poxB. Knockouts of zwf and atpFH genes, targeted at improving citramalate production by increasing the glycolytic flux and rate, did not show promising results in shake flask studies. Future work will be aimed at further exploring other metabolic and process engineering strategies to achieve higher titers of citramalate without requiring glutamate in the medium while eliminating acetate.

Methods

Strain Construction and Growth Media

Strains used in this study are listed in Table 2. The P1 phage method was used for transducing gene mutations into *E. coli* MG1655 from their respective strains in the KEIO collection (Baba et al., 2006). When necessary for additional gene deletions, a strain was cured of kanamycin using the pCP20 plasmid (Datsenko and Wanner, 2000). All constructs were confirmed using PCR. All strains were transformed with pZE12-cimA plasmid to express citramalate synthase (Example 1). Strains were routinely grown at 37° C. using Lysogeny Broth (LB). The composition of defined XC medium was (per L): 13.3 g $KH_2PO_4$, 4.0 g $(NH_4)_2HPO_4$, 8.4 mg $Na_2(EDTA).2H_2O$, 1.2 g $MgSO_4.7H_2O$, 4.5 mg thiamine.HCl, 13 mg $Zn(CH_3COO)_2.2H_2O$, 1.5 mg $CuCl_2.2H_2O$, 15.0 mg $MnCl_2.4H_2O$, 2.5 mg $CoCl_2.6H_2O$, 3.0 mg $H_3BO_3$, 2.5 mg $Na_2MoO_4.2H_2O$, 100 mg Fe(III) citrate, and 100.0 mg citric acid. Carbon sources were added as detailed below. Additionally, either medium was supplemented with 50.0 mg/L ampicillin and/or 100.0 mg/L kanamycin as appropriate.

TABLE 2

Strains used in this study.

| Strains | Genotype |
|---|---|
| MEC562 | MG1655 ΔgltA770::(FRT) ΔleuC778::(FRT) ΔackA778::(FRT) Δpta779::Kan |
| MEC563 | MG1655 ΔgltA770::(FRT) ΔleuC778::(FRT) ΔackA778-pta779::(FRT) |
| MEC564 | MEC563 ΔppsA776::Kan |
| MEC566 | MEC563 Δacs-763::Kan |
| MEC568 | MEC563 ΔpoxB772::Kan |
| MEC570 | MEC563 Δzwf777::Kan |
| MEC576 | MEC563 Δzwf777::(FRT) ΔpoxB772::Kan |
| MEC596 | MG1655 ΔgltA770::(FRT) ΔleuC778::(FRT) ΔackA778::(FRT) ΔpoxB772:Kan |
| MEC606 | MEC563 ΔpoxB772::(FRT) ΔppsA776::Kan |
| MEC607 | MEC563 ΔpoxB772::(FRT) Δzwf777::(FRT) ΔppsA776::Kan |
| MEC638 | MEC563 ΔpoxB772::(FRT) ΔatpFH::Kan |

Shake Flask and Bioreactor Studies

For shake flask studies, cells were first grown in 3 mL LB for 12-14 h, and then 0.5 mL transferred to 50 mL XC medium with 5.0 g/L glucose, 1.0 g/L L-glutamate and 0.2 g/L L-leucine in 500 mL shake flasks in triplicate. Each culture was induced at the time of inoculation with 0.2 mM IPTG. Cultures grew at 37° C. and 250 rpm (19 mm pitch) for 24 h.

All bioreactor studies were conducted in 2.5 L bioreactors (Bioflo 2000, New Brunswick Scientific Co., New Brunswick, N.J., USA). Cultures were again grown first in LB, then 50 mL shake flasks as described above, and which were then used to inoculate 1.0 L XC medium with 30.0 g/L glucose, 5.0 g/L L-glutamate and 1.0 g/L L-leucine. Each culture was induced at the time of inoculation with 0.2 mM IPTG. Agitation was maintained at 400 rpm and air supplemented with pure oxygen if necessary was sparged at 1.0 L/min to maintain the dissolved oxygen above 40% saturation. The pH was controlled at 7.0 using 20% (w/v) KOH, and the temperature was maintained at 37° C. For a fed-batch process, 20.0 g glucose, 5.0 g L-glutamate and 1.0 g L-leucine dissolved together in 35 mL DI water was added four times when the glucose concentration in the culture decreased below 5.0 g/L.

Analytical Methods

Optical density (OD) at 600 nm was measured using a spectrophotometer (UV-650 spectrophotometer, Beckman Instruments, San Jose, Calif., USA). Concentrations of extracellular organic acids were measured using HPLC with Refractive Index detection as described previously (Eiteman and Chastain, 1997). Glutamate concentration was measured using a glutamate assay kit (Sigma-Aldrich Co., St. Louis, Mo., USA). Ammonia-nitrogen ($NH_4$—N) was determined by the Feed and Environmental Water Lab (University of Georgia, Athens, Ga., USA) using the colorimetric EPA method (U.S. EPA, 1983).

Cell-free extracts were prepared according to the following procedure: (i) centrifuge sample at 3300×g for 10 min at 4° C.; (ii) wash the cell pellet twice with 100 mM Tris-HCl (pH 8.0) at 4° C.; (iii) resuspend in 100 mM Tris-HCl (pH 8.0) at 4° C.; (iv) lyse cells using a French® press (Thermospectronic, Rochester, N.Y., USA) at 14,000 psi with 2-3 passes; (v) remove cell debris by centrifugation at 20,000×g for 15 min at 4° C. Citramalate synthase enzyme activity was measured in the cell-free extracts following a previous protocol (Howell et al., 1999). Briefly, the rate of free CoA generated at 37° C. was determined by detecting its reaction product with 5,5'-Dithiobis(2-nitrobenzoic acid) at 412 nm.

REFERENCES

Akesson M, Karlsson E N, Hagander P, Axelsson J P, Tocaj A: On-line detection of acetate formation in *Escherichia coli* cultures using dissolved oxygen responses to feed transients. *Biotechnol Bioeng* 1999, 64:590-598.

Arya A S, Lee S A, Eiteman M A: Differential sensitivities of the growth of *Escherichia coli* to acrylate under aerobic and anaerobic conditions and its effect on product formation. *Biotechnol Lett* 2013, 35:1839-1843.

Atsumi S, Liao J C: Directed evolution of *Methanococcus jannaschii* citramalate synthase for biosynthesis of 1-propanol and 1-butanol by *Escherichia coli*. *Appl Environ Microbiol* 2008, 74:7802-7808.

Baba T, Ara T, Hasegawa M, Takai Y, Okumura Y, Baba M, Datsenko K A, Tomita M, Wanner B L, Mori H: Construction of *Escherichia coli* K-12 in-frame, single-gene knockout mutants: the Keio collection. *Mol Syst Biol* 2006, 2:2006.0008-2006.0008.

Berman K M, Cohn M: Phosphoenolpyruvate synthetase of *Escherichia coli*. Purification, some properties, and the role of divalent metal ions. *J Biol Chem* 1970, 245:5309-5318.

Brown T, Jones-Mortimer M, Kornberg H: The enzymic interconversion of acetate and acetyl-coenzyme A in *Escherichia coli*. *Microbiology* 1977, 102:327-336.

Buckel W, Barker H: Two pathways of glutamate fermentation by anaerobic bacteria. *J Bacteriol* 1974, 117:1248-1260.

Causey T, Shanmugam K, Yomano L, Ingram L: Engineering *Escherichia coli* for efficient conversion of glucose to pyruvate. *Proc Natl Acad Sci USA* 2004, 101:2235-2240.

Contiero J, Beatty C, Kumari S, DeSanti C, Strohl W, Wolfe A: Effects of mutations in acetate metabolism on high-cell-density growth of *Escherichia coli*. *J Industr Micro Biotechnol* 2000, 24:421-430.

Datsenko K A, Wanner B L: One-step inactivation of chromosomal genes in *Escherichia coli* K-12 using PCR products. *Proc of the Natl Acad Sci* 2000, 97:6640-6645.

De Mey M, De Maeseneire S, Soetaert W, Vandamme E: Minimizing acetate formation in *E. coli* fermentations. *J Industr Micro Biotechnol* 2007, 34:689-700.

Diaz-Ricci J, Regan L, Bailey J: Effect of alteration of the acetic acid synthesis pathway on the fermentation pattern of *Escherichia coli*. *Biotechnol Bioeng* 1991, 38:1318-1324.

Dittrich C R, Vadali R V, Bennett G N, San K Y: Redistribution of metabolic fluxes in the central aerobic metabolic pathway of *E. coli* mutant strains with deletion of the ackA-pta and poxB pathways for the synthesis of isoamyl acetate. *Biotechnol Prog* 2005, 21:627-631.

Eiteman M, Chastain M: Optimization of the ion-exchange analysis of organic acids from fermentation. *Anal Chim Acta* 1997, 338:69-75.

Eiteman M A, Altman E: Overcoming acetate in *Escherichia coli* recombinant protein fermentations. *Trends Biotechnol* 2006, 24:530-536.

Feng X, Mouttaki H, Lin L, Huang R, Wu B, Hemme C L, He Z, Zhang B, Hicks L M, Xu J: Characterization of the central metabolic pathways in *Thermoanaerobacter* sp. strain X514 via isotopomer-assisted metabolite analysis. *Appl Environ Microbiol* 2009, 75:5001-5008.

Howell D M, Xu H, White R H: (R)-citramalate synthase in Methanogenic archaea. *J Bacteriol* 1999, 181:331-333.

Hua Q, Yang C, Baba T, Mori H, Shimizu K: Responses of the central metabolism in *Escherichia coli* to phosphoglucose isomerase and glucose-6-phosphate dehydrogenase knockouts. *J Bacteriol* 2003, 185:7053-7067.

Jensen P R, Michelsen O: Carbon and energy metabolism of atp mutants of *Escherichia coli*. J Bacteriol 1992, 174: 7635-7641.

Johnson D W, Eastham G R, Poliakoff M, Huddle T A: Method of producing acrylic and methacrylic acid. *Google Patents;* 2012.

Kao K C, Tran L M, Liao J C: A global regulatory role of gluconeogenic genes in *Escherichia coli* revealed by transcriptome network analysis. *J Biol Chem* 2005, 280: 36079-36087.

Koebmann B J, Westerhoff H V, Snoep J L, Nilsson D, Jensen P R: The glycolytic flux in *Escherichia coli* is controlled by the demand for ATP. *J Bacteriol* 2002, 184:3909-3916.

Li M, Yao S, Shimizu K: Effect of poxB gene knockout on metabolism in *Escherichia coli* based on growth characteristics and enzyme activities. *World J Microb Biot* 2007, 23:573-580.

Lin H, Castro N M, Bennett G N, San K-Y: Acetyl-CoA synthetase overexpression in *Escherichia coli* demonstrates more efficient acetate assimilation and lower acetate accumulation: a potential tool in metabolic engineering. *Appl Microbiol and Biotechnol* 2006, 71:870-874.

Martinez I, Zhu J, Lin H, Bennett G N, San K-Y: Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways. *Metab Eng* 2008, 10:352-359.

Nakano K, Rischke M, Sato S, Märkl H: Influence of acetic acid on the growth of *Escherichia coli* K12 during high-cell-density cultivation in a dialysis reactor. *Appl Microbiol and Biotechnol* 1997, 48:597-601.

Nicolas C, Kiefer P, Letisse F, Körmer J, Massou S, Soucaille P, Wittmann C., Lindley N D, Portais J C: Response of the central metabolism of *Escherichia coli* to modified expression of the gene encoding the glucose-6-phosphate dehydrogenase. *FEBS Lett* 2007, 581:3771-3776.

Noda S, Takezawa Y, Mizutani T, Asakura T, Nishiumi E, Onoe K, Wada M, Tomita F, Matsushita K, Yokota A: Alterations of cellular physiology in *Escherichia coli* in response to oxidative phosphorylation impaired by defective F1-ATPase. *J Bacterial* 2006, 188:6869-6876.

Phue J-N, Lee S J, Kaufman J B, Negrete A, Shiloach J: Acetate accumulation through alternative metabolic pathways in ackA-pta-poxB-triple mutant in *E. coli* B (BL21). *Biotechnol Lett* 2010, 32:1897-1903.

Risso C, Van Dien S J, Orloff A, Lovley D R, Coppi M V: Elucidation of an alternate isoleucine biosynthesis pathway in *Geobacter sulfurreducens*. *J Bacteriol* 2008, 190: 2266-2274.

Rose I A, Grunberg-Manago M, Korey S R, Ochoa S: Enzymatic phosphorylation of acetate. *J Biol Chem* 1954, 211:737-756.

Semkiv M V, Dmytruk K V, Abbas C A, Sibirny A A: Increased ethanol accumulation from glucose via reduction of ATP level in a recombinant strain of *Saccharomyces cerevisiae* overexpressing alkaline phosphatase. *BMC Biotechnol* 2014, 14:42.

U.S. EPA. Nitrogen, Ammonia. Method 250.1 (Colorimetric). pp. 350-1.1-350-1.4. In Methods for Chemical Analysis of Water and Wastes. EPA-600/4-79-020. U.S. E.P.A., Cincinnati, Ohio USA. 1983.

Vemuri G, Altman E, Sangurdekar D, Khodursky A, Eiteman M: Overflow metabolism in *Escherichia coli* during steady-state growth: transcriptional regulation and effect of the redox ratio. *Appl Environ Microbiol* 2006a, 72:3653-3661.

Vemuri G N, Eiteman M A, Altman E: Increased recombinant protein production in *Escherichia coli* strains with overexpressed water-forming NADH oxidase and a deleted ArcA regulatory protein. *Biotechnol Bioeng* 2006b, 94:538-542.

Wanner B, Wilmes-Riesenberg M: Involvement of phosphotransacetylase, acetate kinase, and acetyl phosphate synthesis in control of the phosphate regulon in *Escherichia coli*. *J Bacteriol* 1992, 174:2124-2130.

Wu X, Eiteman M A: Production of citramalate by metabolically engineered *Escherichia coli*. *Biotechnol Bioeng* 2016, 113:2670-2675.

Wu X, Altman R, Eiteman M A, Altman E: Adaptation of *Escherichia coli* to elevated sodium concentrations increases cation tolerance and enables greater lactic acid formation," *Appl Environ Microbiol* 2014, 80:2880-2888.

Zhang K, Woodruff A P, Xiong M, Zhou J, Dhande Y K: A synthetic metabolic pathway for production of the platform chemical isobutyric acid. *ChemSusChem* 2011, 4:1068-1070.

Zhao J, Baba T, Mori H, Shimizu K: Effect of zwf gene knockout on the metabolism of *Escherichia coli* grown on glucose or acetate. *Metab Eng* 2004, 6:164-174.

Zhou Y, Nambou K, Wei L, Cao J, Imanaka T, Hua Q: Lycopene production in recombinant strains of *Escherichia coli* is improved by knockout of the central carbon metabolism gene coding for glucose-6-phosphate dehydrogenase. *Biotechnology Letters* 2013, 35:2137-2145.

Zhu Y, Eiteman M A, Altman R, Altman E: High glycolytic flux improves pyruvate production by a metabolically engineered *Escherichia coli* strain. *Appl Environ Microbiol* 2008, 74:6649-6655.

Example 3

Citramalic Acid is Produced from Glycerol in Metabolically Engineered *Escherichia coli*

Abstract

The microbial product citramalic acid (citramalate) serves as a five-carbon precursor for the chemical synthesis of methacrylic acid. We compared citramalate and acetate accumulation from glycerol in shake flasks using numerous *Escherichia coli* strains overexpressing the citramalate synthase gene cimA. These studies revealed that gltA coding citrate synthase, leuC coding 3-isopropylmalate dehydratase, and acetate pathway genes (in particular poxB coding pyruvate oxidase) play helpful roles in elevating citramalate formation and minimizing acetate formation. Controlled batch experiments at the 1.0 L scale confirmed that deletions in all three acetate-production genes (poxB, as well as ackA coding acetate kinase and pta coding phosphotransacetylase) were helpful in minimizing acetate formation to less than 1 g/L during citramalate production from 30 g/L glycerol. Fed-batch processes using MEC568/pZE12-cimA (gltA leuC ackA-pta poxB) generated over 31 g/L citramalate and less than 2 g/L acetate from either purified or crude glycerol at yields exceeding 0.50 g citramalate/g glycerol in 132 h. These results hold promise for the viable formation of citramalate from unrefined glycerol.

Introduction

The commercial manufacture and use of biodiesel has been rapidly emerging in Europe and US during the last two decades. As an alternative to petrochemical fuels, biodiesel is superior in its health and environmental impact, including low sulfur content, lower emission of harmful off-gases and a better lifecycle of $CO_2$ (Bournay et al., 2005). One key challenge in the development and adoption of biodiesel is the low value by-product glycerol, which is generated at about 10% mass ratio from the esterification or transesterification of vegetable oil and animal fats (Ma and Hanna, 1999). Fortunately, many microorganisms can naturally utilize glycerol as the sole carbon and energy source, and glycerol is a potential substitute for traditional carbohydrates such as sucrose or starch in industrial fermentation processes (Behr et al., 2008). Glycerol has been evaluated as a raw material for the production of many microbial products, including hydrogen (Sabourin-Provost and Hallenbeck, 2009), 1,3-propanediol (Chatzifragkou et al., 2011), 2,3-butanediol (Yang et al., 2015) and succinic acid (Gao et al., 2016).

Methacrylic acid (MAA) is a commodity chemical with an estimated annual global market of about 2.2 million tons, and it is used primarily for the synthesis of poly(methyl methacrylate) (Zhang et al., 2011). This polyester is widely used as a transparent thermoplastic in construction, furniture, medical material, and display technologies. The most common route for MAA synthesis converts acetone cyanohydrin to methacrylamine sulfate using sulfuric acid (Salkind et al., 1959; Bauer, 2000; Nagai, 2001). Sulfuric acid regeneration and hazards associated with volatile cyanides are concerns for industrial MAA production, and companies have sought other routes from isobutene, isobutyric acid, and ethylene (Bauer, 2000; Nagai, 2001). Although direct microbial production of MAA and acrylate with its reduced hazards has been proposed, acrylates are extremely toxic to microorganisms such as *Escherichia coli* (Todd et al., 2012; Arya et al., 2013).

Recently, we reported a microbial approach to produce citramalic acid (citramalate, (R)-2-methylmalic acid, (2R)-2-hydroxy-2-methylbutanedioate) from renewable carbohydrates. Citramalate can be directly converted to MAA by base-catalyzed decarboxylation and dehydration (Johnson et al., 2015). In a fed-batch fermentation, 46.5 g/L citramalate was formed with a yield of 0.63 g/g from glucose using an engineered *Escherichia coli* overexpressing the cimA gene coding citramalate synthase (Example 1). Despite the deletion of citrate synthase (coded by gltA) and acetate kinase (ackA), about 10 g/L acetate were still formed as an undesirable by-product from glucose. The maximum theoretical yield of citramalate from glycerol in *E. coli* is 0.80 g/g (FIG. 1), and the stoichiometric equation for the biochemical conversion is:

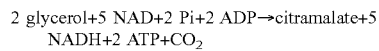

2 glycerol+5 NAD+2 Pi+2 ADP→citramalate+5 NADH+2 ATP+$CO_2$

Figure 13:
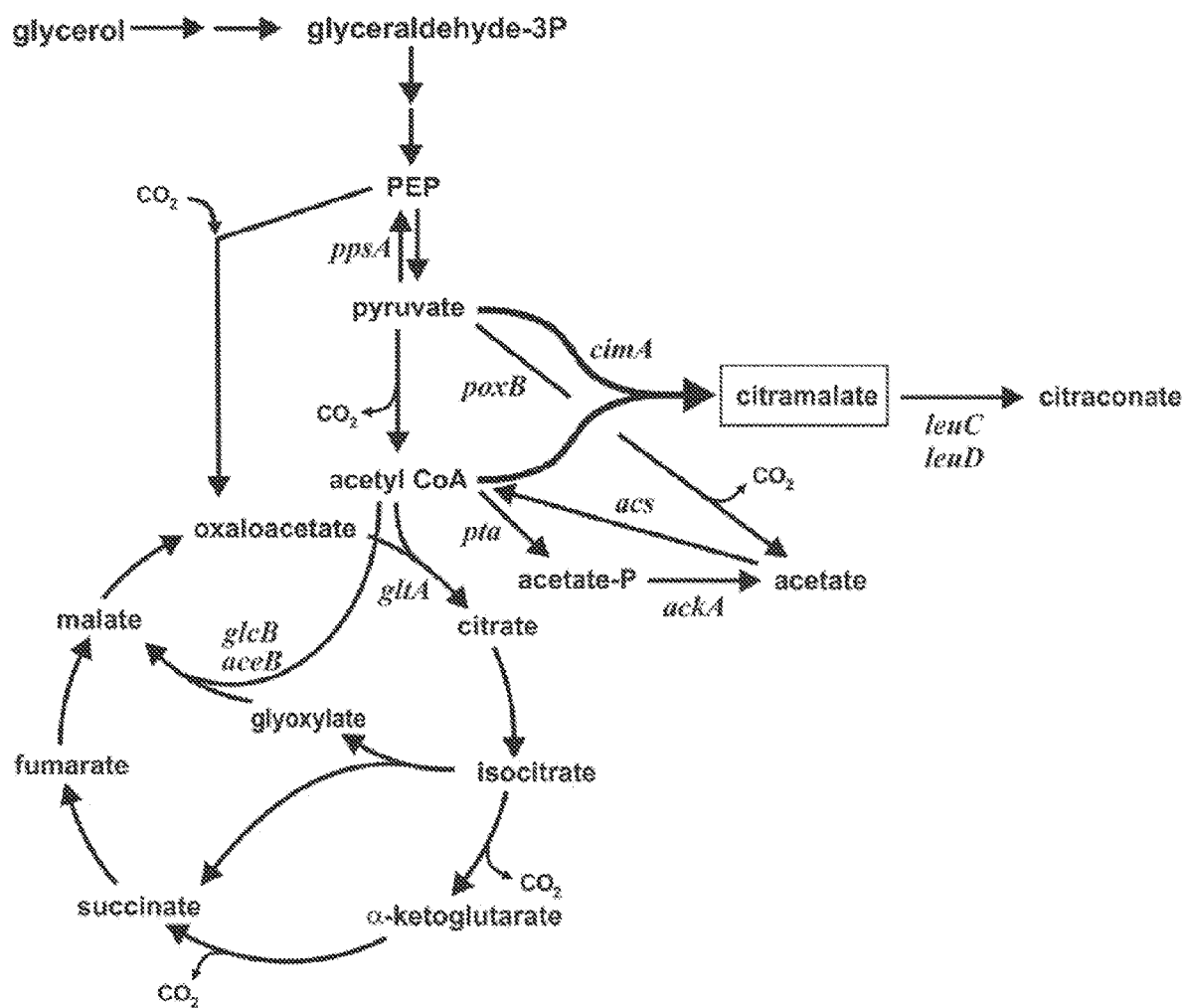
FIG. 13 shows biosynthesis of citramalate in *Escherichia coli* expressing the cimA gene coding citramalate synthase. Key genes (and coded enzymes) are: leuC and leuD (3-isopropylmalate dehydratase), gltA (citrate synthase), glcB and aceB (malate synthase), pta (phosphotransacetylase), ackA (acetate kinase), poxB (pyruvate oxidase), ppsA (phosphoenolpyruvate synthetase).

The goal of this study was to examine citramalate formation from glycerol by *Escherichia coli*. In addition to studying whether 5-carbon citramalate can be generated directly from both purified and crude 3-carbon glycerol at high yield, we examined strategies to reduce the formation of acetate as a by-product (see FIG. 13).

Materials and Methods
Strain Construction

Strains used in this study are shown in Table 3. Gene mutations were transduced into *E. coli* MG1655 from their respective strains in the KEIO collection (Baba et al., 2006) by the P1 phage method. The Δpta knockout was constructed using the λ Red recombination (Datsenko and Wanner, 2000). To knockout multiple genes in single strain, the Kan antibiotic marker was removed using pCP20 (Datsenko and Wanner, 2000). In knockout strains, forward primers external to the target gene and reverse primers within the kanamycin resistance cassette were used to check for proper chromosomal integration. In cured strains, the removal of the markers was verified by PCR. Plasmid pZE12-cimA was transformed into all strains for citramalate production (Example 1).

TABLE 3

Strains used in this study.

| Strain | Genotype | Notes |
|---|---|---|
| MG1655 | *E. coli* F- λ- ilvG rfb-50 rph-1 | Wild type |
| MEC480 | MG1655 ΔgltA770::Kan | Example 1 |
| MEC481 | MG1655 ΔaceB781::Kan | Example 1 |
| MEC482 | MG1655 ΔglcB749::Kan | Example 1 |
| MEC485 | MG1655 ΔaceB781::(FRT) ΔglcB749::Kan | Example 1 |
| MEC490 | MG1655 ΔgltA770::(FRT) ΔleuC779::Kan | Example 1 |
| MEC491 | MG1655 ΔgltA770::(FRT) ΔleuD778::Kan | Example 1 |
| MEC498 | MG1655 ΔgltA770::(FRT) ΔleuC779::(FRT) | Example 1 |
| MEC499 | MEC498 ΔackA778::Kan | Example 1 |
| MEC562 | MEC498 ΔackA778-pta-779::Kan | This study |
| MEC564 | MEC498 ΔackA778-pta-779::(FRT) Δpps-776::Kan | This study |
| MEC566 | MEC498 ΔackA778-pta-779::(FRT) Δacs-763::Kan | This study |
| MEC568 | MEC498 ΔackA778-pta-779::(FRT) ΔpoxB772::Kan | This study |
| MEC596 | MEC498 ΔackA778::(FRT) ΔpoxB772::Kan | This study |

Growth Medium

XP medium contained (per L): 3.00 g glycerol, 1.00 g/L peptone, 1.44 g $KH_2PO_4$, 2.11 g $K_2HPO_4$, 2.00 g $K_2SO_4$, 3.50 g $NH_4Cl$, 20.00 mg $Na_2(EDTA).2H_2O$, 0.15 g $MgSO_4.7H_2O$, 20 mg thiamine-HCl, 0.25 mg $ZnSO_4$, 0.125 mg $CuCl_2.2H_2O$, 1.25 mg $MnSO_4.H_2O$, 0.875 mg $CoCl_2.6H_2O$, 0.06 mg $H_3BO_3$, 0.25 mg $Na_2MoO_4.2H_2O$, 5.50 mg $FeSO_4.7H_2O$, and 20 mg citric acid. For the growth of strains having leuC or leuD knockouts, the medium was supplemented with 0.20 g/L L-leucine. For the growth of strains having gltA knockouts, the medium was supplemented with 1.00 g/L L-glutamate. *E. coli* is unable to utilize citrate under aerobic conditions (Koser, 1924). Additionally, 50 mg/L ampicillin and/or 100 mg/L kanamycin were added for plasmid-containing strains or strains having antibiotic resistance. The crude glycerol from biodiesel process was generously provided by a local biodiesel producer (Down To Earth Energy, LLC, Monroe, Ga., USA) and contained 58.6% w/w glycerol and 0.3% w/w methanol.

Shake Flask, Batch and Fed-Batch Processes

To compare various strains for citramalate production in shake flasks, cells were first grown in 3 mL Lysogeny Broth (LB) at 37° C. and 250 rpm (19 mm pitch). After 10-14 h, 0.5 mL was used to inoculate 50 mL of XP medium containing 0.2 mM IPTG in 500 mL baffled shake flasks (in triplicate). After growth at 37° C. and 250 rpm (19 mm pitch) for 24 h, these shake flask cultures were analyzed for citramalate synthase activity, citramalate and intracellular acetyl-CoA concentration.

To examine citramalate production under controlled bioreactor conditions, cells were first grown as described above in 3 mL LB and then 50 mL XP medium. After 18 h the shake flask contents were used to inoculate a 2.5 L bioreactor (Bioflo 2000, New Brunswick Scientific Co., New Brunswick, N.J., USA) containing 1.0 L XP medium modified to contain 30 g/L glycerol, 5 g/L peptone, 3 g/L L-glutamate and 1 g/L L-leucine (but otherwise as described above) and 0.2 mM IPTG initially. For duplicate batch and fed-batch processes, the agitation was 400 rpm, and air was sparged at 1.0 L/min, which maintained the dissolved oxygen above 40% of saturation. The pH was controlled at 7.0 using 20% (w/v) NaOH, and the temperature was controlled at 37° C. For the fed-batch process, an additional 30 g glycerol and 5 g peptone dissolved in 60 mL were added when the glycerol concentration decreased below 5 g/L.

Analytical Methods

The optical density at 600 nm (OD) (UV-650 spectrophotometer, Beckman Instruments, San Jose, Calif., USA) was used to monitor cell growth. Extracellular organic acids were analyzed by HPLC using a Refractive Index detector as previously described (Eiteman and Chastain, 1997). Glutamate concentration was measured using a glutamate assay kit (Sigma-Aldrich Co., St. Louis, Mo., USA). Acetyl-CoA was analyzed by the previously established method (Gao et al., 2007).

Cell-free extracts were also used to measure citramalate synthase activity by the generation of free CoA and its reaction product with 5,5'-dithiobis(2-nitrobenzoic acid) detected at a wavelength of 412 nm (Howell et al., 1999). One Unit of activity is the amount of enzyme that generates one µmole of CoA in one minute at 37° C.

Results and Discussion

Comparison of Citramalate and Acetate Formation by Various Strains

Figure 14:
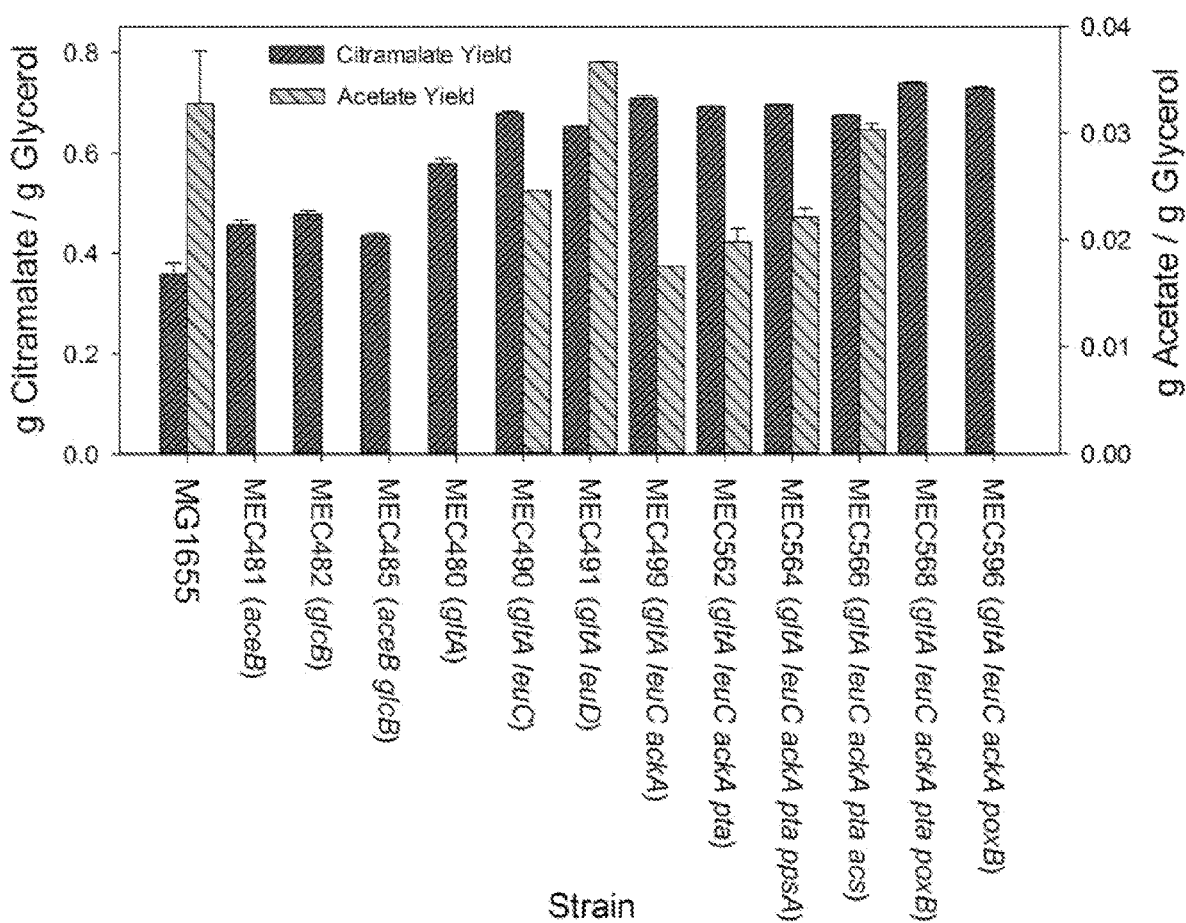
FIG. 14 shows comparison of citramalate yield and acetate yield from 3 g/L glycerol in triplicate shake flasks using various knockout strains of *E. coli* expressing the cimA gene. The leuC or leuD strains additionally contained 0.2 g/L L-leucine, while gltA strains contained 1 g/L L-glutamate.

In *E. coli* overexpressing citramalate synthase coded by the cimA gene, citramalate accumulates as the reaction product of the condensation of pyruvate and acetyl-CoA. In wild-type *E. coli* expressing citramalate synthase (MG1655/pZE12-cimA) just over 1 g/L citramalate formed from 3 g/L glycerol, resulting in a citramalate yield of 0.36 g/g (FIG. 14). This wild-type strain expressing citramalate synthase generated substantial acetate in shake flasks, resulting in a yield of 0.033 g acetate/g glycerol (FIG. 14). Since acetyl CoA and pyruvate are involved in numerous enzyme reactions, we compared citramalate formation from glycerol using several strains having knockouts in genes associated with these metabolites.

Acetyl-CoA is converted to malate via malate synthase coded in *E. coli* by the glcB and aceB genes (Ornston and Ornston, 1969; Molina et al., 1994). We therefore constructed MEC481 (MG1655 aceB), MEC482 (MG1655 glcB) and MEC485 (MG1655 aceB glcB). Compared to MG1655/pZE12-cimA, MEC481/pZE12-cimA and MEC482/pZE12-cimA showed about 28% and 35% higher citramalate accumulation, respectively (FIG. 14). The strain having knockouts in both malate synthase genes, MEC485/pZE12-cimA, resulted in 22% greater citramalate compared to the wild-type. Acetyl CoA is also converted to citrate via citrate synthase coded by the gltA gene (Eikmanns et al., 1994), and we therefore examined citramalate production in MEC480 (MG1655 gltA) expressing citramalate synthase. MEC480/pZE12-cimA grew poorly on XP medium, but growth was restored when the medium additionally contained 1 g/L L-glutamate. MEC480/pZE12-cimA grown with supplemented glutamate accumulated 0.58 g citramalate/g glycerol, 63% more than MG1655/pZE12-cimA. Since MG1655/pZE12-cimA grown in XP medium supplemented with 1 g/L L-glutamate also generated the same yield of citramalate as the same strain without added glutamate, we attribute the 63% increase in citramalate formation in MEC480/pZE12-cimA to the gltA knockout and not to the presence of glutamate. Therefore, media for strains having the gltA knockout were henceforth supplemented with 1 g/L L-glutamate. These strains having knockouts of enzymes associated with the glyoxylate shunt or the TCA cycle (i.e., aceB, glcB, gltA) accumulated no detectable acetate.

Citramalate could be potentially metabolized in E. coli by 3-isopropylmalate dehydratase coded by the leuC (large subunit) and leuD (small subunit) genes (Fultz et al., 1979; Fultz and Kemper, 1981). The two subunits are both required for the activity of isopropylmalate isomerase, an enzyme which is necessary for leucine biosynthesis in E. coli (Yang and Kessler, 1974), and each of these individual deletions were examined by comparing MEC490 (MG1655 gltA leuC) and MEC491 (MG1655 gltA leuD). With the deletion of either leuC or leuD, E. coli did not grow in XP medium containing glycerol as the sole carbon source, despite the presence of peptone in the medium. Growth was restored by the addition of 0.2 g/L L-leucine, and MEC490/pZE12-cimA accumulated 0.68 g citramalate/g glycerol, 13% greater than MEC480/pZE12-cimA, while MEC491/pZE12-cimA accumulated 0.65 g citramalate/g glycerol (FIG. 14). MEC490/pZE12-cimA and MEC491/pZE12-cimA both accumulated similar acetate as MG1655/pZE12-cimA.

Although leuC led to more citramalate in the gltA strain, this additional knockout also led to acetate formation from glycerol. To reduce acetate formation in the E. coli gltA leuC expressing citramalate synthase, we examined several pathways related to the acetate and pyruvate metabolism. Four enzymes exist in E. coli related to acetate and acetyl-CoA. Acetate kinase coded by ackA and phosphotransacetylase coded by pta (Lee et al., 1990; Matsuyama et al., 1994) are typically considered the primary routes for the conversion of acetyl-CoA to acetyl-phosphate (acetyl-P) and to acetate. Acetyl-P can form acetate via other routes, also, since it can serve as a phosphate donor in gene regulation and protein-dependent transport systems (Hong et al., 1979; Wanner and Wilmes-Riesenberg, 1992). On the other hand, acetyl-CoA synthetase coded by acs functions as an anabolic route and scavenges acetate to acetyl-CoA (Lin et al., 2006). Finally, pyruvate oxidase coded by poxB can play a role in aerobic growth of E. coli and in acetate formation from pyruvate (Abdel-Hamid et al., 2001). We also examined phosphoenolpyruvate synthetase coded by ppsA, which could affect the intracellular pyruvate and acetyl CoA pools (Niersbach et al., 1992). We constructed several strains having these knockouts, expressed citramalate synthase and determined the citramalate and acetate formation in shake flasks (FIG. 14).

The additional deletion in the ackA gene or the combination of ackA and pta genes increased citramalate yield slightly to 0.71 g/g and 0.69 g/g, respectively. However, both MEC499/pZE12-cimA and MEC562/pZE12-cimA still formed acetate with yields of about 0.018 g/g-0.020 g/g (FIG. 14). Compared to E. coli gltA leuC ackA-pta expressing citramalate synthase, an additional ppsA deletion did not affect citramalate or acetate formation significantly, while an additional acs knockout actually elevated acetate yield to 0.030 g/g. Inexplicably, one previous investigation of an acs deletion strain resulted in lower specific acetate formation from glucose (Contiero et al., 2000), while in another study overexpression of acs significantly reduced acetate formation (Lin et al., 2006). In our study using strains with additional gene deletions, the increase in acetate formation when acs is deleted (in the ackA-pta background) suggests that some acetate is formed via pyruvate oxidase, and that acetyl CoA synthase provides the cells with a means to metabolize that acetate partially. In support of this conclusion, the poxB knockout (in the ackA-pta background) eliminated acetate formation in the shake flask culture, and increased citramalate yield from glycerol to 0.74 g/g. To determine whether poxB or the combination of pta poxB was helpful in eliminating acetate formation, we also examined MEC596/pZE12-cimA, which generated 0.73 g citramalate/g glycerol and no detectable acetate. These results conclusively show that pyruvate oxidase is a key enzyme in the accumulation of acetate during citramalate production in E. coli. The deletion of poxB has similarly reduced acetate in an ackA-pta strain during the aerobic production of succinate by E. coli (Lin et al., 2005).

Figure 15:
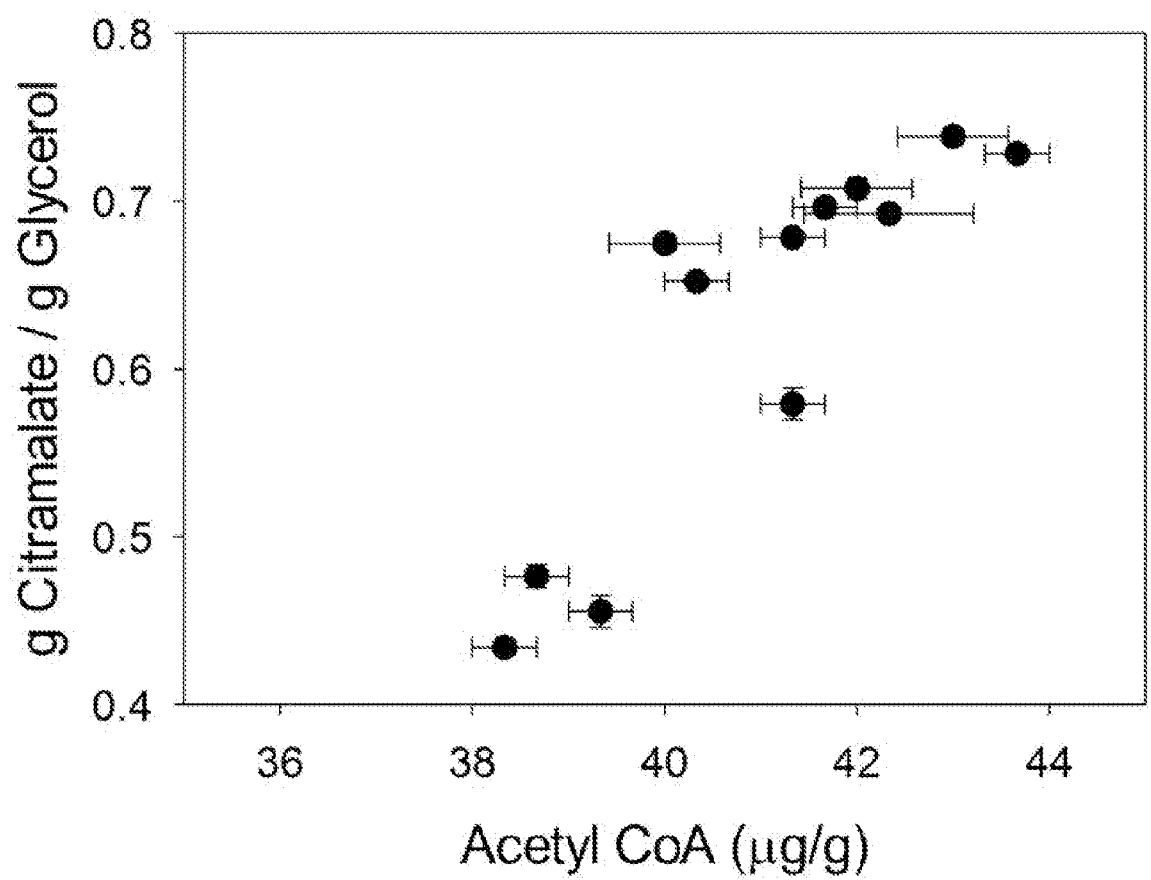
FIG. 15 shows relationship between citramalate yield and intracellular acetyl CoA concentration in shake flasks using various knockout strains of *E. coli* expressing the cimA gene (shown in FIG. 14).

Acetyl CoA is an important substrate for citramalate synthase, and we measured intracellular acetyl CoA concentration in all triplicate shake flask experiments. These results were used to determine whether any correlation exists between intracellular acetyl CoA and citramalate yield in the 13 different strains (FIG. 15). The results show that increased citramalate yield correlates strongly with increased acetyl CoA concentration.

Controlled Batch Citramalate Production from Glycerol

In order to determine whether shake flask results were transferable to larger scale, we next examined citramalate production at the 1.0 liter scale in controlled bioreactors. In duplicate, we compared six strains expressing citramalate synthase: MG1655, MEC490, MEC499, MEC562, MEC568, or MEC596. To accommodate greater cell growth, the medium contained 30 g/L glycerol and 5 g/L peptone, as well as 3 g/L glutamate and 1 g/L L-leucine (for strains with gltA leuC knockouts). The results of these batch processes are shown in Table 4.

TABLE 4

Summary of citramalate and acetate formation from 30 g/L glucose in controlled batch bioreactor using various E. coli strains.

| Strain | Key gene deletions | Time (h) | Citramalate Yield (g/g) | Acetate Yield (g/g) |
|---|---|---|---|---|
| MG1655/pZE12-cimA | N/A | 30 | 0.143 | 0.002 |
| MEC490/pZE12-cimA | gltA leuC | 48 | 0.175 | 0.380 |
| MEC499/pZE12-cimA | gltA leuC ackA | 60 | 0.476 | 0.181 |
| MEC562/pZE12-cimA | gltA leuC ackA pta | 60 | 0.485 | 0.143 |
| MEC596/pZE12-cimA | gltA leuC ackA poxB | 66 | 0.560 | 0.086 |
| MEC568/pZE12-cimA | gltA leuC ackA pta poxB | 60 | 0.585 | 0.032 |

MG1655/pZE12-cimA reached an OD of over 20 in 24 h and accumulated 4.3 g/L citramalate (yield of 0.143 g/g) and 0.05 g/L acetate in 30 h (yield of 0.002 g/g). All other strains examined had the gltA and leuC knockouts which significantly slowed growth despite the presence of glutamate and leucine in the medium, and they generally reached an OD of 10 in 24-30 h. The gltA leuC knockouts alone (MEC490/pZE12-cimA) resulted in only 5.2 g/L citramalate (yield of 0.175 g/g) and 11.4 g/L acetate (yield of 0.380 g/g). In comparison the addition of an ackA deletion increased citramalate and diminished acetate formation. Nevertheless, the ackA deletion was insufficient to prevent acetate formation. The addition of either a pta or a poxB deletion to the gltA leuC ackA strain further decreased acetate formation, with the poxB resulting in a better reduction of this byproduct. The lowest accumulation of acetate was observed under controlled batch conditions using the strain with all three acetate pathway knockouts (gltA leuC ackA-pta poxB), and MEC568/pZE12-cimA also led to the greatest citramalate production (about 17.5 g/L). Typically, the phosphotransacetylase and acetate kinase activities are significant during cell growth, while pyruvate oxidase appears to become important during the stationary phase (Dittrich et al., 2005). Pyruvate oxidase moreover bypasses acetyl-CoA formation altogether. The controlled batch experiments contrast with previous shake flask results and demonstrate that shake flask results are weak predictors of larger scale processes. In particular, MEC490, MEC499, MEC596 and MEC568 showed insignificant acetate formation in shake flasks, whereas in the controlled and prolonged batch processes acetate accumulation was observed for all these strains.

During the growth of these strains, succinate, lactate, ethanol and pyruvate were not detected, and citramalate synthase activity was not affected by the *E. coli* strain genotype (data not shown). The combination of gltA leuC ackA-pta and poxB knockouts were important to achieve a high yield of citramalate and minimal acetate, and therefore MEC568 was used for further studies.

Fed-Batch Production of Citramalate

Figure 16:
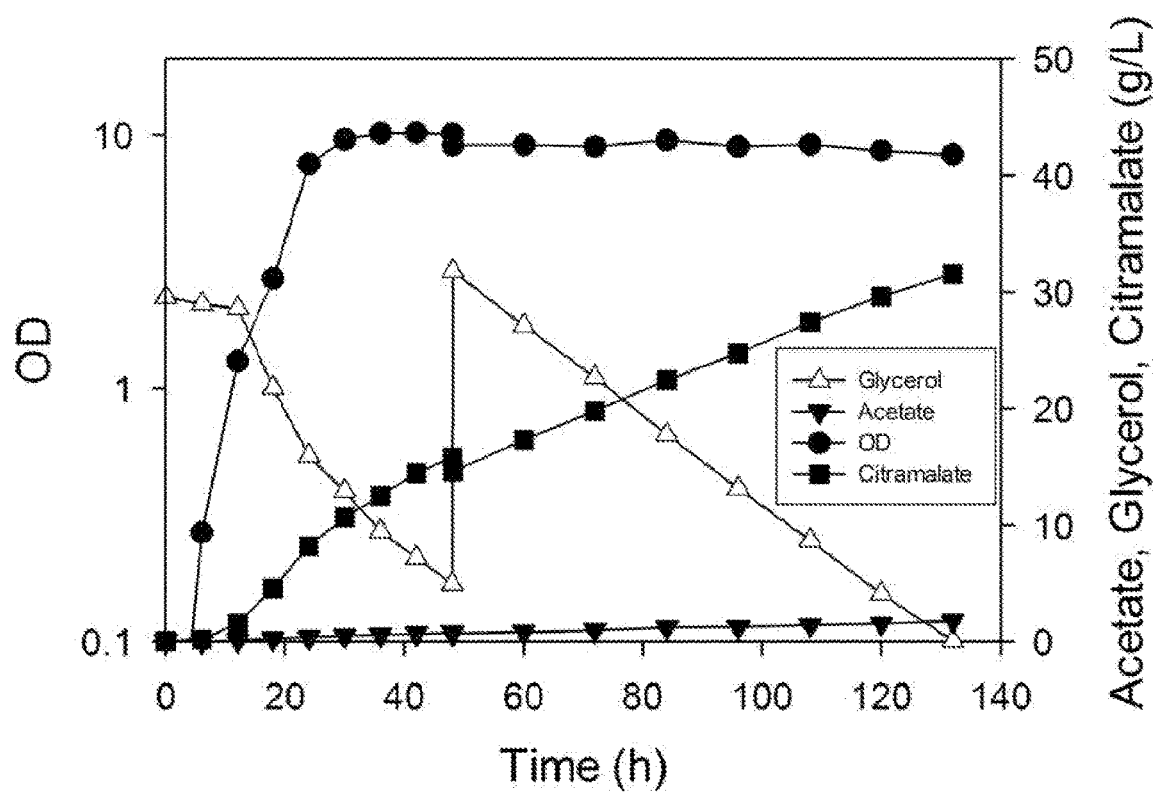
FIG. 16 shows citramalate production using pure glycerol in a 1.0 L fed-batch fermentation with MEC568/pZE12-cimA. Approximately 30 g purified glycerol and 5 g peptone in 60 mL was added at 48 h.

The final concentration of a fermentation product can often be maximized by continuous feeding of the carbon source. We therefore next completed duplicate experiments using a fed-batch process in which 30 g glycerol and 5 g peptone were added to the fermenter once when the glycerol concentration decreased below 5 g/L. MEC568/pZE12-cimA was selected for this study because this strain achieved the greatest citramalate yield in batch processes (Table 4). Like the batch process described above, for these fed-batch processes the OD reached 10.0 within 36 h at which time the citramalate concentration was 12.5 g/L (FIG. 16). After 132 h, the final citramalate concentration reached an average of 31.4 g/L, corresponding to a yield of 0.52 citramalate g/g glycerol. In addition, only 1.8 g/L acetate was formed as byproduct.

Citramalate Production Using Crude Glycerol

Figure 17:
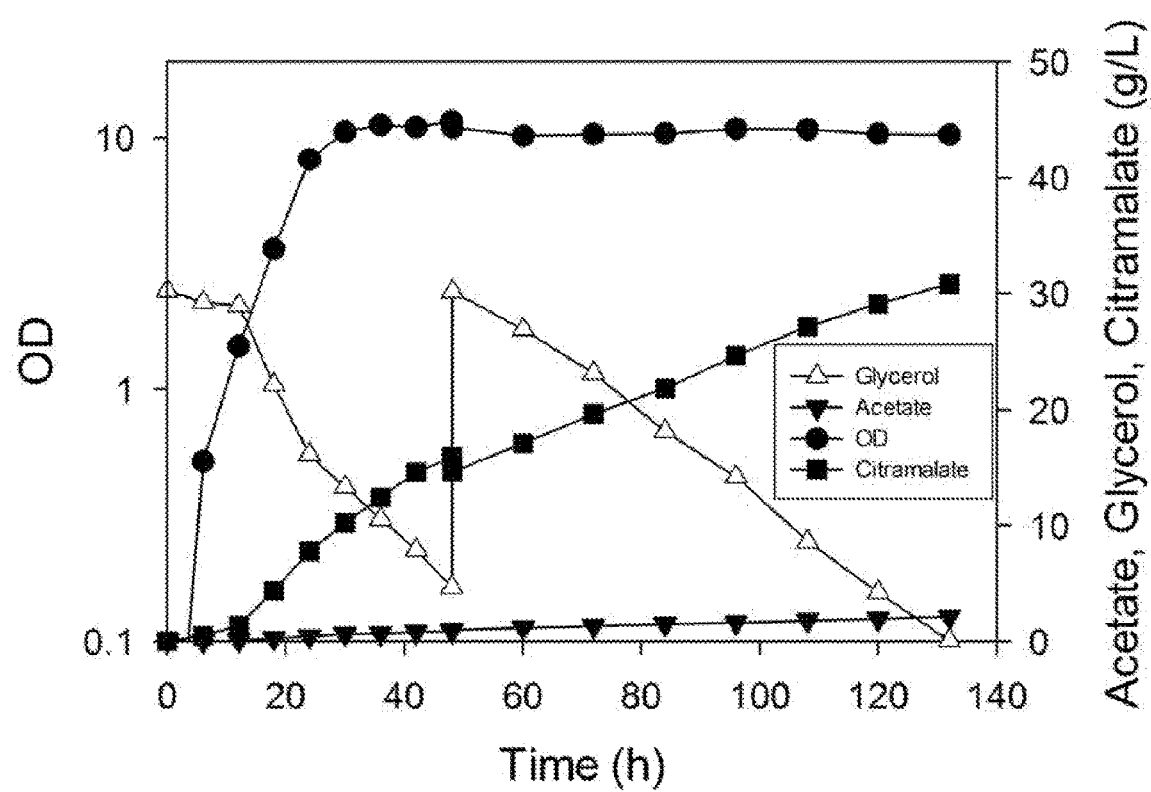
FIG. 17 shows citramalate production using crude glycerol in a 1.0 L fed-batch fermentation with MEC568/pZE12-cimA. Approximately 30 g crude glycerol and 5 g peptone was added at 48 h.

The rapid growth of the biodiesel industry has resulted in surplus availability of crude glycerol production, which has a purity of 60%-80% based on the type of oil used as feedstock (Ayoub and Abdullah, 2012). Crude glycerol also often contains 10%-15% methanol, 1.5%-2.5% ash, and 3.0%-5.0% soap as impurities (Ayoub and Abdullah, 2012). To determine if *E. coli* could be used to generate citramalate from crude glycerol, we next examined the fed-batch process using unrefined glycerol obtained directly from a local biodiesel manufacturer in place of purified glycerol. In this fed-batch process, about 31 g/L citramalate (0.51 g/g yield) and 1.9 g/L acetate were obtained using MEC568/pZE12-cimA (FIG. 17). This result is virtually identical to the fed-batch process using purified glycerol, and demonstrates that refining glycerol is not necessary for citramalate production by *E. coli*. Interestingly, the final OD was 22% greater when crude glycerol was used (10.3 vs. 8.4), possibly because of the presence of other unidentified carbon sources in the crude material. Crude glycerol has been used in other studies of biological conversions to value-added chemicals. For example, ethanol formation was similar for purified and unrefined glycerol by a *Klebsiella pneumoniae* mutant (Oh et al., 2011), and the same 1,3-propanediol concentration was achieved using purified or crude glycerol in a fed-batch fermentation, although the productivity was lower using crude glycerol (Hiremath et al., 2011).

Conclusions

Gene knockouts and fermentation optimization improve citramalate production from glycerol and also reduce acetate accumulation. Near elimination of acetate formation necessitates deletions in genes for both pathways associated with acetate formation: ackA coding acetate kinase, pta coding phosphotransacetylase, and poxB coding pyruvate oxidase. Fed-batch fermentations demonstrated that identical citramalate over 30 g/L can be generated from pure or crude glycerol at yield greater than 0.50 g citramalate/g glycerol. This result holds promise that crude glycerol could be used as for citramalate production and ultimately as a source of methacrylate.

REFERENCES

Abdel-Hamid, A. M., Attwood, M. M., Guest, J. R., 2001. Pyruvate oxidase contributes to the aerobic growth efficiency of *Escherichia coli*. Microbiology. 147, 1483-1498.

Arya, A. S., Lee, S. A., Eiteman, M. A., 2013. Differential sensitivities of the growth of *Escherichia coli* to acrylate under aerobic and anaerobic conditions and its effect on product formation. Biotechnol. Lett. 35, 1839-1843.

Ayoub, M., Abdullah, A. Z., 2012. Critical review on the current scenario and significance of crude glycerol resulting from biodiesel industry towards more sustainable renewable energy industry. Renew. Sustainable Energy Rev. 16, 2671-2686.

Baba, T., Ara, T., Hasegawa, M., Takai, Y., Okumura, Y., Baba, M., Datsenko, K. A., Tomita, M., Wanner, B. L., Mori, H., 2006. Construction of *Escherichia coli* K-12 in-frame, single-gene knockout mutants: the Keio collection. Mol. Syst. Biol. 2:2006.0008.

Bauer, W. Jr., 2000. Methacrylic acid and derivatives. Ullmann's Encyclopedia of Industrial Chemistry. Wiley-VCH, Weinheim.

Behr, A., Eilting, J., Irawadi, K., Leschinski, J., Lindner, F., 2008. Improved utilisation of renewable resources: new important derivatives of glycerol. Green Chem. 10, 13-30.

Bournay, L., Casanave, D., Delfort, B., Hillion, G., Chodorge, J. A., 2005. New heterogeneous process for biodiesel production: a way to improve the quality and the value of the crude glycerin produced by biodiesel plants. Catal. Today. 106, 190-192.

Chatzifragkou, A., Papanikolaou, S., Dietz, D., Doulgeraki, A. I., Nychas, G. E., Zeng, A., 2011. Production of 1,3-propanediol by *Clostridium butyricum* growing on biodiesel-derived crude glycerol through a non-sterilized fermentation process. Appl. Microbiol. Biotechnol. 91, 101-112.

Contiero, J., Beatty, C. M Kumari, S., DeSanti, C. L., Strohl, W. R., Wolfe, A. J., 2000. Effects of mutations in acetate metabolism in high-cell-density growth of *Escherichia coli*. J. Ind. Microbiol. Biotechnol. 24, 421-430.

Datsenko, K. A., Wanner, B. L., 2000. One-step inactivation of chromosomal genes in *Escherichia coli* K-12 using PCR products. Proc. Natl. Acad. Sci. U.S.A 97, 6640-6645.

Dittrich, C. R., Bennett, G. N., San, K. Y., 2005. Characterization of the acetate-producing pathways in *Escherichia coli*. Biotechnol. Prog. 21, 1062-1067.

Eikmanns, B., Thum-Schmitz, N., Eggeling, L., Ludtke, K., Sahm, H., 1994. Nucleotide sequence, expression and transcriptional analysis of the *Corynebacterium glutamicum* gltA gene encoding citrate synthase. Microbiology. 140, 1817-1828.

Eiteman, M. A., Chastain, M. J., 1997. Optimization of the ion-exchange analysis of organic acids from fermentation. Anal. Chim. Acta. 338, 69-75.

Fultz, P. N., Kemper, J., 1981. Wild-type isopropylmalate isomerase in *Salmonella typhimurium* is composed of two different subunits. J. Bacteriol. 148, 210-219.

Fultz, P. N., Kwoh, D. Y., Kemper, J., 1979. *Salmonella typhimurium* newD and *Escherichia coli* leuC genes code for a functional isopropylmalate isomerase in *Salmonella typhimurium-Escherichia coli* hybrids. J. Bacteriol. 137, 1253-1262.

Gao, L., Chiou, W., Tang, H., Cheng, X., Camp, H. S., Burns, D. J., 2007. Simultaneous quantification of malonyl-CoA and several other short-chain acyl-CoAs in animal tissues by ion-pairing reversed-phase HPLC/MS. J. Chromatogr. B. 853, 303-313.

Gao, C., Yang, X., Wang, H., Rivero, C. P., Li, C., Cui, Z., Qi, Q., Lin, C. S. K., 2016. Robust succinic acid production from crude glycerol using engineered *Yarrowia lipolytica*. Biotechnol. Biofuels. 9, 179.

Hiremath, A., Kannabiran, M., Rangaswamy, V., 2011. 1,3-Propanediol production from crude glycerol from jatropha biodiesel process. New Biotechnol. 28, 19-23.

Hong, J. S., Hunt, A. G., Masters, P. S., Lieberman, M. A., 1979. Requirement of Acetyl Phosphate for the Binding Protein-Dependent Transport Systems in *Escherichia coli*. Proc. Natl. Acad. Sci. U.S.A. 76, 1213-1217.

Howell, D. M., Xu, H., White, R. H., 1999. (R)-Citramalate synthase in *Methanogenic archaea*. J. Bacteriol. 181, 331-333.

Johnson, D. W., Eastham, G. R., Poliakoff, M., Huddle, T. A., 2015. Method of producing acrylic and methacrylic acid. U.S. Pat. No. 8,933,179 B2.

Koser, S. A., 1924. Correlation of citrate utilization by members of the colon-aerogenes group with other differential characteristics and with habitat. J. Bacteriol. 9, 59-77.

Lee, T. Y., Makino, K., Shinagawa, H., Nakata, A., 1990. Overproduction of acetate kinase activates the phosphate regulon in the absence of the phoR and phoM functions in *Escherichia coli*. J. Bacteriol. 172, 2245-2249.

Lin, H., Bennett, G. N., San, K.-Y., 2005. Genetic reconstruction of the aerobic central metabolism in *Escherichia coli* for the absolute aerobic production of succinate. Biotechnol. Bioeng. 89, 148-156.

Lin, H., Castro, N. M., Bennett, G. N., San, K.-Y., 2006. Acetyl-CoA synthetase overexpression in *Escherichia coli* demonstrates more efficient acetate assimilation and lower acetate accumulation: a potential tool in metabolic engineering. Appl. Microbiol. Biotechnol. 71, 870-874.

Ma, F., Hanna, M. A., 1999. Biodiesel production: a review. Bioresource Technol. 70, 1-15.

Matsuyama, A., Yamamoto-Otake, H., Hewitt, J., MacGillivray, R. T. A., Nakano, E., 1994. Nucleotide sequence of the phosphotransacetylase gene of *Escherichia coli* strain K12. Biochim. Biophys. Acta. 1219, 559-562.

Molina, I., Pellicer, M. T., Badia, J., Aguilar, J., Baldoma, L., 1994. Molecular characterization of *Escherichia coli* malate synthase G. Differentiation with the malate synthase A isoenzyme. Eur. J. Biochem. 224, 541-548.

Nagai, K., 2001. New developments in the production of methyl methacrylate. Appl. Catal. A-Gen. 221, 367-377.

Niersbach, M., Kreuzaler, F., Geerse, R. H., Postma, P. W., Hirsch, H. J., 1992. Cloning and nucleotide sequence of the *Escherichia coli* K-12 ppsA gene, encoding PEP synthase. Molec. Gen. Genet. 231, 332-336.

Oh, B. R., Seo, J. W., Heo, S. Y., Hong, W. K., Luo, L. H., Joe, M., Park, D. H., Kim, C. H., 2011. Efficient production of ethanol from crude glycerol by a *Klebsiella pneumonia* mutant strain. Bioresour. Technol. 102, 3918-3922.

Ornston, L. N., Ornston, M. K., 1969. Regulation of glyoxylate metabolism in *Escherichia coli* K-12. J. Bacteriol. 98, 1098-108.

Sabourin-Provost, G., Hallenbeck, P. C., 2009. High yield conversion of a crude glycerol fraction from biodiesel production to hydrogen by photofermentation. Bioresource Technol. 100, 3513-3517.

Salkind, M., Riddle, E. H., Keefer, R. W., 1959. Acrylates and methacrylates—raw materials, intermediates, and plant integration. Ind. Eng. Chem. 51, 1232-1238.

Todd, J. D., Curson, A. R. J., Sullivan, M. J., Kirkwood, M., Johnston, A. W. B., 2012. The *Ruegeria pomeroyi* acuI gene has a role in DMSP catabolism and resembles yhdH of *E. coli* and other bacteria in conferring resistance to acrylate. PLoS ONE. 7, e35947.

Yang, H. L., Kessler, D. P., 1974. Genetic analysis of the leucine region in *Escherichia coli*: gene-enzyme assignments. J. Bacteriol. 117, 63-72.

Yang, T., Rao, Z., Zhang, X., Xu, M., Xu, Z., Yang, S., 2015. Enhanced 2,3-butanediol production from biodiesel-derived glycerol by engineering of cofactor regeneration and manipulating carbon flux in *Bacillus amyloliquefaciens*. Microb. Cell Fact. 14, 122.

Wanner, B. L., Wilmes-Riesenberg, M. R., 1992. Involvement of phosphotransacetylase, acetate kinase, and acetyl phosphate synthesis in control of the phosphate regulon in *Escherichia coli*. J. Bacteriol. 174, 2124-2130.

Wu, X., Eiteman, M. A., 2016. Production of citramalate by metabolically engineered *Escherichia coli*. Biotechnol. Bioeng. 113, 2670-2675.

Zhang, K., Woodruff, A. P., Xiong, M., Zhou, J., Dhande, Y. K., 2011. A synthetic metabolic pathway for production of the platform chemical isobutyric acid. ChemSusChem, 4, 1068-1070.

Example 4

Engineering Citrate Synthase Improves Citramalic Acid Production in *Escherichia coli*

Introduction

Metabolic engineering of microbes has been widely applied in microbial production of fuels, chemicals, pharmaceuticals, and materials (Bommareddy et al., 2014; Chen et al., 2015; Lee and Kim, 2015). Most of the genetic toolboxes currently used in metabolic engineering are based on the modification of gene expression. For example, pathway flux can be modulated by altering the promoter strength (Alper et al., 2005), ribosome binding sites (Salis et al., 2009), codon usage (He et al., 2014), mRNA secondary structure (Liang et al., 2011), and deleting a gene for a competing pathway altogether. In the context of enzyme kinetics, each one of these approaches affects the quantity of active enzyme (i.e., $V_{MAX}$), but does not alter the intrinsic enzyme-substrate affinity ($K_M$). Thus, these strategies would not address protein-level limitations such as feedback inhibition or substrate specificity. In contrast, enzyme engineering not only allows fine tuning of a specific pathway, but this approach also improves overall enzyme activity and selectivity (reviewed by Otte and Hauer, 2015). One strategy is to evolve key enzymes in a biosynthesis pathway to achieve higher activity or specificity, and thus to obtain higher yields of the target molecule (Yoshikuni et al., 2008; Leonard et al., 2010; Machado et al., 2012). Protein engineering is rarely used as a strategy to reduce flux through a competing pathway (e.g., increase $K_M$ of an existing enzyme), or more generally towards the goal of altering enzyme properties to affect pathway flux.

Acetyl CoA is a key central metabolite at the junction of glycolysis and the tricarboxylic acid (TCA) cycle. Of the 11 precursors in central metabolism withdrawn for the synthesis of Escherichia coli biomass, more acetyl CoA on a molar basis is consumed for biomass than any other precursor (Zhao et al., 2004). Acetyl CoA is also the starting material for a surprisingly diverse suite of biochemical products of commercial interest, including butanol (Anfelt et al., 2015), poly(hydroxyalkanoate)s (Centeno-Leija et al., 2014), polyketides (Choi and Da Silva, 2014) and isoprenoids (Lv et al., 2016). Most studies concerned with elevating the acetyl CoA availability have focused on eliminating acetate formation, for example, by knocking genes coding for phosphotransacetylase, acetate kinase and pyruvate oxidase (Dittrich et al., 2005). These enzymes mediate the conversion of acetyl CoA or pyruvate to acetate, and their deletion reduces the formation of this by-product without preventing growth. However, $^{13}$C-labelling experiments using wild-type E. coli at steady-state demonstrate that over 62% of the acetyl CoA generated is directed to the TCA cycle, over 22% is directed to biomass generation, while actually less than 16% is directed to the by-product acetate (Zhao et al., 2004). These results suggest that a reduction of flux toward acetate might minimally impact the acetyl CoA pool, since the other two acetyl CoA sinks could absorb this fairly small metabolic perturbation. Because entry into the TCA cycle actually constitutes the principal use of acetyl CoA, reducing this flux mediated by citrate synthase should have a more profound effect on the availability of acetyl CoA for other metabolically engineered pathways leading from acetyl CoA.

Figure 18:
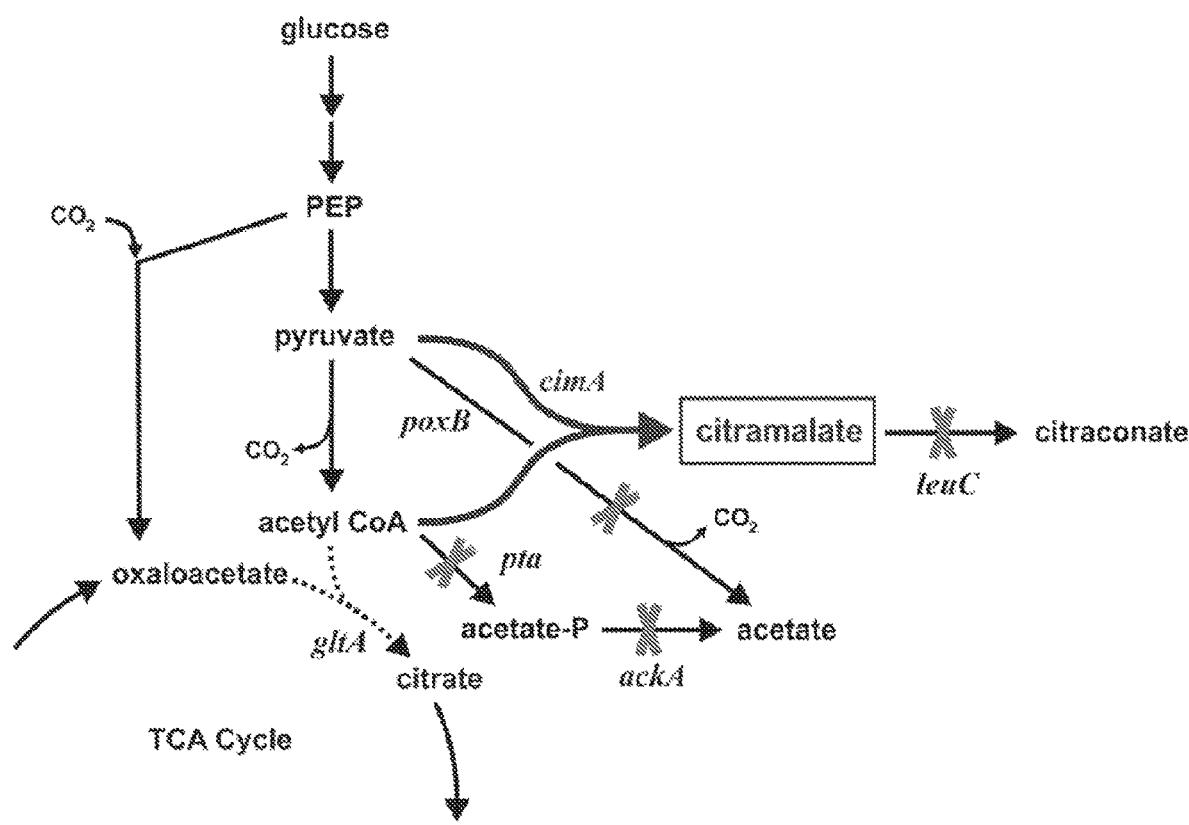
FIG. 18 shows biosynthesis of citramalate in *Escherichia coli* expressing the cimA gene coding citramalate synthase. Key genes which were knocked out (and coded enzymes) are: leuC (3-isopropylmalate dehydratase), pta (phosphotransacetylase), ackA (acetate kinase), and poxB (pyruvate oxidase). Point mutations were introduced into citrate synthase coded by the gltA gene (indicated by dotted curve) which reduced the activity of this enzyme.

With an estimated annual global market of about 2.2 million tons, the commodity chemical methacrylic acid (MAA) is primarily used for the synthesis of poly(methyl methacrylate) (Zhang et al., 2011). This polyester finds application as a transparent thermoplastic in construction, furniture, medical materials, and display technologies. The most common current production route for MAA synthesis converts acetone cyanohydrin to methacrylamine sulfate using sulfuric acid (Salkind et al., 1959; Bauer, 2000; Nagai, 2001). Sulfuric acid regeneration and volatile cyanides are concerns for industrial MAA production, and companies have sought other routes from isobutene, isobutyric acid, and ethylene (Bauer, 2000; Nagai, 2001). Although direct microbial production of MAA and acrylate has been proposed, acrylates are extremely toxic to microorganisms such as E. coli (Todd et al., 2012; Arya et al., 2013). An alternative is a hybrid approach, whereby a microbially-derived biochemical is converted to MAA in a chemical step. For example, citramalic acid, or citramalate, can be directly converted to MAA by base-catalyzed decarboxylation and dehydration (Johnson et al., 2015). Recently, we demonstrated the microbial formation of nearly 50 g/L citramalate from renewable carbohydrates using E. coli (Example 1). The key enzyme citramalate synthase coded by the cimA gene uses pyruvate and acetyl CoA as substrates (FIG. 18). An elevated concentration of intracellular acetyl CoA correlated with high citramalate formation and were associated with a deletion in gltA coding citrate synthase (Example 1). Because α-ketoglutarate (i.e., 2-oxoglutarate) is a precursor for several amino acids, an active citrate synthase is required for growth on glucose as the sole carbon source (Lakshmi and Helling, 1976). Thus, E. coli gltA strains growing on glucose must be supplemented with an intermediate of the TCA cycle such as glutamate.

Citrate synthase has been comprehensively studied, and crystal structures are established for ligand-free and ligand-bound forms of the enzyme from various organisms (Remington et al., 1982; Russell et al., 1994; Usher et al., 1995). Although the cofactor NADH does not play a direct role in the conversion, NADH is a strong and very specific allosteric inhibitor of citrate synthase, binding at a location remote from the active site (Weitzman, 1966; Weitzman and Danson, 1976). The elevated NADH concentration which normally exists at high growth rates or under anaerobic conditions at least partly explains the reduced flux through the TCA cycle under those conditions. Numerous studies on citrate synthase have explored the structure of the active sites and the NADH allosteric binding pocket (for example, Pereira et al., 1994; Stokell et al., 2003). The typical technique employed is to express and purify citrate synthases having point mutations at locations hypothesized to play a role in substrate and inhibitor binding, and then determine the effect of those mutations on kinetic parameters. Research has therefore demonstrated that H264, D362 and F383 are associated with the acetyl CoA binding pocket (Pereira et al., 1994). The effect of mutations in these or other residues in citrate synthase on E. coli growth and product formation has not been considered.

The goal of our study is to examine point mutations in citrate synthase to block the metabolic flux into the TCA cycle partially. We hypothesize that a reduction in citrate synthase activity would increase the intracellular pool of acetyl CoA and production of citramalate as an example product from acetyl CoA while allowing growth on glucose without supplementation of the TCA cycle intermediate glutamate.

Materials and Methods

Strain Construction

Strains used in this study are shown in Table 5. The Kan antibiotic marker was first removed from MEC568 (Parimi et al., 2017) to construct MEC569 using pCP20 (Datsenko and Wanner, 2000). Then, site-directed mutagenesis of gltA was performed using overlap extension PCR (OE-PCR) (Braman, 2010). The gltA variant sequences, including the native and the mutant sequences, were amplified using the primers listed in Table 6. For the kanamycin resistance cassette insertion, PCR products were amplified with the primers Kan-For and Kan-Rev, using pKD4 as a template (Datsenko and Wanner, 2000). The OE-PCR products, which were amplified with the primers gltA-Up-For and gltA-Down-Rev, contained 500 nt of sequence identical to the target locus upstream, the variant gltA gene, the kanamycin resistance cassette flanked by FRT (Flp recognition target) and 500 nt of sequence identical to the target locus downstream. The entire native gltA gene was replaced with different variants by transforming OE-PCR products into cells expressing λ Red recombinase proteins encoded on pKD46 (Datsenko and Wanner, 2000). The native gltA gene was reconstructed on-site with the adjacent kanamycin resistance cassette insertion downstream. Gene replacement was selected for on kanamycin plates and then verified by PCR with the primers gltA-Verif-For and gltA-Verif-Rev. Furthermore, the sequence of the gltA operon was confirmed for each mutant (Eurofins Scientific, Louisville, Ky., USA). The kanamycin cassette was left in the final mutant strains during the fermentation experiments. The plasmid pZE12-cimA containing a codon-optimized citramalate synthase was transformed into strains to examine citramalate production (Example 1).

mg/L ampicillin and/or 100 mg/L kanamycin were added as appropriate for plasmids/strains having antibiotic resistance.

Shake Flask, Batch and Fed-Batch Processes

For measuring specific growth rate of strains (i.e., not containing the pZE12-cimA plasmid), cells were first grown in 3 mL Lysogeny Broth (LB) at 37° C. and 250 rpm (19 mm pitch). After 12-16 h, 0.5 mL was used to inoculate triplicate 50 mL of XC medium in 500 mL baffled shake flasks growing at 37° C. and 250 rpm. The optical density at 600 nm (OD) (UV-650 spectrophotometer, Beckman Instru-

TABLE 5

Strains used in this study.

| Strain | Genotype | Ref |
|---|---|---|
| MEC568 | MG1655 ΔleuC778::(FRT) Δ(ackA778-pta-779)::(FRT) ΔpoxB772::Kan ΔgltA770::(FRT) | Parimi et al., 2017 |
| MEC569 | MG1655 ΔleuC778::(FRT) Δ(ackA778-pta-779)::(FRT) ΔpoxB772::(FRT) ΔgltA770::(FRT) | This study |
| MEC613 | MG1655 ΔleuC778::(FRT) Δ(ackA778-pta-779)::(FRT) ΔpoxB772::(FRT) ΔgltA770::gltA-Kan | This study |
| MEC624 | MG1655 ΔleuC778::(FRT) Δ(ackA778-pta-779)::(FRT) ΔpoxB772::(FRT) ΔgltA770::gltA-F383L-Kan | This study |
| MEC626 | MG1655 ΔleuC778::(FRT) Δ(ackA778-pta-779)::(FRT) ΔpoxB772::(FRT) ΔgltA770::gltA-F383M-Kan | This study |
| MEC648 | MG1655 ΔleuC778::(FRT) Δ(ackA778-pta-779)::(FRT) ΔpoxB772::(FRT) ΔgltA770::gltA-D362E-Kan | This study |
| MEC649 | MG1655 ΔleuC778::(FRT) Δ(ackA778-pta-779)::(FRT) ΔpoxB772::(FRT) ΔgltA770::gltA-F383I-Kan | This study |
| MEC654 | MG1655 ΔleuC778::(FRT) Δ(ackA778-pta-779)::(FRT) ΔpoxB772::(FRT) ΔgltA770::gltA-F383V-Kan | This study |

TABLE 6

Primers used in this study.

| Primer | Sequence | SEQ ID NO: |
|---|---|---|
| gltA-Up-For | 5'-TCATGCAAAACACTGCTTCCAGATG-3' | 14 |
| gltA-D362E | 5'-AGAGTAGAATTCGACGTTCGGGTACAG-3' | 15 |
| | 5'-TGTACCCGAACGTCGAATTCTACTCTG-3' | 16 |
| gltA-F383I | 5'-CGTGCCATTGCAATAATGACGGTGAAC-3' | 17 |
| | 5'-GTTCACCGTCATTATTGCAATGGCACG-3' | 18 |
| gltA-F383L | 5'-GCCATTGCCAGAATGACGGTGAACATG-3' | 19 |
| | 5'-CCGTCATTCTGGCAATGGCACGTACC-3' | 20 |
| gltA-F383M | 5'-GTGCCATTGCCATAATGACGGTGAACATG-3' | 21 |
| | 5'-CGTCATTATGGCAATGGCACGTAC-3' | 22 |
| gltA-F383V | 5'-GTGCCATTGCCACAATGACGGTGAAC-3' | 23 |
| | 5'-CGTCATTGTGGCAATGGCACGTAC-3' | 24 |
| gltA-Bot-R | 5'-GAAGCAGCTCCAGCCTACACCAACTTAGCAATCAACCATTAACGC-3' | 25 |
| Kan-For | 5'-GCGTTAATGGTTGATTGCTAAGTTGGTGTAGGCTGGAGCTGCTTC-3' | 26 |
| Kan-Rev | 5'-CATATGAACGGCGGGTTAAAATATTTAATGGGAATTAGCCATGGTCCATATG | 27 |
| gltA-Down-For | 5'-CATATGGACCATGGCTAATTCCCATTAAATATTTTAACCCGCCGTTCATATG | 28 |
| gltA-Down-Rev | 5'-GTTGTCGTGACTTGTCCAAGATCTATG-3' | 29 |
| gltA-Verif-For | 5'-ACTACGGGCACAGAGGTTAACTTTC-3' | 30 |
| gltA-Verif-Rev | 5'-CTGCCTCGTCCTGCAGTTCATTC-3' | 31 |

Growth Medium

XC medium contained (per L): 5.00 g glucose, 0.20 g/L L-leucine, 1.44 g $KH_2PO_4$, 2.11 g $K_2HPO_4$, 2.00 g $K_2SO_4$, 3.50 g $NH_4Cl$, 20.00 mg $Na_2(EDTA).2H_2O$, 0.15 g $MgSO_4.7H_2O$, 20 mg thiamine.HCl, 0.25 mg $ZnSO_4$, 0.125 mg $CuCl_2.2H_2O$, 1.25 mg $MnSO_4.H_2O$, 0.875 mg $CoCl_2.6H_2O$, 0.06 mg $H_3BO_3$, 0.25 mg $Na_2MoO_4.2H_2O$, 5.50 mg $FeSO_4.7H_2O$, and 20 mg citric acid. The medium was supplemented with 0.2 mM IPTG initially for strains which contained the pZE12-cimA plasmid. Additionally, 50 ments, San Jose, Calif., USA) was used to monitor cell growth of samples measured every 45 min. These shake flask cultures were harvested and analyzed for citrate synthase activity when the OD reached about 1. For other studies using strains harboring the pZE12-cimA plasmid, analogous procedures were performed except that the cultures were harvested at 24 h and analyzed for citramalate synthase activity, citramalate and intracellular acetyl CoA concentration.

For the comparison of strains under controlled bioreactor conditions, cells were grown as described above first in 3 mL LB and then in shake flasks with 50 mL XC medium. After 18 h the shake flask contents were used to inoculate a 2.5 L bioreactor (Bioflo 2000, New Brunswick Scientific Co., New Brunswick, N.J., USA) containing 1.0 L XC medium modified to contain 30 g/L glucose, 0.5 g/L L-leucine and 0.2 mM IPTG initially. The agitation was 400 rpm, and air was sparged at 1.0 L/min, which maintained the dissolved oxygen above 40% of saturation. The pH was controlled at 7.0 using 30% (w/v) KOH, and the temperature was controlled at 37° C. For fed-batch processes, the medium was modified to contain 1.5 g/L $NH_4Cl$, 30 g/L glucose, 0.5 g/L L-leucine and 0.2 mM IPTG initially. Also, a solution of 300 g/L $NH_4Cl$ was fed in an exponential fashion to maintain the cell growth rate of 0.15 $h^{-1}$ after OD reached about 3 and a total volume of 30 mL was added. A 50 mL volume containing 30 g glucose and 0.5 g L-leucine were added four times when the glucose concentration decreased below 5 g/L. The batch and fed-batch processes were completed in duplicate.

Analytical Methods

Extracellular organic acids were analyzed by HPLC using a Refractive Index detector as previously described (Eiteman and Chastain, 1997). Glutamate concentration was measured using a glutamate assay kit (Sigma-Aldrich Co., St. Louis, Mo., USA), and intracellular acetyl CoA was analyzed by the previously established method (Gao et al., 2007). For dry cell weight (DCW) measurement, three 25.0 mL samples were centrifuged (3300×g, 10 min), the pellets washed by vortex mixing with 10 mL DI water and then centrifuged again. After washing three times, the cell pellets were dried at 60° C. for 24 h and weighed.

Cell-free extracts were prepared using French press and used to measure citramalate synthase activity and citrate synthase activity by the generation of free CoA and its reaction product with 5,5'-dithiobis(2-nitrobenzoic acid) detected at a wavelength of 412 nm (Srere et al., 1963; Howell et al., 1999). One Unit of activity is the amount of enzyme that generates one μmole of CoA in one minute at 37° C.

Results

Strain Construction

Citramalate synthase (coded by the cimA gene) catalyzes the conversion of pyruvate and acetyl CoA to citramalate. A knockout in the gltA coding for citrate synthase elevated the intracellular acetyl CoA level and correspondingly enhanced the citramalate production in E. coli (Example 1). However, L-glutamate was a required nutrient for cell growth in the gltA strain. In order to eliminate the glutamate requirement but maintain an elevated intracellular concentration of acetyl CoA, several single-residue point mutations were introduced into the chromosomal citrate synthase of E. coli leuC ackA-pta pox B. Specifically, five different single point mutations were compared, which were associated with the acetyl CoA binding site on citrate synthase (Table 5), resulting in the following strains (sequence change): MEC613 (native gltA reintroduced), MEC624 (F383L), MEC626 (F383M), MEC649 (F383I), MEC654 (F383V), and MEC648 (D362E).

Growth and Enzyme Activity in Shake Flasks

Figure 19:
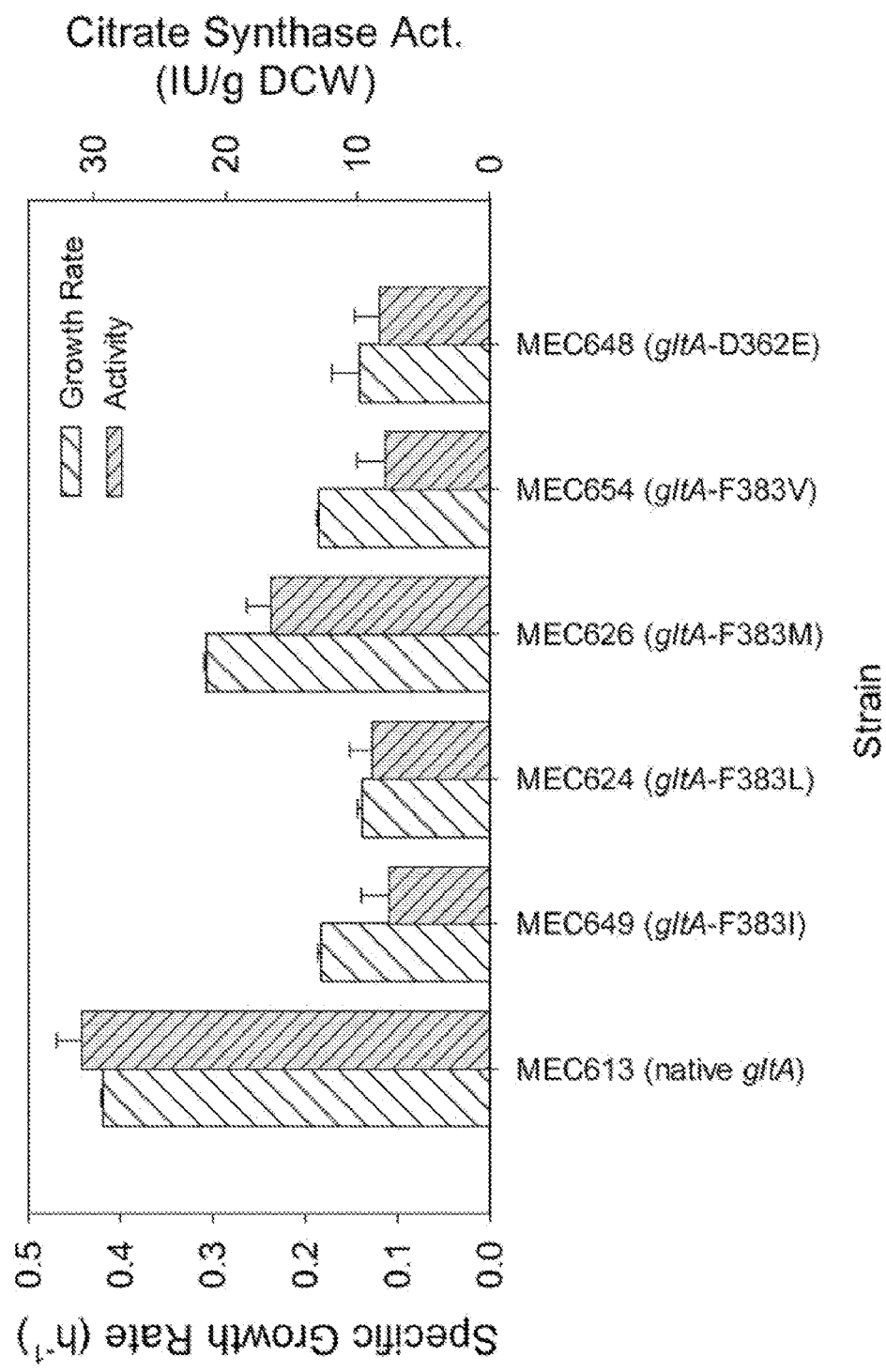
FIG. 19 shows comparison of specific growth rate and citrate synthase activity using various strains of *E. coli* leuC ackA-pta poxB containing point mutations in citrate synthase coded by the gltA gene. MEC613 contains the wild-type gltA gene. All results represent triplicate shake flask experiments.

Using these six strains (the native gltA-containing strain and five with point mutations), we examined the specific growth rate using 5 g/L glucose as the sole carbon source (FIG. 19). Each strain differed in the citrate synthase sequence only, and all contained knockouts in the leuC ackA-pta poxB knockouts. Each citrate synthase point-mutation strain was able to grow without the addition of glutamate. MEC613 with native citrate synthase showed a maximum specific growth rate of about 0.42 $h^{-1}$. Among the point-mutation strains, MEC626 (F383M) achieved the highest growth rate of 0.31 $h^{-1}$, while the other four strains attained growth rates in the range of 0.13-0.19 $h^{-1}$. Citrate synthase activity measured during the exponential phase correlated closely with growth rate: MEC613 showed a citrate synthase activity over 30 IU/g DCW, while MEC626 displayed the next greatest citrate synthase activity of 17 IU/g DCW. The citrate synthase activities were 8-10 IU/g DCW among the other four point-mutation strains. These results conclusively show that the growth rate of strains is reduced by introducing point mutations into citrate synthase.

Citramalate Formation in Shake Flasks

Figure 20:
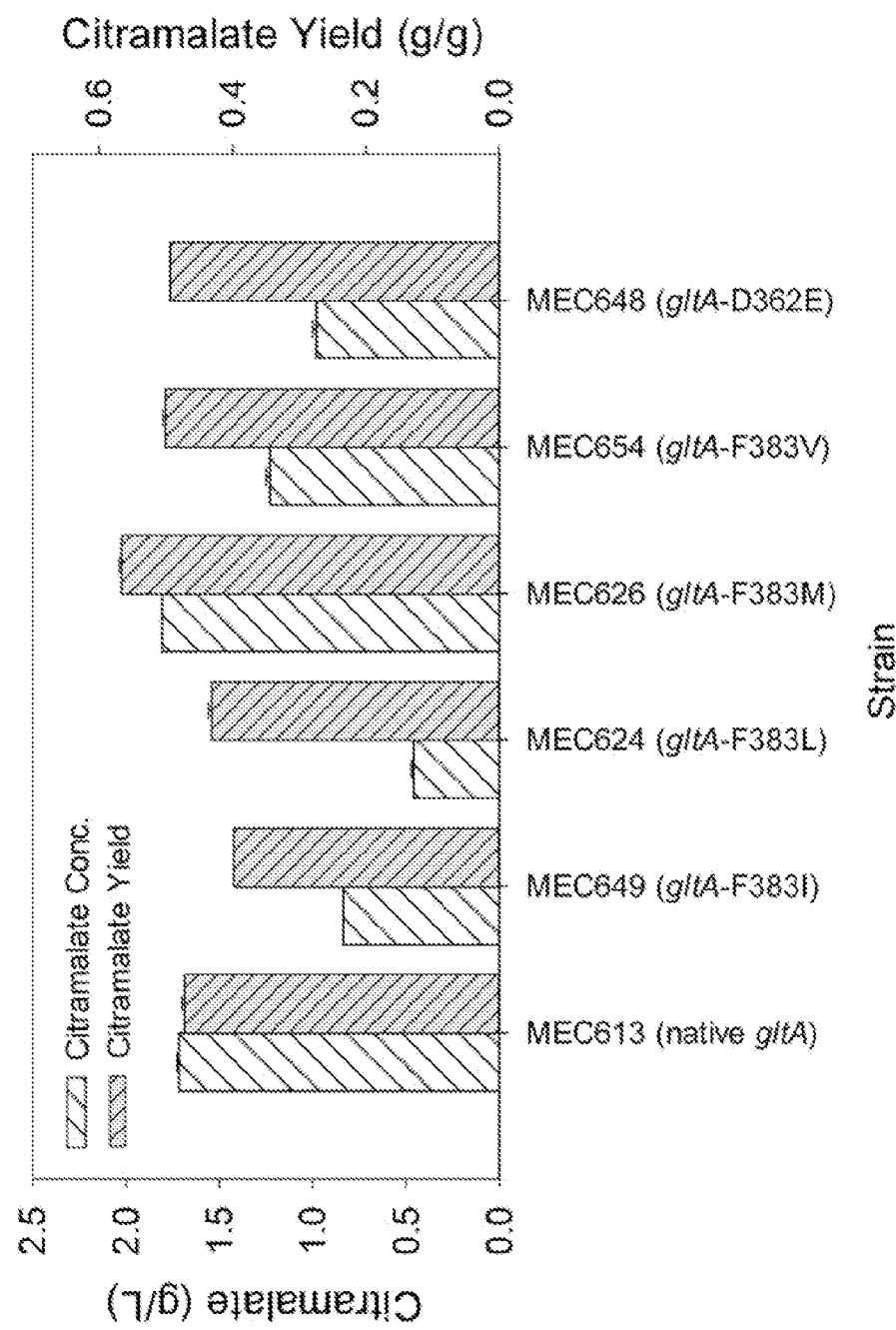
FIG. 20 shows comparison of citramalate concentration and citramalate yield from 5 g/L glucose in various strains of *E. coli* leuC ackA-pta poxB containing point mutations in citrate synthase coded by the gltA gene. MEC613 contains the wild-type gltA gene. All strains contained the pZE12-cimA plasmid expressing citramalate synthase and were induced initially with 0.2 mM IPTG.

We next investigated 24 h citramalate production in defined medium containing 5 g/L glucose using the E. coli strains overexpressing citramalate synthase coded by the cimA gene (FIG. 20). MEC613/pZE12-cimA with native citrate synthase generated 1.72 g/L citramalate with a yield of 0.47 g/g glucose. Four of the point-mutation strains MEC624, MEC648, MEC649 or MEC654 harboring the plasmid pZE12-cimA each accumulated 30%-70% less citramalate concentration than MEC613/pZE12-cimA. Despite the lower citramalate titer, the citramalate yields for these four mutant strains were 0.40 g/g or greater. The lower citramalate concentration is attributed to the lower growth rate (FIG. 19) and incomplete utilization of glucose over 24 h. For MEC626/pZE12-cimA, 1.81 g/L citramalate accumulated with a yield of 0.57 g/g. Despite the citrate synthase mutation (F383M) and exhibiting slower growth, these cells generated more citramalate than the strain containing the native citrate synthase in shake flasks. Citramalate synthase activity was also measured in all shake flasks studied and were not affected by citrate synthase mutation (data not shown).

Citramalate Formation in Controlled Batch Conditions

Figure 21:
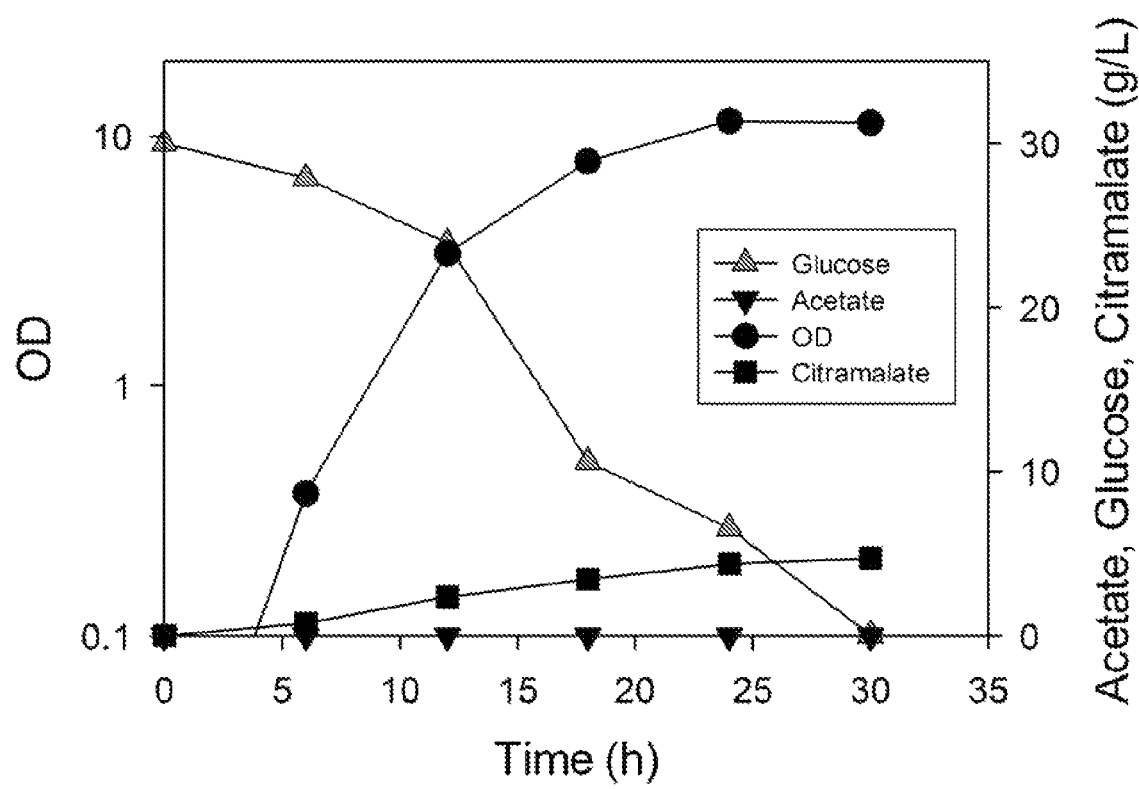
FIG. 21 shows citramalate production using 30 g/L in a 1.0 L batch fermentation with MEC613/pZE12-cimA. MEC613 contains the wild-type gltA gene.
Figure 22:
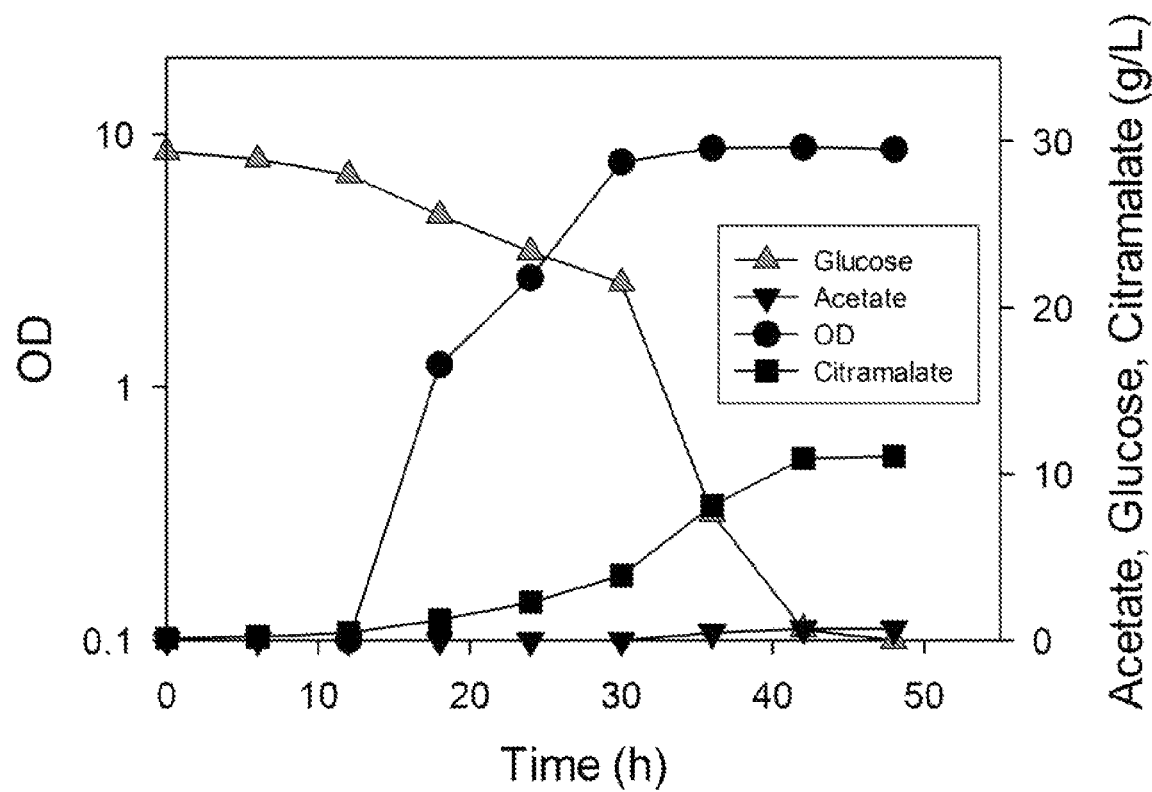
FIG. 22 shows citramalate production using 30 g/L in a 1.0 L batch fermentation with MEC626/pZE12-cimA. MEC626 contains the F383M point mutation in the gltA gene.

We next compared citramalate production by MEC613/pZE12-cimA and MEC626/pZE12-cimA under controlled batch conditions using defined medium with 30 g/L glucose as the sole carbon source. MEC613/pZE12-cimA reached an OD of 8.5 in only 18 h, and by 30 h had accumulated 4.9 g/L citramalate with no detectable acetate (FIG. 21). In contrast, MEC626/pZE12-cimA reached an OD of 7.8 in 30 h, and accumulated 11 g/L citramalate and 0.75 g/L acetate in 48 h (FIG. 22). During the growth of these strains, the potential by-products succinate, lactate, ethanol and pyruvate were not detected. The F383M mutation in citrate synthase more than doubled the citramalate yield on glucose from 0.16 g/g (MEC613/pZE12-cimA) to 0.37 g/g (MEC626/pZE12-cimA). Moreover, because the activity of citrate synthase was reduced but not eliminated, a TCA cycle intermediate such as glutamate was not a required component of the medium.

Exponential Fed-Batch Fermentation

Figure 23:
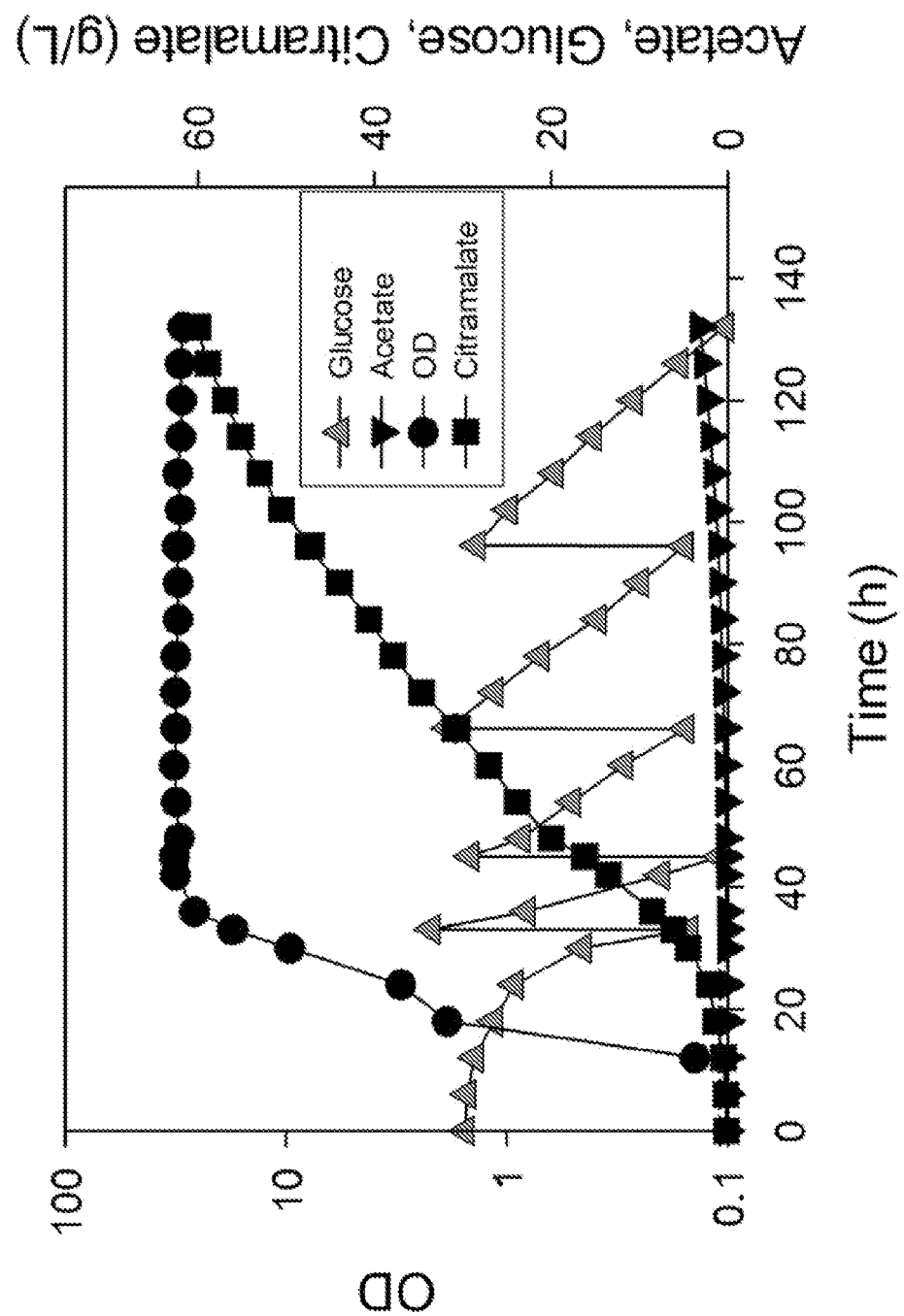
FIG. 23 shows citramalate production using 30 g/L in a 1.0 L fed-batch fermentation with MEC626/pZE12-cimA. Approximately 30 g glucose was added four times to the fermenter when the glucose concentration decreased below 5 g/L. MEC626 contains the F383M point mutation in the gltA gene.

To increase the citramalate titer and yield, we designed fed-batch experiments with an exponential feed strategy using nitrogen ($NH_4Cl$) as the growth limiting resource. Additionally, approximately 30 g glucose was added four times to the fermenter when the glucose concentration decreased below 5 g/L. For these fed-batch processes the OD reached 32 within 42 h at which time the citramalate concentration was 13.5 g/L (FIG. 23). After 132 h, the citramalate concentration reached an average of 60 g/L with a yield of 0.53 g/g glucose. Despite the ackA-pta poxB gene deletions and the aerobic conditions, 3.1 g/L acetate and 1.3 g/L lactate were formed as by-products (latter not shown).

REFERENCES

H. Alper, C. Fischer, E. Nevoigt, G. Stephanopoulos, 2005. Tuning genetic control through promoter engineering. Proc Natl Acad Sci USA. 102, 12678-12683.

J. Anfelt, D. Kaczmarzyk, K. Shabestary, B. Renberg, J. Rockberg, J. Nielsen, M. Uhlén, E. P. Hudson, 2015. Genetic and nutrient modulation of acetyl-CoA levels in *synechocystis* for n-butanol production. Microb. Cell Fact. 14, 167.

Arya, A. S., Lee, S. A., Eiteman, M. A., 2013. Differential sensitivities of the growth of *Escherichia coli* to acrylate under aerobic and anaerobic conditions and its effect on product formation. Biotechnol. Lett. 35, 1839-1843.

Bauer, W. Jr., 2000. Methacrylic acid and derivatives. Ullmann's Encyclopedia of Industrial Chemistry. Wiley-VCH, Weinheim.

R. R. Bommareddy, Z. Chen, S. Rappert, A.-P. Zeng, 2014. A de novo NADPH generation pathway for improving lysine production of *Corynebacterium glutamicum* by rational design of the coenzyme specificity of glyceraldehyde 3-phosphate dehydrogenase. Metab. Eng. 25, 30-37

J. Braman, 2010. In Vitro Mutagenesis Protocols: Third Edition. Humana Press. Totowa, N.J.

S. Centeno-Leija, G. Huerta-Beristain, M. Giles-Gómez, F. Bolivar, G. Gosset, A. Martinez, 2014. Improving poly-3-hydroxybutyrate production in *Escherichia coli* by combining the increase in the NADPH pool and acetyl-CoA availability. Ant. van Leeuw. 105, 687-696.

Z. Chen, Y. Wu, J. Huang, D. Liu, 2015. Metabolic engineering of *Klebsiella pneumoniae* for the de novo production of 2-butanol as a potential biofuel. Bioresour Technol. 197, 260-265.

J. W. Choi, N. A. Da Silva, 2014. Improving polyketide and fatty acid synthesis by engineering of the yeast acetyl-CoA carboxylase. J. Biotechnol. 187, 56-59.

Datsenko, K. A., Wanner, B. L., 2000. One-step inactivation of chromosomal genes in *Escherichia coli* K-12 using PCR products. Proc. Natl. Acad. Sci. U.S.A 97, 6640-6645.

C. R. Dittrich, R. V. Vadali, G. N. Bennett, K.-Y. San. 2005. Redistribution of metabolic fluxes in the central aerobic metabolic pathway of *E. coli* mutant strains with deletion of the ackA-pta and poxB pathways for the synthesis of isoamyl acetate. Biotechnol. Prog. 21, 627-631.

Eiteman, M. A., Chastain, M. J., 1997. Optimization of the ion-exchange analysis of organic acids from fermentation. Anal. Chim. Acta. 338, 69-75.

Gao, L., Chiou, W., Tang, H., Cheng, X., Camp, H. S., Burns, D. J., 2007. Simultaneous quantification of malonyl-CoA and several other short-chain acyl-CoAs in animal tissues by ion-pairing reversed-phase HPLC/MS. J. Chromatogr. B. 853, 303-313.

M. He, D. Wu, J. Wu, J. Chen. 2014. Enhanced expression of endoinulinase from *Aspergillus niger* by codon optimization in *Pichia pastoris* and its application in inulooligosaccharide production. J Ind Microbiol Biotechnol. 41, 105-114.

Howell, D. M., Xu, H., White, R. H., 1999. (R)-Citramalate synthase in *Methanogenic archaea*. J. Bacteriol. 181, 331-333.

Johnson, D. W., Eastham, G. R., Poliakoff, M., Huddle, T. A., 2015. Method of producing acrylic and methacrylic acid. U.S. Pat. No. 8,933,179 B2.

T. M. Lakshmi, R. B. Helling. 1976. Selection for citrate synthase deficiency in icd mutants of *Escherichia coli*. J. Bacteriol. 127, 76-83.

S. Y. Lee, H. U. Kim, 2015. Systems strategies for developing industrial microbial 427 strains. Nat Biotechnol, 33, 1061-1072.

E. Leonard, P. K. Ajikumar, K. Thayer, W.-H. Xiao, J. D. Mo, B. Tidor, G. Stephanopoulos, K. L. J. Prather, 2010. Combining metabolic and protein engineering of a terpenoid biosynthetic pathway for overproduction and selectivity control. Proc Natl Acad Sci USA 107, 13654-13659.

J. C. Liang, R. J. Bloom, C. D. Smolke, 2011. Engineering biological systems with synthetic RNA molecules. Mol. Cell 43, 915-926.

X. Lv, F. Wang, P. Zhou, L. Ye, W. Xie, H. Xu, H. Yu, 2016. Dual regulation of cytoplasmic and mitochondrial acetyl-CoA utilization for improved isoprene production in *Saccharomyces cerevisiae*. Nat. Commun. 7, 12851.

H. B. Machado, Y. Dekishima, H. Luo, E. I. Lan, J. C. Liao, 2012. A selection platform for carbon chain elongation using the CoA-dependent pathway to produce linear higher alcohols. Metab Eng. 14, 504-511.

Nagai, K., 2001. New developments in the production of methyl methacrylate. Appl. Catal. A-Gen. 221, 367-377.

K. B. Otte, B. Hauer, 2015. Enzyme engineering in the context of novel pathways and products. *Curr. Opin. Biotechnol.* 35, 16-22.

N. S. Parimi, I. A. Durie, X. Wu, M. A. Eiteman, 2017, Eliminating acetate formation improves citramalate production by metabolically engineered *Escherichia coli*.

D. S. Pereira, L. J. Donald, D. J. Hosfield, H. W. Duckworth. 1994. Active site mutants of *Escherichia coli* citrate synthase. J. Biol. Chem. 269(1):412-417.

E. M. Quandt, J. Gollihar, Z. D. Blount, A. D. Ellington, G. Georgiou, J. E. Barrick, 2015. Fine-tuning citrate synthase flux potentiates and refines metabolic innovation in the Lenski evolution experiment. eLife. 4, e09696.

H. M. Salis, E. A. Mirsky, C. A. Voigt, 2009. Automated design of synthetic ribosome binding sites to control protein expression. Nat Biotechnol. 27, 946-950.

Salkind, M., Riddle, E. H., Keefer, R. W., 1959. Acrylates and methacrylates—raw materials, intermediates, and plant integration. Ind. Eng. Chem. 51, 1232-1238.

P. A. Srere, H. Brazil, L. Gonen. 1963. The citrate condensing enzyme of pigeon breast muscle and moth flight muscle. Acta Chem. Scand. 17, S129-S134.

D. J. Stokell, L. J. Donald, R. Maurus, N. T. Nguyen, G. Sadler, K. Choudhary, P. G. Hultin, G. D. Brayer, H. W. Duckworth. 2003. Probing the roles of key residues in the unique regulatory NADH binding site of type II citrate synthase of *Escherichia coli*. J. Biol. Chem. 278, 35435-35443.

Todd, J. D., Curson, A. R. J., Sullivan, M. J., Kirkwood, M., Johnston, A. W. B., 2012. The *Ruegeria pomeroyi* acuI gene has a role in DMSP catabolism and resembles yhdH of *E. coli* and other bacteria in conferring resistance to acrylate. PLoS ONE. 7, e35947.

P. D. J. Weitzman. 1966. Regulation of citrate synthase activity in *Escherichia coli*. Biochim. Biophys. Acta 128, 213-215.

P. D. J. Weitzman, M. J. Danson. 1976. Citrate synthase. Curr. Topics Cell Regul. 10, 161-204.

Wu, X., Eiteman, M. A., 2016. Production of citramalate by metabolically engineered *Escherichia coli*. Biotechnol. Bioeng. 113, 2670-2675.

Y. Yoshikuni, J. A. Dietrich, F. F. Nowroozi, P. C. Babbitt, J. D. Keasling, 2008. Redesigning enzymes based on adaptive evolution for optimal function in synthetic metabolic pathways. *Chem Biol.* 15, 607-618.

Zhang, K., Woodruff, A. P., Xiong, M., Zhou, J., Dhande, Y. K., 2011. A synthetic metabolic pathway for production of the platform chemical isobutyric acid. ChemSusChem, 4, 1068-1070.

J. Zhao, T. Baba, H. Mori, K. Shimizu. 2004. Effect of zwf gene knockout on the metabolism of *Escherichia coli* grown on glucose or acetate. Metab. Eng. 6, 164-174.

N. Zhu, H. Xia, Z. Wang, X. Zhao, T. Chen, 2013. Engineering of acetate recycling and citrate synthase to improve aerobic succinate production in *Corynebacterium glutamicum*. PLOS ONE. 8, 4.

EXEMPLARY EMBODIMENTS

Embodiment 1

A genetically engineered microbe which accumulates citramalate,
wherein the microbe comprises a first exogenous polynucleotide encoding a citramalate synthase which catalyzes the condensation of acetyl CoA and pyruvic acid, and
wherein the microbe comprises a second exogenous polynucleotide encoding a citrate synthase which catalyzes the condensation of acetyl CoA and oxaloacetate, and the citrate synthase activity in the microbe is reduced compared to a control microbe.

Embodiment 2

The genetically engineered microbe of Embodiment 1 wherein the citrate synthase encoded by the second exogenous polynucleotide comprises at least one amino acid substitution, wherein the one amino acid substitution is associated with the reduced citrate synthase activity.

Embodiment 3

The genetically engineered microbe of any of Embodiments 1-2 wherein the second exogenous polynucleotide is present in the chromosome.

Embodiment 4

The genetically engineered microbe of any of Embodiments 1-3 wherein the at least one amino acid substitution is an amino acid associated with the acetyl-CoA binding pocket, the mobile loop, the NADH binding site, and the oxaloacetate binding site, or a combination thereof.

Embodiment 5

The genetically engineered microbe of any of Embodiments 1-4 wherein the at least one amino acid substitution is at a position functionally equivalent to F383, D362, R407, H229, R314, R387, A123, A257, A258, A161, or a combination thereof, of an *E. coli* citrate synthase, such as SEQ ID NO:5.

Embodiment 6

The genetically engineered microbe of any of Embodiments 1-5
wherein the substitution of the amino acid at a position functionally equivalent to F383 is F383I, F383M, F383L, F383V, F383A, F383Y, or F383K,
wherein the substitution of the amino acid at a position functionally equivalent to D362 is D362V, D362I, or D362E,
wherein the substitution of the amino acid at a position functionally equivalent to A123 is A123T,
wherein the substitution of the amino acid at a position functionally equivalent to A257 is A257T,
wherein the substitution of the amino acid at a position functionally equivalent to A258 is A258T, and
wherein the substitution of the amino acid at a position functionally equivalent to A161 is A161V Embodiment 7

The genetically engineered microbe of any of Embodiments 1-6 wherein the microbe is *E. coli*.

Embodiment 8

The genetically engineered microbe of any of Embodiments 1-7 wherein the citrate synthase catalyzes the condensation of acetyl CoA and oxaloacetate at a rate that is less than the rate of condensation by the wild type citrate synthase naturally present in the microbe.

Embodiment 9

The genetically engineered microbe of any of Embodiments 1-8 wherein the microbe expresses a reduced amount of a citrate synthase protein compared to the control microbe.

Embodiment 10

The genetically engineered microbe of any of Embodiments 1-9 wherein the microbe produces least 2.5 g/L citramalate in 30 hours based on batch culture conditions.

Embodiment 11

The genetically engineered microbe of any of Embodiments 1-10 wherein the carbon source is glucose, and the citramalate yield is at least 0.14 g/g.

Embodiment 12

The genetically engineered microbe of any of Embodiments 1-9 wherein the microbe produces least 35 g/L in 132 hours based on fed-batch culture conditions.

Embodiment 13

The genetically engineered microbe of any of Embodiments 1-12 wherein the carbon source is glucose, and the citramalate yield is at least 0.4 g/g.

Embodiment 14

The genetically engineered microbe of any of Embodiments 1-19 wherein the microbe further comprises reduced expression of a coding region encoding a protein that converts pyruvate to acetate.

Embodiment 15

The genetically engineered microbe of any of Embodiments 1-20 wherein the coding region encoding the protein that converts pyruvate to acetate is a pyruvate oxidase.

Embodiment 16

The genetically engineered microbe of any of Embodiments 1-21 wherein the microbe further comprises reduced expression of a coding region encoding a protein that converts acetyl CoA to acetate-phosphate.

Embodiment 17

The genetically engineered microbe of any of Embodiments 1-22 wherein the coding region encoding the protein that converts acetyl CoA to acetate-phosphate is a phosphotransacetylase.

Embodiment 18

The genetically engineered microbe of any of Embodiments 1-15 wherein the microbe further comprises reduced expression of a coding region encoding a protein that converts acetate-phosphate to acetate.

Embodiment 19

The genetically engineered microbe of any of Embodiments 1-16 wherein the coding region encoding the protein that converts acetate-phosphate to acetate is an acetate kinase.

Embodiment 20

The genetically engineered microbe of any of Embodiments 1-19 wherein the microbe further comprises reduced expression of a coding region encoding a protein that converts citramalate to citraconate.

Embodiment 21

The genetically engineered microbe of any of Embodiments 1-20 wherein the coding region encoding the protein that converts citramalate to citraconate is a 3-isopropylmalate dehydratase.

Embodiment 22

The genetically engineered microbe of any of Embodiments 1-21 wherein the microbe further comprises reduced expression of a coding region encoding a protein that converts acetyl CoA to malate.

Embodiment 23

The genetically engineered microbe of any of Embodiments 1-22 wherein the coding region encoding the protein that converts acetyl CoA to malate is a malate synthase.

Embodiment 24

The genetically engineered microbe of any of Embodiments 1-23 wherein the microbe further comprises reduced expression of a coding region encoding a protein that converts pyruvate to lactate.

Embodiment 25

The genetically engineered microbe of any of Embodiments 1-24 wherein the coding region encoding the protein that converts pyruvate to lactate is a lactate dehydrogenase A.

Embodiment 26

The genetically engineered microbe of any of Embodiments 1-25 wherein the reduced expression comprises deletion of the coding region.

Embodiment 27

The genetically engineered microbe of any of Embodiments 1-26 wherein the reduced expression comprises inactivation of the coding region.

Embodiment 28

A genetically engineered microbe which accumulates citramalate wherein the microbe comprises an exogenous polynucleotide encoding a citramalate synthase which catalyzes the condensation of acetyl CoA and pyruvic acid, and wherein the microbe produces at least 20 grams citramalate per liter (g/L), at least 30 g/L, or at least 40 g/L.

Embodiment 29

The genetically engineered microbe of Embodiment 28 wherein the conditions for producing at least 20 grams citramalate per liter (g/L), at least 30 g/L, or at least 40 g/L comprise a fed-batch process.

Embodiment 30

The genetically engineered microbe of any of Embodiments 28-29 wherein the microbe further comprises reduced expression of a coding region encoding a protein that converts acetyl CoA to citrate.

Embodiment 31

The genetically engineered microbe of any of Embodiments 28-30 wherein the coding region encoding the protein that converts acetyl CoA to citrate is a citrate synthase

Embodiment 32

The genetically engineered microbe of any of Embodiments 28-31 wherein the citrate synthase is gltA.

Embodiment 33

The genetically engineered microbe of any of Embodiments 28-32 wherein the microbe further comprises reduced expression of a coding region encoding a protein that converts acetyl CoA to malate.

Embodiment 34

The genetically engineered microbe of any of Embodiments 28-33 wherein the coding region encoding the protein that converts acetyl CoA to malate is glcB or aceB.

Embodiment 35

The genetically engineered microbe of any of Embodiments 28-34 wherein the microbe further comprises reduced expression of a coding region encoding a protein that converts acetate-phosphate to acetate.

Embodiment 36

The genetically engineered microbe of any of Embodiments 28-35 wherein the coding region encoding the protein that converts acetate-phosphate to acetate is ackA.

Embodiment 37

The genetically engineered microbe of any of Embodiments 28-36 wherein the microbe further comprises reduced expression of a coding region encoding a protein that converts pyruvate to lactate.

Embodiment 38

The genetically engineered microbe of any of Embodiments 28-37 wherein the coding region encoding the protein that converts pyruvate to lactate is ldhA.

Embodiment 39

A method for producing citramalate comprising:
culturing the microbe of any of Embodiments 1-38 under suitable conditions result in the production of citramalate.

Embodiment 40

The method of Embodiment 39 wherein the suitable conditions comprise use of glucose, glycerol, or a combination thereof, as a carbon source.

Embodiment 41

The method of any of Embodiments 39-40 further comprising isolating the citramalate from the microbe or the culture medium, or the combination thereof.

Embodiment 42

The method of any of Embodiments 39-41 further comprising chemically synthesizing methacrylic acid from the citramalate.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A genetically engineered microbe which accumulates citramalate,
   wherein the microbe comprises a first exogenous polynucleotide encoding a citramalate synthase which catalyzes the condensation of acetyl CoA and pyruvic acid, and
   wherein the microbe comprises a second exogenous polynucleotide encoding a citrate synthase which catalyzes the condensation of acetyl CoA and oxaloacetate, and the citrate synthase activity in the microbe is reduced compared to a control microbe.

2. The genetically engineered microbe of claim 1 wherein the second exogenous polynucleotide is present in the chromosome.

3. The genetically engineered microbe of claim 1 wherein the citrate synthase encoded by the second exogenous polynucleotide comprises at least one amino acid substitution, wherein the at least one amino acid substitution is associated with the reduced citrate synthase activity, and wherein the at least one amino acid substitution is an amino acid associated with the acetyl-CoA binding pocket, the mobile loop, the NADH binding site, the oxaloacetate binding site, or a combination thereof.

4. The genetically engineered microbe of claim 1 wherein the citrate synthase encoded by the second exogenous polynucleotide comprises at least one amino acid substitution, wherein the at least one amino acid substitution is associated with the reduced citrate synthase activity, and wherein the at least one amino acid substitution is at a position functionally equivalent to F383, D362, R407, H229, R314, R387, A123, A257, A258, A161, or a combination thereof, of SEQ ID NO:5.

5. The genetically engineered microbe of claim 4
   wherein the substitution of the amino acid at a position functionally equivalent to F383 is F383I, F383M, F383L, F383V, F383A, F383Y, or F383K,
   wherein the substitution of the amino acid at a position functionally equivalent to D362 is D362V, D362I, or D362E,
   wherein the substitution of the amino acid at a position functionally equivalent to A123 is A123 T,
   wherein the substitution of the amino acid at a position functionally equivalent to A257 is A257T,
   wherein the substitution of the amino acid at a position functionally equivalent to A258 is A258T,
   wherein the substitution of the amino acid at a position functionally equivalent to A161 is A161V, or a combination thereof.

6. The genetically engineered microbe of claim 1 wherein the microbe is *E. coli*.

7. The genetically engineered microbe of claim 1 wherein the citrate synthase catalyzes the condensation of acetyl CoA and oxaloacetate at a rate that is less than the rate of condensation by the wild type citrate synthase naturally present in the microbe.

8. The genetically engineered microbe of claim 1 wherein the microbe produces at least 2.5 g/L citramalate in 30 hours based on batch culture conditions.

9. The genetically engineered microbe of claim 1 wherein the microbe produces at least 35 g/L in 132 hours based on fed-batch culture conditions.

10. The genetically engineered microbe of claim 9 wherein the carbon source is glucose, and the citramalate yield is at least 0.4 g/g.

11. The genetically engineered microbe of claim 1 wherein the microbe further comprises reduced expression of a coding region encoding a protein that converts pyruvate to acetate compared to the control microbe.

12. The genetically engineered microbe of claim 11 wherein the microbe further comprises reduced expression of a coding region encoding a protein that converts acetate-phosphate to acetate compared to the control microbe.

13. The genetically engineered microbe of claim 1 wherein the microbe further comprises reduced expression of a coding region encoding a protein that converts acetyl CoA to acetate-phosphate compared to the control microbe.

14. A method for producing citramalate comprising:
culturing the microbe of claim 1 under suitable conditions resulting in the production of citramalate.

15. The genetically engineered microbe of claim 1 wherein the microbe expresses a reduced amount of a citrate synthase protein compared to the control microbe.

16. The genetically engineered microbe of claim 11 wherein the coding region encoding the protein that converts pyruvate to acetate is a pyruvate oxidase.

17. The genetically engineered microbe of claim 12 wherein the coding region encoding the protein that converts acetate-phosphate to acetate is an acetate kinase.

18. The genetically engineered microbe of claim 13 wherein the coding region encoding the protein that converts acetyl CoA to acetate-phosphate is a phosphotransacetylase.

19. The method of claim 14 wherein the suitable conditions comprise use of glucose, glycerol, or a combination thereof, as a carbon source.

20. The method of claim 14 further comprising chemically synthesizing methacrylic acid from the citramalate.

* * * * *

SEQUENCE LISTING

```
<160> NUMBER OF SEQ ID NOS: 31

<210> SEQ ID NO 1
<211> LENGTH: 491
<212> TYPE: PRT
<213> ORGANISM: Methanococcus jannaschii

<400> SEQUENCE: 1

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Ile Thr
        35                  40                  45

Ser Lys Gly Glu Arg Glu Gly Ile Lys Leu Ile Thr Lys Glu Gly Leu
    50                  55                  60

Asn Ala Glu Ile Cys Ser Phe Val Arg Ala Leu Pro Val Asp Ile Asp
```

```
                65                  70                  75                  80
            Ala Ala Leu Glu Cys Asp Val Asp Ser Val His Leu Val Val Pro Thr
                            85                  90                  95
            Ser Pro Ile His Met Lys Tyr Lys Leu Arg Lys Thr Glu Asp Glu Val
                            100                 105                 110
            Leu Glu Thr Ala Leu Lys Ala Val Glu Tyr Ala Lys Glu His Gly Leu
                            115                 120                 125
            Ile Val Glu Leu Ser Ala Glu Asp Ala Thr Arg Ser Asp Val Asn Phe
                            130                 135                 140
            Leu Ile Lys Leu Phe Asn Glu Gly Lys Val Gly Ala Asp Arg Val
            145                 150                 155                 160
            Cys Val Cys Asp Thr Val Gly Val Leu Thr Pro Gln Lys Ser Gln Glu
                            165                 170                 175
            Leu Phe Lys Lys Ile Thr Glu Asn Val Asn Leu Pro Val Ser Val His
                            180                 185                 190
            Cys His Asn Asp Phe Gly Met Ala Thr Ala Asn Thr Cys Ser Ala Val
                            195                 200                 205
            Leu Gly Gly Ala Val Gln Cys His Val Thr Val Asn Gly Ile Gly Glu
                            210                 215                 220
            Arg Ala Gly Asn Ala Ser Leu Glu Glu Val Val Ala Ala Leu Lys Ile
            225                 230                 235                 240
            Leu Tyr Gly Tyr Asp Thr Lys Ile Lys Met Glu Lys Leu Tyr Glu Val
                            245                 250                 255
            Ser Arg Ile Val Ser Arg Leu Met Lys Leu Pro Val Pro Asn Lys
                            260                 265                 270
            Ala Ile Val Gly Asp Asn Ala Phe Ala His Glu Ala Gly Ile His Val
                            275                 280                 285
            Asp Gly Leu Ile Lys Asn Thr Glu Thr Tyr Glu Pro Ile Lys Pro Glu
                            290                 295                 300
            Met Val Gly Asn Arg Arg Arg Ile Ile Leu Gly Lys His Ser Gly Arg
            305                 310                 315                 320
            Lys Ala Leu Lys Tyr Lys Leu Asp Leu Met Gly Ile Asn Val Ser Asp
                            325                 330                 335
            Glu Gln Leu Asn Lys Ile Tyr Glu Arg Val Lys Glu Phe Gly Asp Leu
                            340                 345                 350
            Gly Lys Tyr Ile Ser Asp Ala Asp Leu Leu Ala Ile Val Arg Glu Val
                            355                 360                 365
            Thr Gly Lys Leu Val Glu Glu Lys Ile Lys Leu Asp Glu Leu Thr Val
                            370                 375                 380
            Val Ser Gly Asn Lys Ile Thr Pro Ile Ala Ser Val Lys Leu His Tyr
            385                 390                 395                 400
            Lys Gly Glu Asp Ile Thr Leu Ile Glu Thr Ala Tyr Gly Val Gly Pro
                            405                 410                 415
            Val Asp Ala Ala Ile Asn Ala Val Arg Lys Ala Ile Ser Gly Val Ala
                            420                 425                 430
            Asp Ile Lys Leu Val Glu Tyr Arg Val Glu Ala Ile Gly Gly Gly Thr
                            435                 440                 445
            Asp Ala Leu Ile Glu Val Val Lys Leu Arg Lys Gly Thr Glu Ile
                            450                 455                 460
            Val Glu Val Arg Lys Ser Asp Ala Asp Ile Ile Arg Ala Ser Val Asp
            465                 470                 475                 480
            Ala Val Met Glu Gly Ile Asn Met Leu Leu Asn
                            485                 490
```

<210> SEQ ID NO 2
<211> LENGTH: 528
<212> TYPE: PRT
<213> ORGANISM: Geobacter sulfurreducens

<400> SEQUENCE: 2

Met Ser Leu Val Lys Leu Tyr Asp Thr Thr Leu Arg Asp Gly Thr Gln
1               5                   10                  15

Ala Glu Asp Ile Ser Phe Leu Val Glu Asp Lys Ile Arg Ile Ala His
            20                  25                  30

Lys Leu Asp Glu Ile Gly Ile His Tyr Ile Glu Gly Gly Trp Pro Gly
        35                  40                  45

Ser Asn Pro Lys Asp Val Ala Phe Phe Lys Asp Ile Lys Lys Glu Lys
    50                  55                  60

Leu Ser Gln Ala Lys Ile Ala Ala Phe Gly Ser Thr Arg Arg Ala Lys
65                  70                  75                  80

Val Thr Pro Asp Lys Asp His Asn Leu Lys Thr Leu Ile Gln Ala Glu
                85                  90                  95

Pro Asp Val Cys Thr Ile Phe Gly Lys Thr Trp Asp Phe His Val His
            100                 105                 110

Glu Ala Leu Arg Ile Ser Leu Glu Glu Asn Leu Glu Leu Ile Phe Asp
        115                 120                 125

Ser Leu Glu Tyr Leu Lys Ala Asn Val Pro Glu Val Phe Tyr Asp Ala
    130                 135                 140

Glu His Phe Phe Asp Gly Tyr Lys Ala Asn Pro Asp Tyr Ala Ile Lys
145                 150                 155                 160

Thr Leu Lys Ala Ala Gln Asp Ala Lys Ala Asp Cys Ile Val Leu Cys
                165                 170                 175

Asp Thr Asn Gly Gly Thr Met Pro Phe Glu Leu Val Glu Ile Ile Arg
            180                 185                 190

Glu Val Arg Lys His Ile Thr Ala Pro Leu Gly Ile His Thr His Asn
        195                 200                 205

Asp Ser Glu Cys Ala Val Ala Asn Ser Leu His Ala Val Ser Glu Gly
    210                 215                 220

Ile Val Gln Val Gln Gly Thr Ile Asn Gly Phe Gly Glu Arg Cys Gly
225                 230                 235                 240

Asn Ala Asn Leu Cys Ser Ile Ile Pro Ala Leu Lys Leu Lys Met Lys
                245                 250                 255

Arg Glu Cys Ile Gly Asp Asp Gln Leu Arg Lys Leu Arg Asp Leu Ser
            260                 265                 270

Arg Phe Val Tyr Glu Leu Ala Asn Leu Ser Pro Asn Lys His Gln Ala
        275                 280                 285

Tyr Val Gly Asn Ser Ala Phe Ala His Lys Gly Gly Val His Val Ser
    290                 295                 300

Ala Ile Gln Arg His Pro Glu Thr Tyr Glu His Leu Arg Pro Glu Leu
305                 310                 315                 320

Val Gly Asn Met Thr Arg Val Leu Val Ser Asp Leu Ser Gly Arg Ser
                325                 330                 335

Asn Ile Leu Ala Lys Ala Glu Glu Phe Asn Ile Lys Met Asp Ser Lys
            340                 345                 350

Asp Pro Val Thr Leu Glu Ile Leu Glu Asn Ile Lys Glu Met Glu Asn
        355                 360                 365

Arg Gly Tyr Gln Phe Glu Gly Ala Glu Ala Ser Phe Glu Leu Leu Met

```
                370                 375                 380
Lys Arg Ala Leu Gly Thr His Arg Lys Phe Phe Ser Val Ile Gly Phe
385                 390                 395                 400

Arg Val Ile Asp Glu Lys Arg His Glu Asp Gln Lys Pro Leu Ser Glu
                405                 410                 415

Ala Thr Ile Met Val Lys Val Gly Gly Lys Ile Glu His Thr Ala Ala
                420                 425                 430

Glu Gly Asn Gly Pro Val Asn Ala Leu Asp Asn Ala Leu Arg Lys Ala
            435                 440                 445

Leu Glu Lys Phe Tyr Pro Arg Leu Lys Glu Val Lys Leu Leu Asp Tyr
        450                 455                 460

Lys Val Arg Val Leu Pro Ala Gly Gln Gly Thr Ala Ser Ser Ile Arg
465                 470                 475                 480

Val Leu Ile Glu Ser Gly Asp Lys Glu Ser Arg Trp Gly Thr Val Gly
                485                 490                 495

Val Ser Glu Asn Ile Val Asp Ala Ser Tyr Gln Ala Leu Leu Asp Ser
            500                 505                 510

Val Glu Tyr Lys Leu His Lys Ser Glu Glu Ile Glu Gly Ser Lys Lys
        515                 520                 525

<210> SEQ ID NO 3
<211> LENGTH: 520
<212> TYPE: PRT
<213> ORGANISM: Thermoanaerobacter sp

<400> SEQUENCE: 3

Met Arg Asn Ile Arg Ile Tyr Asp Thr Thr Leu Arg Asp Gly Val Gln
1               5                   10                  15

Gly Gln Gly Ile Ser Phe Thr Val Glu Asp Lys Leu Lys Ile Val Lys
            20                  25                  30

Val Leu Asp Glu Phe Gly Val Ala Tyr Ile Glu Ala Gly Asn Pro Gly
        35                  40                  45

Ser Asn Pro Lys Asp Ile Glu Phe Phe Glu Arg Val Lys Asn Ile Lys
    50                  55                  60

Leu Lys Asn Ala Lys Leu Ile Ala Phe Gly Ser Thr Arg Arg Ala Asn
65                  70                  75                  80

Thr Thr Thr Glu Glu Asp Ala Asn Val Ile Ser Leu Leu Asn Ala Asp
                85                  90                  95

Thr Glu Val Val Thr Ile Phe Gly Lys Ser Trp Asp Phe Gln Val Thr
            100                 105                 110

Glu Ile Leu Lys Thr Thr Leu Glu Glu Asn Leu Lys Met Ile Tyr Asp
        115                 120                 125

Thr Val Lys Phe Phe Lys Asp Lys Gly Lys Ser Val Ile Phe Asp Ala
    130                 135                 140

Glu His Phe Phe Asp Gly Tyr Lys Gln Asn Pro Glu Tyr Ala Leu Lys
145                 150                 155                 160

Thr Leu Glu Val Ala Leu Glu Ala Gly Val Asp Ser Val Cys Leu Cys
                165                 170                 175

Asp Thr Lys Gly Gly Ala Phe Pro Met Glu Val Tyr Asp Ile Thr Lys
            180                 185                 190

Thr Val Val Asp Lys Phe Asn Thr Glu Val Gly Ile His Cys His Asn
        195                 200                 205

Asp Asn Gly Met Ala Val Ala Asp Ser Ile Met Ala Val Gln Ala Gly
    210                 215                 220
```

Ala Ile Gln Leu Gln Gly Thr Ile Asn Gly Tyr Gly Glu Arg Cys Gly
225                 230                 235                 240

Asn Ala Asn Leu Cys Thr Leu Ile Pro Asn Leu Gln Leu Leu Met Gly
            245                 250                 255

Tyr Lys Cys Val Pro Asp Glu Asn Leu Lys Gln Leu Thr His Leu Ala
            260                 265                 270

Arg Phe Val Ser Glu Ile Ala Asn Val Thr Tyr Asp Glu Arg Ala Pro
            275                 280                 285

Tyr Val Gly Lys Asn Ala Phe Ser His Lys Ala Gly Met His Ala Asp
290                 295                 300

Ala Val Asn Lys Asn Thr Tyr Ser Tyr Glu Leu Ile Asp Pro Ser Leu
305                 310                 315                 320

Val Gly Asn Ser Arg Thr Phe Leu Ile Ser Glu Val Ala Gly Arg Gly
            325                 330                 335

Ala Val Leu Asn Ala Ile Asn Glu Ile Asp Pro Thr Ile Thr Lys Asp
            340                 345                 350

Ser Pro Glu Thr Lys Leu Ile Leu Asp Lys Leu Lys Glu Met Glu Tyr
            355                 360                 365

Leu Gly Tyr Gln Tyr Glu Asn Ala Gly Gly Ser Leu Glu Leu Leu Ile
370                 375                 380

Arg Lys Val Leu Gly Lys Tyr Lys Pro Ala Phe Asn Leu Lys Glu Phe
385                 390                 395                 400

Lys Val Ile Val Asn Glu Pro Ser Val Asn Ser Val Asn Ser Ser Ala
                405                 410                 415

Leu Ile Lys Val Glu Val Asp Ser Ile Glu Glu Ile Ala Ala Ala Glu
            420                 425                 430

Gly Asp Gly Pro Val His Ala Leu Asp Asn Ala Val Arg Arg Val Leu
            435                 440                 445

Glu Arg Phe Tyr Pro Gln Ile Lys Glu Met Arg Leu Thr Asp Tyr Lys
            450                 455                 460

Val Arg Val Leu Asp Ser Asn Ser Ala Thr Ala Ala Lys Val Arg Val
465                 470                 475                 480

Ile Ile Glu Ser Thr Asp Gly Lys Asp Ser Trp Ser Thr Ile Gly Val
            485                 490                 495

Ser Thr Asp Ile Ile Glu Ala Ser Trp Arg Ala Leu Val Asp Ser Ile
            500                 505                 510

Glu Tyr Lys Leu Asn Lys Glu Ser
            515                 520

<210> SEQ ID NO 4
<211> LENGTH: 373
<212> TYPE: PRT
<213> ORGANISM: Artificial
<220> FEATURE:
<223> OTHER INFORMATION: citramalate synthase enzyme CimA3.7

<400> SEQUENCE: 4

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Val Thr
            35                  40                  45

Ser Lys Gly Glu Arg Glu Gly Ile Lys Leu Ile Thr Lys Glu Gly Leu
50                  55                  60

```
Asn Ala Glu Ile Cys Ser Phe Val Arg Ala Leu Pro Val Asp Ile Asp
 65                  70                  75                  80

Ala Ala Leu Glu Cys Asp Val Asp Ser Val His Leu Val Pro Thr
                 85                  90                  95

Ser Pro Ile His Met Lys Tyr Lys Leu Arg Lys Thr Glu Asp Glu Val
                100                 105                 110

Leu Val Thr Ala Leu Lys Ala Val Glu Tyr Ala Lys Glu Gln Gly Leu
            115                 120                 125

Ile Val Glu Leu Ser Ala Glu Asp Ala Thr Arg Ser Asp Val Asn Phe
130                 135                 140

Leu Ile Lys Leu Phe Asn Glu Gly Lys Val Gly Ala Asp Arg Val
145                 150                 155                 160

Cys Val Cys Asp Thr Val Gly Val Leu Thr Pro Gln Lys Ser Gln Glu
                165                 170                 175

Leu Phe Lys Lys Ile Thr Glu Asn Val Asn Leu Pro Val Ser Val His
            180                 185                 190

Cys His Asn Asp Phe Gly Met Ala Thr Ala Asn Ala Cys Ser Ala Val
        195                 200                 205

Leu Gly Gly Ala Val Gln Cys His Val Thr Val Asn Gly Ile Gly Glu
210                 215                 220

Arg Ala Gly Asn Ala Ser Leu Glu Glu Val Val Ala Ala Ser Lys Ile
225                 230                 235                 240

Leu Tyr Gly Tyr Asp Thr Lys Ile Lys Met Glu Lys Leu Tyr Glu Val
                245                 250                 255

Ser Arg Ile Val Ser Arg Leu Met Lys Leu Pro Val Pro Pro Asn Lys
            260                 265                 270

Ala Ile Val Gly Asp Asn Ala Phe Ala His Glu Ala Gly Ile His Val
        275                 280                 285

Asp Gly Leu Ile Lys Asn Thr Glu Thr Tyr Glu Pro Ile Lys Pro Glu
290                 295                 300

Met Val Gly Asn Arg Arg Arg Ile Ile Leu Gly Lys His Ser Gly Arg
305                 310                 315                 320

Lys Ala Leu Lys Tyr Lys Leu Asp Leu Met Gly Ile Asn Val Ser Asp
                325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
        355                 360                 365

Thr Gly Lys Leu Val
    370

<210> SEQ ID NO 5
<211> LENGTH: 426
<212> TYPE: PRT
<213> ORGANISM: Escherichia coli

<400> SEQUENCE: 5

Ala Asp Thr Lys Ala Lys Leu Thr Leu Asn Gly Asp Thr Ala Val Glu
 1               5                  10                  15

Leu Asp Val Leu Lys Gly Thr Leu Gly Gln Asp Val Ile Asp Ile Arg
                 20                  25                  30

Thr Leu Gly Ser Lys Gly Val Phe Thr Phe Asp Pro Gly Phe Thr Ser
            35                  40                  45

Thr Ala Ser Cys Glu Ser Lys Ile Thr Phe Ile Asp Gly Asp Glu Gly
        50                  55                  60
```

Ile Leu Leu His Arg Gly Phe Pro Ile Asp Gln Leu Ala Thr Asp Ser
 65                  70                  75                  80

Asn Tyr Leu Glu Val Cys Tyr Ile Leu Leu Asn Gly Glu Lys Pro Thr
                 85                  90                  95

Gln Glu Gln Tyr Asp Glu Phe Lys Thr Thr Val Thr Arg His Thr Met
            100                 105                 110

Ile His Glu Gln Ile Thr Arg Leu Phe His Ala Phe Arg Arg Asp Ser
        115                 120                 125

His Pro Met Ala Val Met Cys Gly Ile Thr Gly Ala Leu Ala Ala Phe
130                 135                 140

Tyr His Asp Ser Leu Asp Val Asn Asn Pro Arg His Arg Glu Ile Ala
145                 150                 155                 160

Ala Phe Arg Leu Leu Ser Lys Met Pro Thr Met Ala Ala Met Cys Tyr
                165                 170                 175

Lys Tyr Ser Ile Gly Gln Pro Phe Val Tyr Pro Arg Asn Asp Leu Ser
            180                 185                 190

Tyr Ala Gly Asn Phe Leu Asn Met Met Phe Ser Thr Pro Cys Glu Pro
        195                 200                 205

Tyr Glu Val Asn Pro Ile Leu Glu Arg Ala Met Asp Arg Ile Leu Ile
210                 215                 220

Leu His Ala Asp His Glu Gln Asn Ala Ser Thr Ser Thr Val Arg Thr
225                 230                 235                 240

Ala Gly Ser Ser Gly Ala Asn Pro Phe Ala Cys Ile Ala Ala Gly Ile
                245                 250                 255

Ala Ser Leu Trp Gly Pro Ala His Gly Gly Ala Asn Glu Ala Ala Leu
            260                 265                 270

Lys Met Leu Glu Glu Ile Ser Ser Val Lys His Ile Pro Glu Phe Val
        275                 280                 285

Arg Arg Ala Lys Asp Lys Asn Asp Ser Phe Arg Leu Met Gly Phe Gly
290                 295                 300

His Arg Val Tyr Lys Asn Tyr Asp Pro Arg Ala Thr Val Met Arg Glu
305                 310                 315                 320

Thr Cys His Glu Val Leu Lys Glu Leu Gly Thr Lys Asp Asp Leu Leu
                325                 330                 335

Glu Val Ala Met Glu Leu Glu Asn Ile Ala Leu Asn Asp Pro Tyr Phe
            340                 345                 350

Ile Glu Lys Lys Leu Tyr Pro Asn Val Asp Phe Tyr Ser Gly Ile Ile
        355                 360                 365

Leu Lys Ala Met Gly Ile Pro Ser Ser Met Phe Thr Val Ile Phe Ala
370                 375                 380

Met Ala Arg Thr Val Gly Trp Ile Ala His Trp Ser Glu Met His Ser
385                 390                 395                 400

Asp Gly Met Lys Ile Ala Arg Pro Arg Gln Leu Tyr Thr Gly Tyr Glu
                405                 410                 415

Lys Arg Asp Phe Lys Ser Asp Ile Lys Arg
            420                 425

<210> SEQ ID NO 6
<211> LENGTH: 427
<212> TYPE: PRT
<213> ORGANISM: Klebsiella pneumoniae

<400> SEQUENCE: 6

Met Ser Asp Ala Lys Ala Lys Ile Thr Leu Gly Gly Asp Thr Ala Ile

```
  1               5                   10                  15
Glu Leu Asp Val Leu Lys Gly Thr Leu Gly Gln Asp Val Ile Asp Ile
             20                  25                  30

Arg Ser Leu Gly Ser Lys Gly Val Phe Thr Phe Asp Pro Gly Phe Thr
             35                  40                  45

Ser Thr Ala Ser Cys Glu Ser Lys Ile Thr Phe Ile Asp Gly Asp Glu
             50                  55                  60

Gly Ile Leu Leu His Arg Gly Phe Pro Ile Asp Gln Leu Ala Thr Glu
 65                  70                  75                  80

Ser Asn Tyr Leu Glu Val Cys Tyr Ile Leu Leu Tyr Gly Glu Lys Pro
                 85                  90                  95

Thr Gln Ala Glu Tyr Asp Glu Phe Lys Thr Thr Val Thr Arg His Thr
            100                 105                 110

Met Ile His Glu Gln Ile Thr Arg Leu Phe His Ala Phe Arg Arg Asp
            115                 120                 125

Ser His Pro Met Ala Val Met Cys Gly Ile Thr Gly Ala Leu Ala Ala
            130                 135                 140

Phe Tyr His Asp Ser Leu Asp Val Asn Asn Pro Arg His Arg Glu Ile
145                 150                 155                 160

Ala Ala Tyr Arg Leu Leu Ser Lys Met Pro Thr Met Ala Ala Met Cys
            165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Arg Met Met Phe Ala Thr Pro Cys Glu
            195                 200                 205

Glu Tyr Glu Val Asn Pro Val Leu Glu Arg Ala Met Asp Arg Ile Leu
            210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
            245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Glu His Ile Pro Glu Phe
            275                 280                 285

Val Arg Arg Ala Lys Asp Lys Asn Asp Ser Phe Arg Leu Met Gly Phe
            290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
            325                 330                 335

Leu Gln Val Ala Met Glu Leu Glu His Ile Ala Leu Asn Asp Pro Tyr
            340                 345                 350

Phe Ile Glu Lys Lys Leu Tyr Pro Asn Val Asp Phe Tyr Ser Gly Ile
            355                 360                 365

Ile Leu Lys Ala Met Gly Ile Pro Ser Ser Met Phe Thr Val Ile Phe
            370                 375                 380

Ala Met Ala Arg Thr Val Gly Trp Ile Ala His Trp Asn Glu Met His
385                 390                 395                 400

Ser Asp Gly Met Lys Ile Ala Arg Pro Arg Gln Leu Tyr Thr Gly Tyr
            405                 410                 415

Ala Lys Arg Asp Phe Gln Ser Asp Ile Lys Arg
            420                 425
```

<210> SEQ ID NO 7
<211> LENGTH: 429
<212> TYPE: PRT
<213> ORGANISM: Pseudomonas putida

<400> SEQUENCE: 7

```
Met Ala Asp Lys Lys Ala Gln Leu Val Ile Glu Gly Ala Ala Pro Val
1               5                   10                  15

Glu Leu Pro Ile Leu Thr Gly Thr Val Gly Pro Asp Val Ile Asp Val
                20                  25                  30

Arg Gly Leu Gly Ala Thr Gly His Phe Thr Phe Asp Pro Gly Phe Met
            35                  40                  45

Ala Thr Ala Ser Cys Glu Ser Lys Ile Thr Tyr Ile Asp Gly Asp Lys
        50                  55                  60

Gly Ile Leu Leu His Arg Gly Tyr Pro Ile Glu Gln Leu Ala Glu Gln
65                  70                  75                  80

Ser Asp Tyr Leu Glu Thr Cys Tyr Leu Leu Asn Gly Glu Leu Pro
                85                  90                  95

Asn Ala Glu Gln Lys Ala Gln Phe Val Ser Thr Val Lys Asn His Thr
            100                 105                 110

Met Val His Glu Gln Leu Lys Ser Phe Phe Asn Gly Phe Arg Arg Asp
        115                 120                 125

Ala His Pro Met Ala Val Met Cys Gly Val Val Gly Ala Leu Ser Ala
130                 135                 140

Phe Tyr His Asp Ser Leu Asp Ile Asn Asn Pro Gln His Arg Glu Ile
145                 150                 155                 160

Ser Ala Val Arg Leu Val Ala Lys Met Pro Thr Leu Ala Ala Met Val
                165                 170                 175

Tyr Lys Tyr Ser Met Gly Gln Pro Met Met Tyr Pro Arg Asn Asp Leu
            180                 185                 190

Ser Tyr Ala Glu Asn Phe Leu His Met Met Phe Asn Thr Pro Cys Glu
        195                 200                 205

Ile Lys Pro Ile Ser Pro Val Leu Ala Lys Ala Met Asp Arg Ile Phe
210                 215                 220

Ile Leu His Ala Asp His Glu Gln Asn Ala Ser Thr Ser Thr Val Arg
225                 230                 235                 240

Leu Ala Gly Ser Ser Gly Ala Asn Pro Phe Ala Cys Ile Ala Ala Gly
                245                 250                 255

Ile Ala Ala Leu Trp Gly Pro Ala His Gly Gly Ala Asn Glu Ala Val
            260                 265                 270

Leu Thr Met Leu Asp Glu Ile Gly Asp Val Ser Asn Ile Asp Lys Phe
        275                 280                 285

Ile Ala Lys Ala Lys Asp Lys Asn Asp Pro Phe Lys Leu Met Gly Phe
290                 295                 300

Gly His Arg Val Tyr Lys Asn Arg Asp Pro Arg Ala Thr Val Met Lys
305                 310                 315                 320

Gln Thr Cys Asp Glu Val Leu Arg Glu Leu Gly Ile Lys Asn Asp Pro
                325                 330                 335

Gln Leu Glu Leu Ala Met Arg Leu Glu Ile Ala Leu Thr Asp Pro
            340                 345                 350

Tyr Phe Ile Glu Arg Ser Leu Tyr Pro Asn Val Asp Phe Tyr Ser Gly
        355                 360                 365

Ile Ile Leu Lys Ala Ile Gly Ile Pro Thr Ser Met Phe Thr Val Ile
```

```
                  370                 375                 380
Phe Ala Leu Ala Arg Thr Val Gly Trp Ile Ser His Trp Lys Glu Met
385                 390                 395                 400

Leu Ser Ser Pro Tyr Lys Ile Gly Arg Pro Arg Gln Leu Tyr Thr Gly
                405                 410                 415

Glu Gln Lys Arg Asp Ile Val Ala Leu Lys Asp Arg Lys
                420                 425
```

<210> SEQ ID NO 8
<211> LENGTH: 437
<212> TYPE: PRT
<213> ORGANISM: Corynebacterium glutamicum

<400> SEQUENCE: 8

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
                20                  25                  30

Gly Asn Asn Gly Val Val Leu Gly Lys Met Leu Ser Glu Thr Gly Leu
            35                  40                  45

Ile Thr Phe Asp Pro Gly Tyr Val Ser Thr Gly Ser Thr Glu Ser Lys
50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
290                 295                 300

Lys Glu Asp Gly Val Arg Leu Met Gly Phe Gly His Arg Val Tyr Lys
305                 310                 315                 320
```

```
Asn Tyr Asp Pro Arg Ala Ala Ile Val Lys Glu Thr Ala His Glu Ile
            325                 330                 335

Leu Glu His Leu Gly Gly Asp Asp Leu Leu Asp Leu Ala Ile Lys Leu
        340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
        370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
            405                 410                 415

Asn Arg Pro Arg Gln Val Tyr Thr Gly Asn Glu Ser Arg Lys Leu Val
            420                 425                 430

Pro Arg Glu Glu Arg
            435

<210> SEQ ID NO 9
<211> LENGTH: 366
<212> TYPE: PRT
<213> ORGANISM: Bacillus subtilis

<400> SEQUENCE: 9

Met Val His Tyr Gly Leu Lys Gly Ile Thr Cys Val Glu Thr Ser Ile
1               5                   10                  15

Ser His Ile Asp Gly Glu Lys Gly Arg Leu Ile Tyr Arg Gly His His
            20                  25                  30

Ala Lys Asp Ile Ala Leu Asn His Ser Phe Glu Glu Ala Ala Tyr Leu
        35                  40                  45

Ile Leu Phe Gly Lys Leu Pro Ser Thr Glu Glu Leu Gln Val Phe Lys
    50                  55                  60

Asp Lys Leu Ala Ala Glu Arg Asn Leu Pro Glu His Ile Glu Arg Leu
65                  70                  75                  80

Ile Gln Ser Leu Pro Asn Asn Met Asp Asp Met Ser Val Leu Arg Thr
                85                  90                  95

Val Val Ser Ala Leu Gly Glu Asn Thr Tyr Thr Phe His Pro Lys Thr
            100                 105                 110

Glu Glu Ala Ile Arg Leu Ile Ala Ile Thr Pro Ser Ile Ile Ala Tyr
        115                 120                 125

Arg Lys Arg Trp Thr Arg Gly Glu Gln Ala Ile Ala Pro Ser Ser Gln
    130                 135                 140

Tyr Gly His Val Glu Asn Tyr Tyr Met Leu Thr Gly Glu Gln Pro
145                 150                 155                 160

Ser Glu Ala Lys Lys Lys Ala Leu Glu Thr Tyr Met Ile Leu Ala Thr
                165                 170                 175

Glu His Gly Met Asn Ala Ser Thr Phe Ser Ala Arg Val Thr Leu Ser
            180                 185                 190

Thr Glu Ser Asp Leu Val Ser Ala Val Thr Ala Ala Leu Gly Thr Met
        195                 200                 205

Lys Gly Pro Leu His Gly Ala Pro Ser Ala Val Thr Lys Met Leu
    210                 215                 220

Glu Asp Ile Gly Glu Lys Glu His Ala Glu Ala Tyr Leu Lys Glu Lys
225                 230                 235                 240

Leu Glu Lys Gly Glu Arg Leu Met Gly Phe Gly His Arg Val Tyr Lys
                245                 250                 255
```

```
Thr Lys Asp Pro Arg Ala Glu Ala Leu Arg Gln Lys Ala Glu Glu Val
            260                 265                 270

Ala Gly Asn Asp Arg Asp Leu Asp Leu Ala Leu His Val Glu Ala Glu
        275                 280                 285

Ala Ile Arg Leu Leu Glu Ile Tyr Lys Pro Gly Arg Lys Leu Tyr Thr
    290                 295                 300

Asn Val Glu Phe Tyr Ala Ala Val Met Arg Ala Ile Asp Phe Asp
305                 310                 315                 320

Asp Glu Leu Phe Thr Pro Thr Phe Ser Ala Ser Arg Met Val Gly Trp
                325                 330                 335

Cys Ala His Val Leu Glu Gln Ala Glu Asn Asn Met Ile Phe Arg Pro
            340                 345                 350

Ser Ala Gln Tyr Thr Gly Ala Ile Pro Glu Glu Val Leu Ser
        355                 360                 365

<210> SEQ ID NO 10
<211> LENGTH: 372
<212> TYPE: PRT
<213> ORGANISM: Geobacillus stearothermophilus

<400> SEQUENCE: 10

Met Thr Val Thr Arg Gly Leu Glu Gly Val Ala Thr Thr Ser Ser
1               5                   10                  15

Ile Ser Ser Ile Ile Asp Asp Thr Leu Thr Tyr Val Gly Tyr Asp Ile
                20                  25                  30

Asp Asp Leu Ala Glu Asn Ala Ser Phe Glu Glu Val Val Tyr Leu Leu
            35                  40                  45

Trp His Arg Glu Leu Pro Thr Lys Glu Gln Leu Glu Glu Leu Lys Lys
    50                  55                  60

Gln Leu Ala Glu Asn Ala Glu Ile Pro Asn Glu Ile Glu His Phe
65                  70                  75                  80

Lys Leu Tyr Pro Ile Asp Lys Val His Pro Met Ala Ala Leu Arg Thr
                85                  90                  95

Ala Val Ser Leu Leu Gly Leu Tyr Asp Glu Glu Ala Asp Val Met Thr
            100                 105                 110

Lys Glu Ala Asn Tyr Arg Lys Ala Ile Arg Leu Gln Ala Lys Ile Pro
        115                 120                 125

Thr Ile Val Thr Ala Phe Ala Arg Val Arg Lys Gly Leu Glu Pro Val
    130                 135                 140

Ala Pro Arg Lys Asp Leu Ser Phe Ala Ala Asn Phe Leu Tyr Met Leu
145                 150                 155                 160

Thr Gly Lys Glu Pro Asp Asp Ile Ala Thr Glu Ala Phe Asn Lys Ala
                165                 170                 175

Leu Val Leu His Ala Asp His Glu Leu Asn Ala Ser Thr Phe Thr Ala
            180                 185                 190

Arg Val Cys Val Ala Thr Leu Ser Asp Ile Tyr Ser Gly Ile Thr Ala
        195                 200                 205

Ala Ile Gly Ala Leu Lys Gly Pro Leu His Gly Gly Ala Asn Glu Ala
    210                 215                 220

Val Met Lys Met Leu Thr Glu Ile Gly Thr Val Asp Asn Val Glu Pro
225                 230                 235                 240

Tyr Ile Arg Arg Lys Leu Ala Asn Lys Glu Lys Ile Met Gly Phe Gly
                245                 250                 255

His Arg Val Tyr Arg Lys Gly Asp Pro Arg Ala Lys His Leu Lys Lys
```

```
              260                 265                 270
Met Ser Glu Lys Leu Thr Lys Leu Val Gly Glu Pro His Trp Tyr Glu
            275                 280                 285

Met Ser Thr Lys Ile Glu Glu Ile Val Thr Ser Glu Lys Ala Leu Pro
        290                 295                 300

Pro Asn Val Asp Phe Tyr Ser Ala Ser Val Tyr His Cys Leu Gly Ile
305                 310                 315                 320

Asp His Asp Leu Phe Thr Pro Ile Phe Ala Val Ser Arg Thr Ser Gly
                325                 330                 335

Trp Leu Ala His Ile Leu Glu Gln Tyr Asp Asn Asn Arg Leu Ile Arg
            340                 345                 350

Pro Arg Ala Glu Tyr Thr Gly Pro Gly Lys Arg Ala Tyr Val Pro Ile
        355                 360                 365

Asp Glu Arg Gly
        370

<210> SEQ ID NO 11
<211> LENGTH: 432
<212> TYPE: PRT
<213> ORGANISM: Lactococcus lactis

<400> SEQUENCE: 11

Met Ile Lys Asn Ser Gln Ile Pro Ser Glu Phe Tyr Lys Lys Tyr Asn
1               5                   10                  15

Val Lys Lys Gly Leu Arg Asp Ile Asn Gly Lys Gly Val Leu Ala Gly
            20                  25                  30

Leu Thr Asn Ile Ser Ala Ile His Ser Phe Asp Lys Glu Gly Asn Gln
        35                  40                  45

Ile Pro Gly Ile Leu Glu Tyr Arg Ala Tyr Asn Ile Lys Asp Ile Ile
    50                  55                  60

Asn Asp Leu Arg Lys Glu Asn Arg Phe Gly Phe Glu Glu Met Thr Tyr
65                  70                  75                  80

Leu Leu Leu Phe Gly Glu Leu Pro Thr Ala Asn Glu Leu Gln Glu Phe
                85                  90                  95

Gln Asn Leu Leu Ala Ser Arg Arg Thr Leu Pro Glu Phe Phe Ile Arg
            100                 105                 110

Glu Thr Ile Leu Thr Asn Pro Ser Ser Asp Val Met Asn Ser Met Ser
        115                 120                 125

Arg Cys Ile Leu Ala Leu Ala Ser Tyr Asp Glu Lys Val Ser Asp Ile
    130                 135                 140

Ser Ile Glu Asn Val Leu Glu Gln Ser Phe Gly Leu Ile Ala Asp Phe
145                 150                 155                 160

Pro Leu Leu Ala Ile Tyr Ser Tyr Gln Ser Tyr Val His Tyr Phe Lys
                165                 170                 175

Lys Glu Ser Leu Tyr Ile His Tyr Pro Asp Pro Lys Met Thr Thr Ala
            180                 185                 190

Glu Asn Ile Leu Arg Met Leu Arg Pro Asp Cys His Tyr Thr Glu Val
        195                 200                 205

Glu Ala Lys Val Leu Asp Ile Ala Leu Ile Leu His Met Glu His Gly
    210                 215                 220

Gly Gly Asn Asn Ser Thr Phe Thr Thr His Val Val Thr Ser Ser Gly
225                 230                 235                 240

Thr Asp Thr Tyr Ala Thr Ile Ala Ala Leu Ser Ser Leu Lys Gly
                245                 250                 255
```

-continued

```
Pro Lys His Gly Gly Ala Asn Ile Lys Ala Ala Lys Met Leu Glu Asn
            260                 265                 270

Ile Lys Glu Asn Ile Ser Asn Tyr Glu Asp Ala Glu Ile Glu Lys
        275                 280                 285

Tyr Leu His Lys Ile Leu Asn Lys Glu Val Phe Asp Lys Gln Gly Leu
    290                 295                 300

Ile Tyr Gly Ile Gly His Ala Ile Tyr Ser Leu Ser Asp Pro Arg Phe
305                 310                 315                 320

Glu Val Phe Lys Ser Tyr Val Glu Thr Leu Val Lys Glu Lys Gly Leu
                325                 330                 335

Glu Glu Glu Phe Lys Leu Tyr Gly Lys Val Ala Arg Leu Ala Pro Lys
            340                 345                 350

Val Ile Ser Glu Asn Arg Lys Ile Tyr Lys Thr Ile Cys Pro Asn Val
        355                 360                 365

Asp Phe Tyr Ser Gly Phe Val Tyr Arg Ile Leu Glu Ile Pro Gln Glu
    370                 375                 380

Leu Phe Thr Pro Leu Phe Ala Ile Ala Arg Ile Val Gly Trp Leu Ala
385                 390                 395                 400

His Arg Ile Glu Glu Leu Ile Asn Met Asn Lys Ile Ile Arg Pro Ala
                405                 410                 415

Tyr Glu Ser Val Leu Glu Ser Lys Asn Tyr Ile Lys Leu Gly Glu Arg
            420                 425                 430

<210> SEQ ID NO 12
<211> LENGTH: 38
<212> TYPE: DNA
<213> ORGANISM: Artificial
<220> FEATURE:
<223> OTHER INFORMATION: primer

<400> SEQUENCE: 12
gggaaaggta ccatgatggt gcgtatcttt gacacgac                                38

<210> SEQ ID NO 13
<211> LENGTH: 33
<212> TYPE: DNA
<213> ORGANISM: Artificial
<220> FEATURE:
<223> OTHER INFORMATION: primer

<400> SEQUENCE: 13
gggaaactca gatcacacca gtttgcccgt cac                                     33

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
tcatgcaaaa cactgcttcc agatg                                              25

<210> SEQ ID NO 15
<211> LENGTH: 27
<212> TYPE: DNA
<213> ORGANISM: Artificial
<220> FEATURE:
<223> OTHER INFORMATION: primer

<400> SEQUENCE: 15
```

```
agagtagaat tcgacgttcg ggtacag                                              27

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
tgtacccgaa cgtcgaattc tactctg                                              27

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
cgtgccattg caataatgac ggtgaac                                              27

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
gttcaccgtc attattgcaa tggcacg                                              27

<210> SEQ ID NO 19
<211> LENGTH: 27
<212> TYPE: DNA
<213> ORGANISM: Artificial
<220> FEATURE:
<223> OTHER INFORMATION: primer

<400> SEQUENCE: 19
gccattgcca gaatgacggt gaacatg                                              27

<210> SEQ ID NO 20
<211> LENGTH: 26
<212> TYPE: DNA
<213> ORGANISM: Artificial
<220> FEATURE:
<223> OTHER INFORMATION: primer

<400> SEQUENCE: 20
ccgtcattct ggcaatggca cgtacc                                               26

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
gtgccattgc cataatgacg gtgaacatg                                            29

<210> SEQ ID NO 22
<211> LENGTH: 24
<212> TYPE: DNA
<213> ORGANISM: Artificial
```

```
<220> FEATURE:
<223> OTHER INFORMATION: primer

<400> SEQUENCE: 22
cgtcattatg gcaatggcac gtac                                          24

<210> SEQ ID NO 23
<211> LENGTH: 26
<212> TYPE: DNA
<213> ORGANISM: Artificial
<220> FEATURE:
<223> OTHER INFORMATION: primer

<400> SEQUENCE: 23
gtgccattgc cacaatgacg gtgaac                                        26

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
cgtcattgtg gcaatggcac gtac                                          24

<210> SEQ ID NO 25
<211> LENGTH: 45
<212> TYPE: DNA
<213> ORGANISM: Artificial
<220> FEATURE:
<223> OTHER INFORMATION: primer

<400> SEQUENCE: 25
gaagcagctc cagcctacac caacttagca atcaaccatt aacgc                   45

<210> SEQ ID NO 26
<211> LENGTH: 45
<212> TYPE: DNA
<213> ORGANISM: Artificial
<220> FEATURE:
<223> OTHER INFORMATION: primer

<400> SEQUENCE: 26
gcgttaatgg ttgattgcta agttggtgta ggctggagct gcttc                   45

<210> SEQ ID NO 27
<211> LENGTH: 52
<212> TYPE: DNA
<213> ORGANISM: Artificial
<220> FEATURE:
<223> OTHER INFORMATION: primer

<400> SEQUENCE: 27
catatgaacg gcgggttaaa atatttaatg ggaattagcc atggtccata tg           52

<210> SEQ ID NO 28
<211> LENGTH: 52
<212> TYPE: DNA
<213> ORGANISM: Artificial
<220> FEATURE:
<223> OTHER INFORMATION: primer

<400> SEQUENCE: 28
catatggacc atggctaatt cccattaaat attttaaccc gccgttcata tg           52
```

```
<210> SEQ ID NO 29
<211> LENGTH: 27
<212> TYPE: DNA
<213> ORGANISM: Artificial
<220> FEATURE:
<223> OTHER INFORMATION: primer

<400> SEQUENCE: 29
gttgtcgtga cttgtccaag atctatg                                          27

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
actacgggca cagaggttaa ctttc                                            25

<210> SEQ ID NO 31
<211> LENGTH: 23
<212> TYPE: DNA
<213> ORGANISM: Artificial
<220> FEATURE:
<223> OTHER INFORMATION: primer

<400> SEQUENCE: 31
ctgcctcgtc ctgcagttca ttc                                              23
```